US009925333B2

(12) United States Patent
Hooven et al.

(10) Patent No.: US 9,925,333 B2
(45) Date of Patent: Mar. 27, 2018

(54) VIAL TRANSFER AND INJECTION APPARATUS AND METHOD

(71) Applicant: Enable Injections, Inc., Cincinnati, OH (US)

(72) Inventors: Michael D. Hooven, Cincinnati, OH (US); Matthew J. Huddleston, Loveland, OH (US); Joetta Renee Palmer, Mason, OH (US); David Stefanchik, Morrow, OH (US)

(73) Assignee: Enable Injections, Inc., Cincinnati, OH (US)

( * ) Notice: Subject to any disclaimer, the term of this patent is extended or adjusted under 35 U.S.C. 154(b) by 30 days.

(21) Appl. No.: 14/888,303

(22) PCT Filed: Jun. 17, 2014

(86) PCT No.: PCT/US2014/042627
§ 371 (c)(1),
(2) Date: Oct. 30, 2015

(87) PCT Pub. No.: WO2014/204894
PCT Pub. Date: Dec. 24, 2014

(65) Prior Publication Data
US 2016/0144105 A1 May 26, 2016

Related U.S. Application Data

(60) Provisional application No. 61/979,816, filed on Apr. 15, 2014, provisional application No. 61/836,266, filed on Jun. 18, 2013.

(51) Int. Cl.
*A61M 5/152* (2006.01)
*A61M 5/178* (2006.01)
(Continued)

(52) U.S. Cl.
CPC .......... *A61M 5/152* (2013.01); *A61M 5/1782* (2013.01); *A61M 5/20* (2013.01);
(Continued)

(58) Field of Classification Search
CPC ...... A61M 5/512; A61M 5/1782; A61M 5/20; A61M 5/002; A61M 5/31591;
(Continued)

(56) References Cited

U.S. PATENT DOCUMENTS 605,693 A 6/1898 Black
2,584,397 A 2/1952 Pitman
(Continued)

FOREIGN PATENT DOCUMENTS

EP 699090 3/1996
EP 0800032 A1 10/1997
(Continued)

OTHER PUBLICATIONS

PCT International Search Report for PCT/US2013/059359 dated Dec. 18, 2013.
(Continued)

*Primary Examiner* — Imani Hayman
*Assistant Examiner* — Tezita Watts
(74) *Attorney, Agent, or Firm* — Cook Alex, Ltd.

(57) ABSTRACT

Drug delivery system, injection device, transfer apparatus, vial holder and method of administering and transferring are disclosed. The system may include transfer apparatus and an injection device. The transfer apparatus may have receiving stations for a drug source, such as a vial or vial holder, and for an injection device, and fluid flow pathways for transferring drugs from the source into the injection device. The injection device may include an expandable elastic bladder and an injection cannula that is movable between a plurality of positions.

23 Claims, 44 Drawing Sheets

(51) Int. Cl.
*A61M 5/20* (2006.01)
*A61M 5/00* (2006.01)
*A61M 5/315* (2006.01)
*A61M 5/24* (2006.01)
*A61M 5/31* (2006.01)

(52) U.S. Cl.
CPC ......... *A61M 5/002* (2013.01); *A61M 5/31591* (2013.01); *A61M 2005/206* (2013.01); *A61M 2005/2414* (2013.01); *A61M 2005/3123* (2013.01); *A61M 2005/3128* (2013.01)

(58) Field of Classification Search
CPC .... A61M 2005/206; A61M 2005/2414; A61M 2005/3128; A61M 5/14244; A61M 5/14248; A61M 5/3287; A61M 2005/1583; A61M 5/12; A61M 5/315915; A61M 2205/3334; A61M 5/142; A61M 5/14593; A61M 5/1452; A61M 5/1483; B65D 83/0061
See application file for complete search history.

(56) References Cited

U.S. PATENT DOCUMENTS

| | | |
|---|---|---|
| 2,737,948 A | 3/1956 | Brown |
| 2,941,531 A | 6/1960 | Stevens |
| 3,016,895 A | 1/1962 | Sein |
| 3,089,491 A | 5/1963 | Mirow |
| 3,343,538 A | 9/1967 | Morley |
| 3,469,578 A * | 9/1969 | Bierman ............ A61M 5/152 128/DIG. 12 |
| 3,608,550 A | 9/1971 | Stawski |
| 3,938,520 A | 2/1976 | Scislowicz et al. |
| 3,941,171 A | 3/1976 | Ogle |
| 3,970,106 A | 7/1976 | Harris |
| 3,993,069 A | 11/1976 | Buckles et al. |
| 4,031,889 A | 6/1977 | Pike |
| 4,201,207 A | 5/1980 | Buckles et al. |
| 4,337,769 A | 7/1982 | Olson |
| 4,386,929 A | 6/1983 | Peery et al. |
| 4,387,833 A | 6/1983 | Venus, Jr. |
| 4,419,096 A | 12/1983 | Leeper et al. |
| 4,525,164 A | 6/1985 | Loeb et al. |
| 4,537,593 A | 8/1985 | Alchas |
| 4,540,400 A | 9/1985 | Hooven |
| 4,543,101 A | 9/1985 | Crouch |
| 4,564,054 A | 1/1986 | Gustavsson |
| 4,583,971 A | 4/1986 | Bocquet et al. |
| 4,619,651 A | 10/1986 | Kopfer et al. |
| 4,671,328 A | 6/1987 | Mueller |
| 4,702,397 A | 10/1987 | Gortz |
| 4,734,092 A | 3/1988 | Millerd |
| 4,743,243 A | 5/1988 | Vaillancourt |
| 4,769,002 A | 9/1988 | Hooven |
| 4,776,838 A | 10/1988 | Sainte-Rose et al. |
| 4,823,623 A | 4/1989 | Carpenter et al. |
| 4,886,495 A | 12/1989 | Reynolds |
| 4,886,499 A * | 12/1989 | Cirelli .................. A61M 5/142 128/DIG. 12 |
| 5,011,477 A | 4/1991 | Winchell et al. |
| 5,045,064 A | 9/1991 | Idriss |
| 5,122,116 A | 6/1992 | Kriegel et al. |
| 5,167,641 A | 12/1992 | Schmitz |
| 5,226,900 A | 7/1993 | Bancsi et al. |
| 5,298,023 A | 3/1994 | Haber et al. |
| 5,298,025 A | 3/1994 | Hessel et al. |
| 5,329,976 A | 7/1994 | Haber et al. |
| 5,352,201 A * | 10/1994 | Jemmott ............ A61M 5/152 604/131 |
| 5,360,410 A | 11/1994 | Wacks |
| 5,411,499 A | 5/1995 | Dudar et al. |
| 5,429,607 A | 7/1995 | McPhee |
| 5,466,220 A | 11/1995 | Brenneman |
| 5,503,628 A | 4/1996 | Fetters et al. |
| 5,616,132 A | 4/1997 | Newman |
| 5,636,660 A | 6/1997 | Pfleiderer et al. |
| 5,826,621 A | 10/1998 | Jemmott |
| 5,858,001 A | 1/1999 | Tsals et al. |
| 5,954,695 A | 9/1999 | Sims et al. |
| 5,957,895 A | 9/1999 | Sage |
| 5,989,237 A | 11/1999 | Fowles et al. |
| 6,045,534 A | 4/2000 | Jacobsen et al. |
| 6,113,583 A | 9/2000 | Fowles et al. |
| 6,186,982 B1 | 2/2001 | Gross et al. |
| 6,293,159 B1 | 9/2001 | Kriesol et al. |
| 6,364,865 B1 | 4/2002 | Lavi et al. |
| 6,478,771 B1 | 11/2002 | Lavi et al. |
| 6,571,837 B2 | 6/2003 | Jansen et al. |
| 6,595,950 B1 | 7/2003 | Miles et al. |
| 6,623,447 B2 | 9/2003 | Miles et al. |
| 6,641,565 B1 | 11/2003 | Lavi et al. |
| 6,645,181 B1 | 11/2003 | Lavi et al. |
| 6,685,670 B2 | 2/2004 | Miles et al. |
| 6,719,719 B2 | 4/2004 | Carmel et al. |
| 6,723,068 B2 | 4/2004 | Levi et al. |
| 6,776,776 B2 | 8/2004 | Alchas et al. |
| 6,790,199 B1 | 9/2004 | Gianakos |
| 6,923,785 B2 | 8/2005 | Miles et al. |
| 6,948,552 B2 | 9/2005 | Newbrough et al. |
| 6,960,192 B1 | 11/2005 | Flaherty |
| 6,979,311 B2 | 12/2005 | Miles et al. |
| 6,986,760 B2 | 1/2006 | Giambattista et al. |
| 6,994,691 B2 | 2/2006 | Ejlersen |
| 7,083,599 B2 | 8/2006 | Alchas et al. |
| 7,104,971 B2 | 9/2006 | Hjertman |
| 7,150,727 B2 | 12/2006 | Cise et al. |
| 7,214,221 B2 | 5/2007 | Fentress et al. |
| 7,367,963 B2 | 5/2008 | Cise et al. |
| 7,491,197 B2 | 2/2009 | Jansen et al. |
| 7,540,858 B2 | 6/2009 | DiBiasi |
| 7,597,684 B2 | 10/2009 | Alchas et al. |
| 7,637,891 B2 | 12/2009 | Wall |
| 7,670,314 B2 | 3/2010 | Wall et al. |
| 7,744,581 B2 | 6/2010 | Wallen et al. |
| 7,815,609 B2 | 10/2010 | Hines |
| 7,815,612 B2 | 10/2010 | Cise et al. |
| 7,842,008 B2 | 11/2010 | Clarke et al. |
| D631,153 S | 1/2011 | McGlothlin et al. |
| 7,882,863 B2 | 2/2011 | Pestotnik |
| 7,927,306 B2 | 4/2011 | Cross |
| 7,938,801 B2 | 5/2011 | Hawkins |
| 7,955,297 B2 | 6/2011 | Radmer et al. |
| 7,959,600 B2 | 6/2011 | Chang et al. |
| 7,976,513 B2 | 7/2011 | Cise et al. |
| 7,981,076 B2 | 7/2011 | Sullivan et al. |
| 7,981,081 B2 | 7/2011 | Marsh et al. |
| 7,985,216 B2 | 7/2011 | Daily et al. |
| 8,066,680 B2 | 11/2011 | Alchas et al. |
| 8,070,739 B2 | 12/2011 | Zinger et al. |
| 8,100,853 B2 | 1/2012 | Glynn |
| 8,110,209 B2 | 2/2012 | Prestrelski et al. |
| 8,123,725 B2 | 2/2012 | Carr |
| 8,142,414 B2 | 3/2012 | Patrick et al. |
| 8,147,477 B2 | 4/2012 | Smith et al. |
| 8,162,923 B2 | 4/2012 | Adams |
| 8,186,511 B2 | 5/2012 | Timm |
| 8,273,062 B2 | 9/2012 | Villette |
| 8,276,583 B2 | 10/2012 | Farieta et al. |
| 8,287,500 B2 | 10/2012 | Baba et al. |
| 8,317,743 B2 | 11/2012 | Denenburg |
| 8,348,898 B2 | 1/2013 | Cabiri |
| 8,409,141 B2 | 4/2013 | Johansen et al. |
| 8,409,151 B2 | 4/2013 | Hawkins et al. |
| 8,444,604 B2 | 5/2013 | Cindrich et al. |
| 8,475,403 B2 | 7/2013 | Melsheimer et al. |
| 8,480,623 B2 | 7/2013 | Mernoe et al. |
| 8,523,814 B2 | 9/2013 | Finke |
| 8,529,502 B2 | 9/2013 | Radmer |
| 8,556,862 B2 | 10/2013 | Cronenberg et al. |
| RE44,640 E | 12/2013 | Heiniger |
| 8,597,270 B2 | 12/2013 | Kavazov |
| 8,622,930 B2 | 1/2014 | Freeman et al. |

(56) References Cited

U.S. PATENT DOCUMENTS

| | | | |
|---|---|---|---|
| 8,708,994 B2 | 4/2014 | Pettis et al. | |
| 8,758,299 B2 | 6/2014 | Sadowski et al. | |
| 8,881,774 B2 | 11/2014 | Lanier, Jr. et al. | |
| 8,894,612 B2 | 11/2014 | Hawkins et al. | |
| 8,905,970 B2 | 12/2014 | Bates et al. | |
| 8,979,799 B1 | 3/2015 | Askarinya et al. | |
| 8,979,808 B1 | 3/2015 | Chong et al. | |
| 9,022,987 B2 | 5/2015 | Stearns et al. | |
| 9,138,534 B2 | 9/2015 | Yodfat et al. | |
| 9,173,993 B2 | 11/2015 | Yodfat et al. | |
| 9,174,002 B2 | 11/2015 | Chang et al. | |
| 9,180,244 B2 | 11/2015 | Anderson et al. | |
| 9,220,851 B2 | 12/2015 | Rosen et al. | |
| 9,265,881 B2 | 2/2016 | Montalvo et al. | |
| 9,265,884 B2 | 2/2016 | Chong et al. | |
| 9,272,093 B2 | 3/2016 | Kohli et al. | |
| 9,278,181 B2 | 3/2016 | Meron et al. | |
| 9,364,617 B2 | 6/2016 | Riedel | |
| 9,381,310 B2 | 7/2016 | Iwase et al. | |
| 9,408,980 B2 | 8/2016 | Bruehwiler et al. | |
| 9,463,282 B2 | 10/2016 | Barrow-Williams et al. | |
| 9,550,025 B2 | 1/2017 | Dunne | |
| 9,566,384 B2 | 2/2017 | Gyrn et al. | |
| 9,592,341 B2 | 3/2017 | Jugl et al. | |
| 9,597,461 B2 | 3/2017 | Aasmul | |
| 9,668,914 B2 | 6/2017 | Py et al. | |
| 9,764,084 B2 | 9/2017 | McLoughlin et al. | |
| 9,764,091 B2 | 9/2017 | Bechmann et al. | |
| 9,789,254 B2 | 10/2017 | McLoughlin et al. | |
| 9,801,787 B2 | 10/2017 | Py | |
| 9,808,578 B2 | 11/2017 | Stearns et al. | |
| 9,833,562 B2 | 12/2017 | Sonderegger et al. | |
| 2002/0004648 A1 | 1/2002 | Larsen et al. | |
| 2002/0123719 A1 | 9/2002 | Lavi et al. | |
| 2003/0060776 A1 | 3/2003 | Heiniger | |
| 2004/0015134 A1 | 1/2004 | Lavi et al. | |
| 2004/0024211 A1 | 2/2004 | Boyce et al. | |
| 2004/0030285 A1 | 2/2004 | Lavi et al. | |
| 2004/0069044 A1 | 4/2004 | Lavi et al. | |
| 2004/0138612 A1 | 7/2004 | Shermer et al. | |
| 2004/0176728 A1 | 9/2004 | Fisher et al. | |
| 2004/0210197 A1 | 10/2004 | Conway | |
| 2005/0177117 A1 | 8/2005 | Crocker et al. | |
| 2006/0018941 A1 | 1/2006 | Matsuda et al. | |
| 2006/0122577 A1 | 6/2006 | Poulsen et al. | |
| 2006/0163506 A1 | 7/2006 | Cook et al. | |
| 2007/0078415 A1 | 4/2007 | Jakobsen | |
| 2007/0088252 A1 | 4/2007 | Pestotnik et al. | |
| 2007/0244457 A1 | 10/2007 | Fangrow | |
| 2007/0255262 A1 | 11/2007 | Haase | |
| 2007/0276320 A1 | 11/2007 | Wall et al. | |
| 2007/0282269 A1 | 12/2007 | Carter | |
| 2008/0058718 A1* | 3/2008 | Adams | A61M 5/14248 604/132 |
| 2008/0154200 A1 | 6/2008 | Lesch | |
| 2008/0215015 A1 | 9/2008 | Cindrich et al. | |
| 2008/0312600 A1 | 12/2008 | Krulevitch et al. | |
| 2009/0118669 A1 | 5/2009 | Bendek et al. | |
| 2009/0145509 A1 | 6/2009 | Baker et al. | |
| 2009/0163866 A1 | 6/2009 | Hines et al. | |
| 2009/0214364 A1* | 8/2009 | Wex | A61M 5/14244 417/474 |
| 2009/0247953 A1 | 10/2009 | Yeshurun et al. | |
| 2009/0281497 A1 | 11/2009 | Kamen et al. | |
| 2009/0326457 A1 | 12/2009 | O'Connor | |
| 2010/0030181 A1 | 2/2010 | Helle et al. | |
| 2010/0036318 A1 | 2/2010 | Raday et al. | |
| 2010/0087786 A1 | 4/2010 | Zinger | |
| 2010/0130958 A1 | 5/2010 | Kang et al. | |
| 2010/0137802 A1 | 6/2010 | Yodfat et al. | |
| 2010/0170473 A1 | 7/2010 | Genosar | |
| 2010/0185177 A1 | 7/2010 | Gillum | |
| 2010/0185178 A1 | 7/2010 | Sharp et al. | |
| 2010/0198182 A1 | 8/2010 | Lanigan et al. | |
| 2010/0312220 A1 | 12/2010 | Kalitzki | |
| 2010/0331773 A1 | 12/2010 | Frederiksen et al. | |
| 2011/0004183 A1 | 1/2011 | Carrez et al. | |
| 2011/0021905 A1 | 1/2011 | Patrick et al. | |
| 2011/0023997 A1 | 2/2011 | Scholten et al. | |
| 2011/0060280 A1* | 3/2011 | Caffey | A61M 5/14248 604/151 |
| 2011/0098657 A1 | 4/2011 | Jennings | |
| 2011/0108158 A1 | 5/2011 | Huwiler et al. | |
| 2011/0184348 A1 | 7/2011 | Bates et al. | |
| 2011/0186177 A1 | 8/2011 | Lanier, Jr. et al. | |
| 2011/0213299 A1 | 9/2011 | Cronenberg | |
| 2011/0301548 A1 | 12/2011 | Young | |
| 2011/0306929 A1 | 12/2011 | Levesque et al. | |
| 2012/0041367 A1 | 2/2012 | Cronenberg et al. | |
| 2012/0067429 A1 | 3/2012 | Mosler et al. | |
| 2012/0089085 A1 | 4/2012 | Foshee et al. | |
| 2012/0150139 A1 | 6/2012 | Studer | |
| 2012/0157965 A1 | 6/2012 | Wotton et al. | |
| 2012/0184902 A1 | 7/2012 | Jeter et al. | |
| 2012/0265166 A1* | 10/2012 | Yodfat | A61M 5/1413 604/506 |
| 2013/0018326 A1 | 1/2013 | Hooven | |
| 2013/0110049 A1* | 5/2013 | Cronenberg | A61M 5/14248 604/180 |
| 2013/0116624 A1 | 5/2013 | Plunnecke | |
| 2013/0218123 A1 | 8/2013 | Beiriger | |
| 2013/0261558 A1 | 10/2013 | Hourmand et al. | |
| 2013/0296807 A1 | 11/2013 | Lintern | |
| 2013/0313156 A1 | 11/2013 | Duncan | |
| 2013/0324884 A1 | 12/2013 | Hadvary | |
| 2014/0008366 A1 | 1/2014 | Genosar | |
| 2014/0048174 A1 | 2/2014 | Lanigan et al. | |
| 2015/0105720 A1 | 4/2015 | Montalvo et al. | |
| 2015/0141922 A1 | 5/2015 | Tefera | |
| 2015/0148772 A1 | 5/2015 | Tefera | |
| 2015/0246176 A1 | 9/2015 | Navarro et al. | |
| 2015/0273139 A1 | 10/2015 | Hadvary et al. | |
| 2015/0283031 A1 | 10/2015 | Lanier, Jr. et al. | |
| 2015/0352276 A1 | 12/2015 | Yodfat et al. | |
| 2016/0129178 A1 | 5/2016 | Askarinya et al. | |
| 2016/0129203 A1 | 5/2016 | Chong et al. | |
| 2016/0263312 A1 | 9/2016 | Junod et al. | |

FOREIGN PATENT DOCUMENTS

| | | |
|---|---|---|
| EP | 709104 | 3/1998 |
| EP | 706805 | 11/1998 |
| EP | 988868 | 3/2000 |
| EP | 1070230 | 1/2001 |
| EP | 1039947 | 6/2001 |
| EP | 636035 | 10/2001 |
| EP | 1501573 | 11/2003 |
| EP | 2155289 | 2/2010 |
| EP | 2155295 | 2/2010 |
| EP | 2298388 A1 | 3/2011 |
| EP | 2298389 A1 | 3/2011 |
| EP | 2519287 | 7/2011 |
| EP | 2438938 A1 | 4/2012 |
| EP | 2627374 | 4/2012 |
| EP | 2659921 | 11/2013 |
| EP | 2908881 | 4/2014 |
| EP | 2803348 | 11/2014 |
| EP | 2337543 | 12/2014 |
| EP | 2907535 A2 | 8/2015 |
| EP | 2699286 | 8/2016 |
| EP | 2731652 | 8/2016 |
| EP | 3062837 | 9/2016 |
| GB | 2091853 A | 8/1982 |
| JP | 09-201396 A | 8/1997 |
| WO | WO 95/16480 | 6/1995 |
| WO | WO 96/39213 A1 | 12/1996 |
| WO | WO 97/41917 | 11/1997 |
| WO | WO 99/30759 | 6/1999 |
| WO | WO 00/29049 | 5/2000 |
| WO | WO 00/29049 A1 | 5/2000 |
| WO | WO 01/76684 | 10/2001 |
| WO | WO 03/089821 A1 | 10/2003 |
| WO | WO 03/090509 A2 | 11/2003 |
| WO | WO 2004/024211 A2 | 3/2004 |

(56) References Cited

FOREIGN PATENT DOCUMENTS

| | | |
|---|---|---|
| WO | WO2004024211 A2 | 3/2004 |
| WO | WO2004024211 A3 | 3/2004 |
| WO | WO 2004/052428 A1 | 6/2004 |
| WO | WO 2005/079440 A2 | 9/2005 |
| WO | WO 2005/079440 A3 | 9/2005 |
| WO | WO 2005/079441 A2 | 9/2005 |
| WO | WO2005/079441 A3 | 9/2005 |
| WO | WO 2008/139458 | 11/2008 |
| WO | WO 2008/139459 | 11/2008 |
| WO | WO 2008/139460 | 11/2008 |
| WO | WO 2011/082265 A1 | 7/2011 |
| WO | WO 2011-123659 A1 | 10/2011 |
| WO | WO 2012/049080 A2 | 4/2012 |
| WO | WO 2014/060965 A2 | 4/2014 |
| WO | WO 2014/204894 | 12/2014 |
| WO | WO 2015-15379 | 2/2015 |
| WO | WO 2015-28458 | 3/2015 |
| WO | WO 2015/057483 A1 | 4/2015 |
| WO | WO 2015/63576 | 5/2015 |
| WO | WO 2015/094945 | 6/2015 |
| WO | WO 2015/094950 A1 | 6/2015 |
| WO | WO 2015/164649 | 10/2015 |

OTHER PUBLICATIONS

PCT Written Opinion of the International Searching Authority for PCT/US2013/059359 dated Dec. 18, 2013.

PCT International Preliminary Report on Patentability for PCT/US2013/059359 dated Mar. 24, 2015.

European Supplementary Search Report and European Search Opinion for EP Application No. 11763443.6 (published as EP 2552518) dated Apr. 4, 2014.

Notification of Transmittal of the International Search Report, International Search Report and Written Opinion for PCT/US2011/030748 dated Jun. 6, 2011.

PCT International Preliminary Report on Patentability and Written Opinion for PCT/US2011/030748 dated Oct. 11, 2012.

International Search Report for International Application No. PCT/US2014/042627 dated May 29, 2015.

Written Opinion of the International Searching Authority for International Application No. PCT/US2014/042627 dated May 29, 2015.

One page Brochure of Dosi-Fuser Elastomeric Infusion Pumps by Omni Medical Supply, Inc.

Multi-page Brochure of Freedom60 Syringe Infusion System by RMS Medical Products.

Two-page Brouchure of Neria-Multi Infusion Sets by Unomedical Company.

* cited by examiner

VIAL TRANSFER AND INJECTION APPARATUS AND METHOD

This application claims priority to and the benefit of U.S. Provisional Patent Application No. 61/979,816, filed Apr. 15, 2014, and U.S. Provisional Patent Application No. 61/836,266, filed Jun. 18, 2013, both of which are hereby incorporated by reference in their entirety.

The present subject matter generally relates to devices and methods for administering the contents of vials and more specifically to a disposable one-time use apparatus and method that transfers and mixes the contents of one or more vials into a disposable injection device for administration into a subject such as a human being.

BACKGROUND

Vials are one of the preferred container closure systems used by the pharmaceutical industry due to their extensive clinical history and record of long term stability with a wide variety of drugs. Pharmaceutical drugs including biologics are often first commercially introduced in standard containers such as vials. Additionally the industry has made a significant investment in capital equipment for aseptic vial filling. However, vials require the transfer of the contained drug from the vial to an injection device for delivery to the patient. New container closure systems such as prefilled syringes and cartridges have been introduced that allow direct transfer of the drug from the syringe or cartridge to the patient. Injection devices such as autoinjection devices and pens have been developed to utilize these newer forms of container closure. Because of uncertainty about long-term drug stability, and the extensive manufacturing resources already in place, devices that incorporate standard container closure systems such as vials, prefilled syringes or cartridges are greatly preferred by the pharmaceutical industry over devices that require a custom form of drug containment.

However, vials, prefilled syringes and cartridges are not necessarily the optimum containers for a drug delivery device. This is especially true in the case of delivery devices that deliver relatively high volumes of drugs (2-20 cc) or high viscosity (over 15 cP). Vials, prefilled syringes and cartridges are almost exclusively cylinders made of glass, which imposes design constraints on forces and geometries. Typical syringes and autoinjection devices are limited on the viscosities of drug that can be delivered as well as by the forces that can be applied to the glass container closure systems. New injection devices have been developed including pumps for the delivery of insulin that use custom container closures, but these systems are very expensive, cannot generate high forces or pressures and typically reusable and/or refillable.

Due to factors including stability and time to market, pharmaceutical drugs including biologics are often initially marketed in a lyophilized or powder form or in concentrated liquid form. Such drugs packaged in vials in both liquid and powder formulations can require significant preparation prior to administration. To facilitate the administration of liquid formulations in vials, drugs in vials are often packaged with an empty syringe and multiple needles for aspiration out of the vials and injection into the patient. In the case of powder formulations, an additional diluent or solution vial may be provided to allow for reconstituting the powder drug into solution available for injection.

The risks associated with the preparation and administration of these drug forms are significant. They include the potential for needle stick injury during the reconstitution and administration process as well as errors with improper mixing and inaccurate dose volume or concentration delivered. This presents a real challenge for both trained caregivers and patients preparing and receiving the medication. Similar issues of risk can also apply to the transfer of ready-to-inject drug that must be transferred from a vial to an injection device.

This transfer involves removal of the drug from the vial, measurement of the proper dose, and injection into the patient using a syringe. Incomplete transfer of the full volume of the vial necessitates overfilling of the vial by some 25-30% and the associated waste. Contamination of the drug with non-sterile ambient air that is injected into the vial, or improper sterile technique can cause contamination of the injectable drug.

Accordingly, there continues to exist a need for new and/or improved apparatus and methods for transfer, mixing and injection of drugs from a source vial or vials to a subject.

DESCRIPTION

The description below is for purposes of illustration only and not limitation. The present subject matter may be employed in a variety of apparatus, systems and methods not depicted below.

SUMMARY

The present subject matter is directed, in part, to disposable, one-time-use apparatus and methods for preferably automatically mixing and/or transferring, upon user initiation, the injectable contents of one or more standard vials into an injection device and preferably simultaneously pressurizing the injection device for subsequent automated injection into a subject. The contents of the vial(s) may be any suitable injectable, and for purposes of this description and claims, "injectable" includes without limitation drugs of any type, therapeutic or diagnostic, antibiotics, biologics, sedatives, sterile water and other injectable materials, either alone or in combination with one or more other injectables, and whether or not requiring reconstitution or concentration adjustment or other processing before injection. Although various features of the present subject matter may be described in the context of reconstituting a powder drug for injection, the apparatus and method disclosed here are not limited to that particular application and may be employed with liquid injectables that are ready for injection and only need to be transferred from the vial to the injection device. Furthermore, the apparatus and method disclosed may be employed to injectables that do not require reconstitution or concentration adjustment but which are to be mixed before injection (such as where two liquid drugs are to be mixed for a combination drug therapy), and/or other injection applications.

The apparatus and method described herein may be of any suitable detailed configuration, but is preferably configured to transfer the contents of a vial into an injection device. Also, the apparatus may be configured to mix or process the contents of vials requiring reconstitution or concentration adjustment during the transfer process. Also, the apparatus may be configured to allow the user to select a dose volume for injection and may further include a lock-out feature that requires such a selection before communication of the contents of the vial with the apparatus is permitted or transfer or mixing or other processing is initiated. The apparatus may further be configured to filter the contents for removal of particulate or drug particles before transfer into the injection device, and may include a sterile filter for filtering any displacement air vented into the vial or vials. The device may also include a lockout to prevent the user from removing the injection device prior to drug transfer or activating the injection device until the device has been removed from the transfer apparatus.

The present subject matter may include a vial holder configured to hold one or more vials in a predefined relationship for cooperation with the transfer apparatus. For example, the vial holder may be configured to include one receiving zone or cavity for a single vial (such as a liquid drug containing vial). Alternatively, the vial holder may be configured to include a first vial-receiving zone or cavity for a first vial (such as a lyophilized drug containing vial) and a second vial receiving zone or cavity for a second vial (such as a diluent containing vial). The vial holder may contain the vial(s) in a predefined relationship for mounting to or otherwise cooperating with the transfer apparatus for accessing the vial contents and processing them if needed (e.g., mixing them to reconstitute the drug). The vial holder may be configured to only accept a diluent containing vial in one of the receiving zones and only accept a powder vial in the other receiving zone as to prevent mix up of the vials in the wrong position. The vial holder may include a removable cover that is configured for attachment over the vial caps that cover the vial access members, such that removal of the cover simultaneously removes the vial caps and exposes the vial access members for connection to the transfer apparatus or prior antiseptic swabbing if needed. If the vial caps have been maintained suitably sterile by the cover, the swabbing may not be necessary although still preferred out of an abundance of caution. Alternatively, the vial holder with vials installed may be mounted to the transfer apparatus with the vial caps already removed. The sterility of the vial stoppers and vial access members may be maintained through the life of the product, eliminating the need for the user to remove the vial caps and swab the vial tops.

The present subject matter includes an injection device of any suitable detailed construction, but injection devices that are particularly useful in combination with the apparatus here are described in U.S. patent application Ser. No. 61/326,492 filed Apr. 21, 2010; U.S. patent application Ser. No. 13/637,756, filed Sep. 27, 2012; and U.S. patent application No. 61/704,922, filed Sep. 24, 2012, all of which are hereby incorporated by reference herein. As can be seen in those applications, the illustrated injection devices employ an expandable member, such as a balloon, to automatically expel or inject the drug when activated by the user. Long term storage of a drug in such a pressurized member presents design and manufacturing challenges, and a particularly beneficial aspect of one embodiment of the present subject matter is that the injection device may remain unpressurized (e.g., the balloon unfilled and unexpanded and in a low energy state) and the injectable remains in its standard original vial or vials for enhanced shelf life until an injection is required. At that time, the injectable is preferably automatically transferred by the transfer apparatus from the vial or vials into the injection device (with any associated mixing, diluting or other processing as required), with the transfer apparatus simultaneously charging the injection device (e.g., expanding and pressurizing the expandable member or balloon by introducing the injectable there into under pressure) so that the injection device is ready for automated injection into a subject upon user activation. In this application, the injectable is in the injection device only for a very limited amount of time, such as seconds or minutes, and shelf life concerns and design or material constraints for long term drug storage are reduced.

In accordance with another aspect of the present subject matter, which may be employed in any suitable injection device, the expandable member (such as a balloon) may be elongated and configured to progressively collapse from one end to another during injection. The specific configuration may vary, but arrangement of the elongated expandable member in a generally flat spiral or helical configuration allows for the expandable member to be of substantial length and volume in a relatively compact arrangement that can be applied to and retained on the skin of a subject during injection. The injection device may also have a viewing window that allows the user to view the expandable member and identify the general status of the injection by the amount of collapse and/or the expandable member or the viewing window may be graduated by appropriate markings so that the user can determine the amount of injection that has occurred.

Although the vial holder, transfer apparatus and injection device, and their methods of use are separate aspects of the present subject matter that have their own utility and may be separately claimed, they may also be configured and claimed in various combinations or sub combinations, such as transfer apparatus and injection device in combination or the vial holder, transfer apparatus and injection device in combination and/or the methods of using such.

BRIEF DESCRIPTION OF DRAWINGS

Examples of the subject matter of this patent application are shown for purposes of illustration only, and not limitation, in the attached drawings, of which.

DETAILED DESCRIPTION

Figure 1:
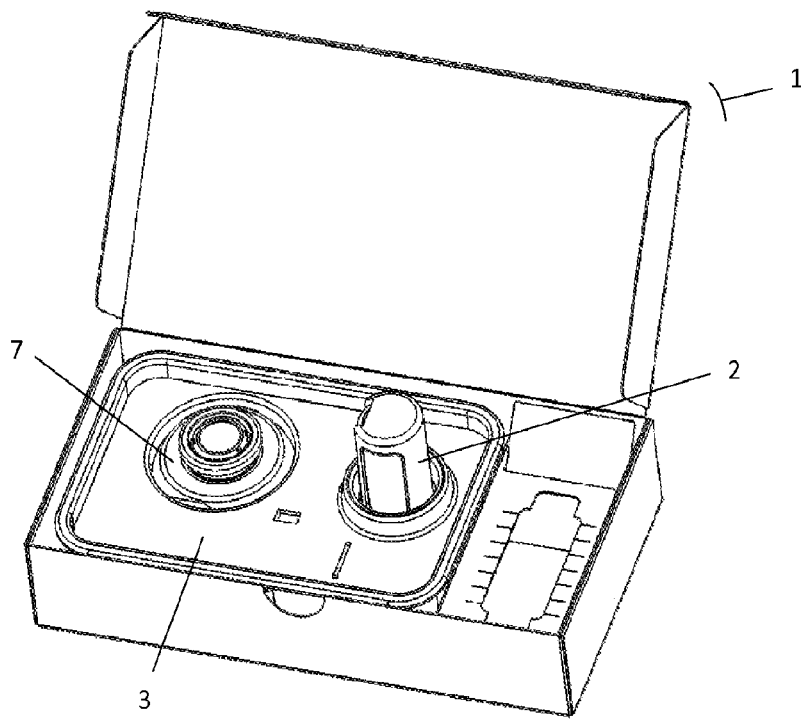
FIG. 1 is a perspective view of a single-vial system including the single vial holder, transfer apparatus and injection device system embodying the present subject matter.
Figure 2:
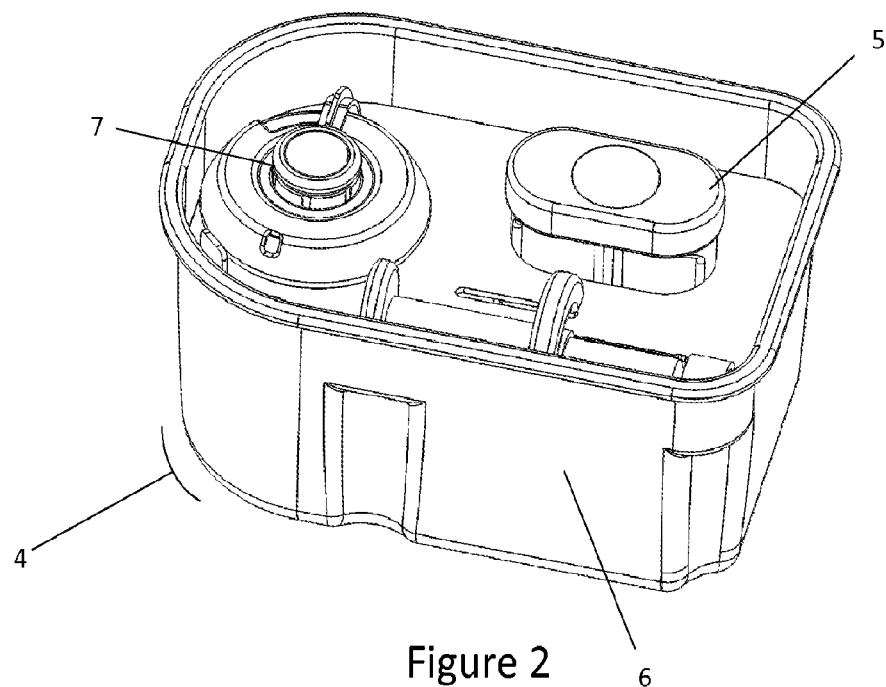
FIG. 2 is a perspective view of a dual vial system including the dual vial holder, transfer apparatus and injection device system embodying the present subject matter.

Referring to FIGS. 1 and 2, as set forth in more detail below, the disposable, one-time use, single vial transfer and injection system 1 shown in FIG. 1 may comprise a single vial holder 2, transfer apparatus 3 and injection device 7. A disposable, one-time use, dual vial mixing, transfer and injection system 4 shown in FIG. 2 may comprise a dual vial holder 5, transfer apparatus 6 and injection device 7. As mentioned earlier, each of these aspects has separate utility and may be claimed separately and/or in combination or sub-combination.

Figure 3:
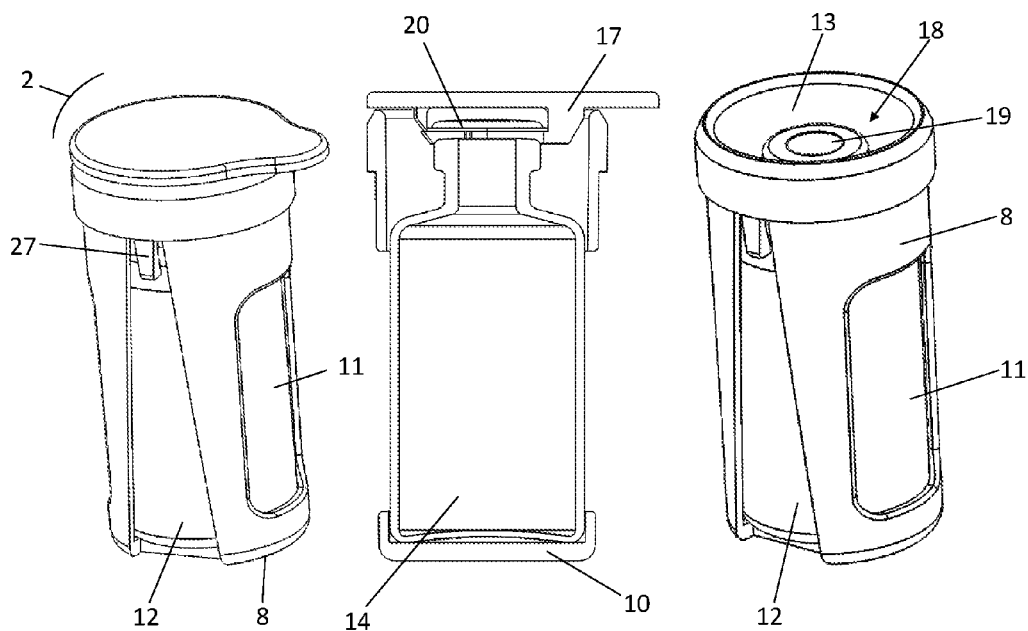
FIG. 3 includes a perspective view of a single vial holder with the removable top included, a cross-section of the single vial holder with removable top included and a perspective view of the single vial holder with the removable top and vial cap removed.
Figure 4:
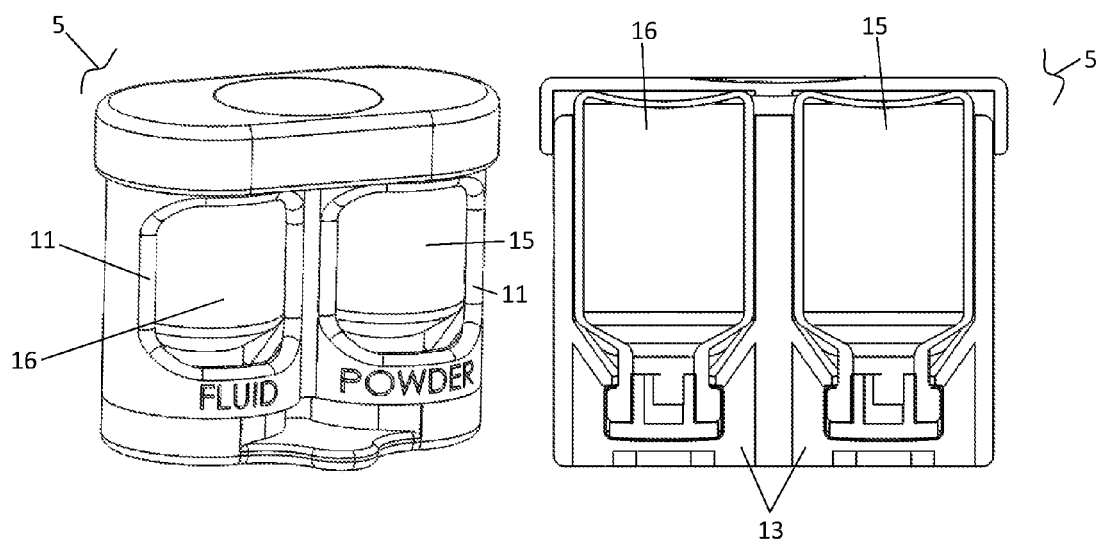
FIG. 4 includes a perspective view with removable top included and a cross-section of the dual vial holder with removable top and vial caps removed.

Referring to FIGS. 3 and 4, the single vial holder 2 shown includes a housing 8 that includes a side wall 9, end wall 10 and apertures or viewing windows 11. Alternatively the vial holder 2 material may be transparent to allow for visualization of the contents of the vial 12. The housing 8 is shaped to define at least one or two or more vial-receiving cavities 13 or zones for securely holding a vial 12 in each zone 13 as shown in FIG. 4. The cavities 13 in the vial holder 5 may be sized for receiving standard injectable vial 12 of different sizes such as from 1 to 30 ml. The vial 12 may be of the same size or different sizes and may contain any desired injectable 14. In the dual vial holder 5 illustrated in FIG. 4, the vials may include one vial of powdered, lyophilized or liquid drug 15 and one vial of liquid or diluent 16. The vial holder 5 may have the vials prepackaged and assembled therein by, for example, a drug manufacturer, or the vials may be inserted into the vial holder 5 by the end user or by a medical professional such as a pharmacist or nurse. The vial holder 5 may have appropriate markings and/or features to only allow for the assembly of certain vials in certain cavities 13. For example, the powdered drug vial 15 may be inserted into a specific cavity 13 of the vial holder 5 and diluent vial 16 in another cavity 13 of the vial holder 5. The apertures or viewing windows 11 in the vial holder 5 allow for direct visualization of the contents 14 of the vials.

Referring to FIGS. 3 and 4, as a further alternative, the vial holder 5 may be an assembly of individual vial holders 2, each of which holds a single vial 12. For example, the injectable manufacturer may preassemble a vial 12 in an individual vial holder 2 which can then be joined with the vial holder 2 of another vial 12, if needed, at the time of injection. For example, a drug manufacturer may provide a lyophilized drug 15 in its own vial holder 2 and the diluent 16, such as sterile water or saline, in a separate vial holder 2. The user or medical professional can then, as needed, join the individual vial holders 2 to form the vial holder assembly 5 for connection to the transfer apparatus 6 shown in FIG. 2.

Referring back to FIG. 3, the vial holder 2 may include a removable cover 17 that normally covers and protects the end of the vial 18 during shipping and storage. Typical standard commercial vials 12 include a pierceable septum 19 located in the vial neck for accessing the vial contents 14, which is covered by a removable vial cap or closure 20. The removable cover 17 may be configured to engage the vial cap 20 so that removal of the cover simultaneously removes vial cap 20 and exposes the vial septum 19 for accessing the contents 14 after any antiseptic swabbing of the septum 19 that may be deemed necessary by the user. The vial holder 2 may recess the vial 12 therein such that after the vial cap 20 is removed by the cover 17, the pierceable septums 19 are recessed within the vial holder 2 to reduce the chance of contamination by the user prior to insertion of the vial holder 2 into the transfer apparatus 3 as shown in FIG. 1. This system is applicable to both single vial holders 2 and dual vial holders 5.

Referring to FIG. 3, the vial holder 2 may include interlocks 27 to prevent the vial 12 from being removed once the vial 12 is inserted into the vial holder 2. This helps prevent the vial 12 from falling out or being inadvertently removed during handling.

Figure 5:
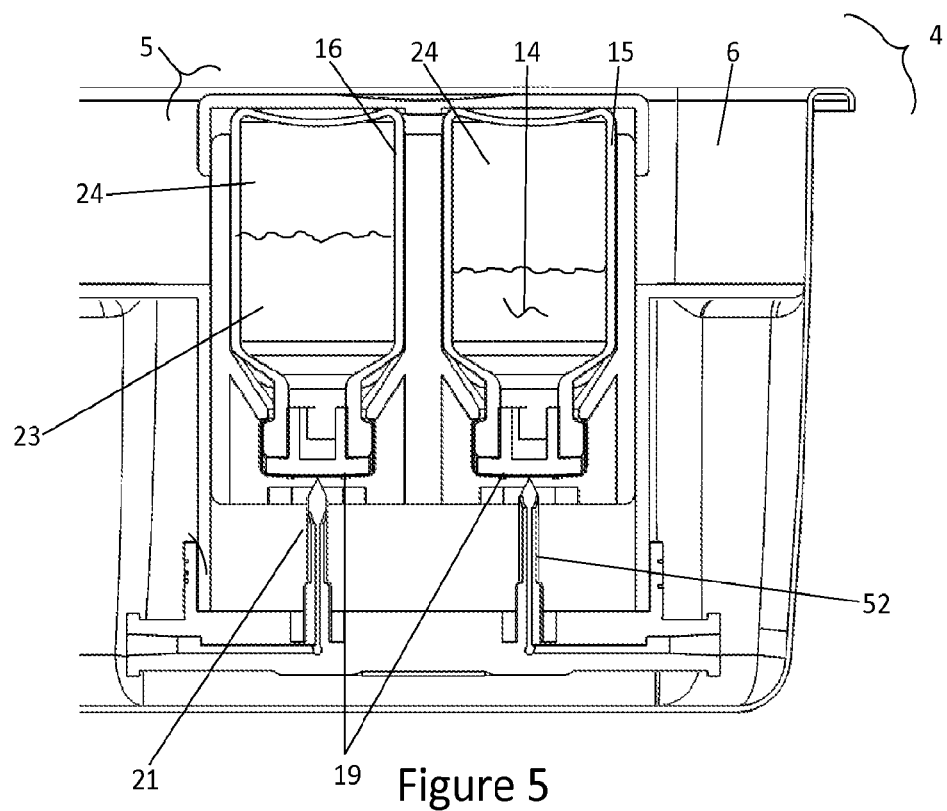
FIG. 5 is a cross-section of FIG. 2 in the area of the vial holder showing the position of the vial access members relative to the septums of the vials.

Referring to FIG. 5, the vial holder 5 may be assembled to the transfer apparatus 6 with the vial caps removed and the vials 15, 16 installed into the vial holder 5 by the device manufacturer. The exposed vial septums 19 are held in close proximity to the vial access members 21, 52 prior to activation. This configuration provides convenience by eliminating the need for the user to remove the vial caps, swab the vial tops 19 and assemble the vial holder 5 to the transfer apparatus 6 prior to use of the system 4.

Figure 6:
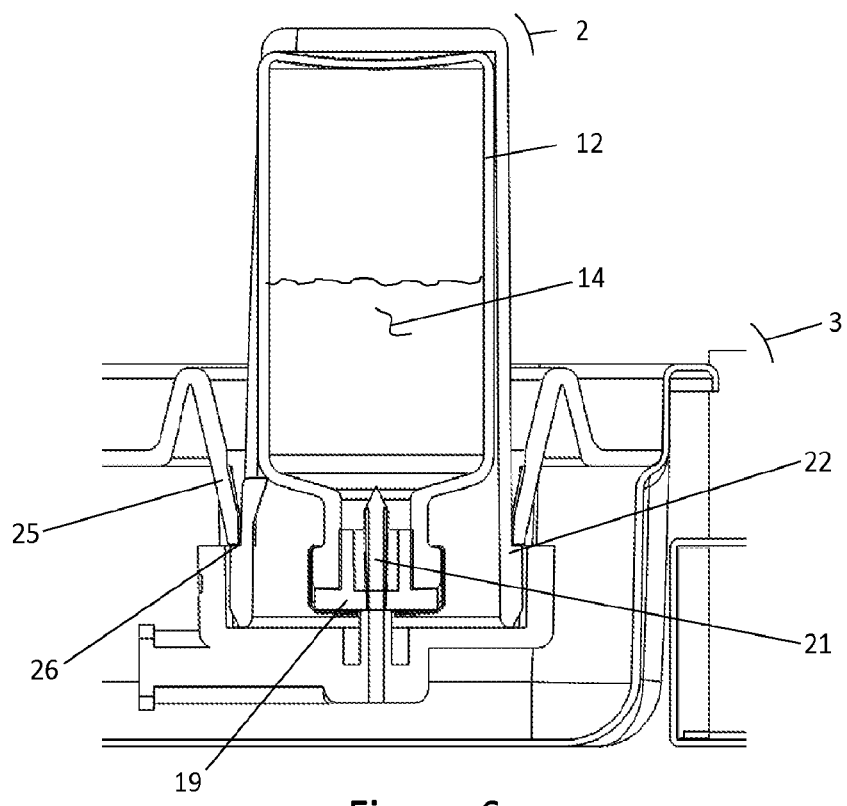
FIG. 6 is a cross-section of FIG. 1 in the area of the vial holder showing the vial access member pierced through the septum of the vial.

Referring to FIG. 6, the vial holder 2 may be packaged separately from the transfer apparatus 3. In this case, the user would remove the vial cap with the removable cover 17, swab the vial top 19 (if necessary) and assemble the vial holder 2 into the transfer apparatus 3. As shown in FIG. 6, the vial holder 2 may include lock-out features 22 that interact with the transfer apparatus 3 to prevent the vial holder 2 from being inadvertently pulled out of the transfer apparatus 3 after activation by the user.

Referring to FIG. 5, the vial holder 5 preferably is assembled to the transfer apparatus 6 to configure the vials 15, 16 upside down in a vertical position. This allows any liquid 23 in the vials to be in direct communication with the vial access members 21, 52 after insertion of the vial holder 5. This also forces the air 24 to the top of the vial in this orientation. To encourage the septums 19 to remain uncontaminated after removal of the vial caps and before insertion of the vial holder 5, the exposed vial septums 19 may be recessed into the vial holder 5 to prevent inadvertent contact as shown in FIG. 4. This configuration is applicable to single vial holder and dual vial holder configurations.

Referring to FIG. 6, the vial holder 2 preferably is mechanically configured with insertion features 25 in the transfer apparatus 3 to actuate like an on/off switch, i.e., to only have two states, open and closed such as a light switch. This may prevent the user from pushing the vial holder 2 into the transfer apparatus 3 half way and not allowing the vial access member 21 to pierce the septum 19 and allow communication between the contents 14 of the vial 12 and the transfer apparatus 3. Additionally, the vial holder 2 may interface with an interlock 26 in the transfer apparatus 3 to lock the vial holder 2 in the closed position after full insertion of the vial holder 2 to prevent the vial holder 2 from being removed from the transfer apparatus 3 after insertion.

Figure 7:
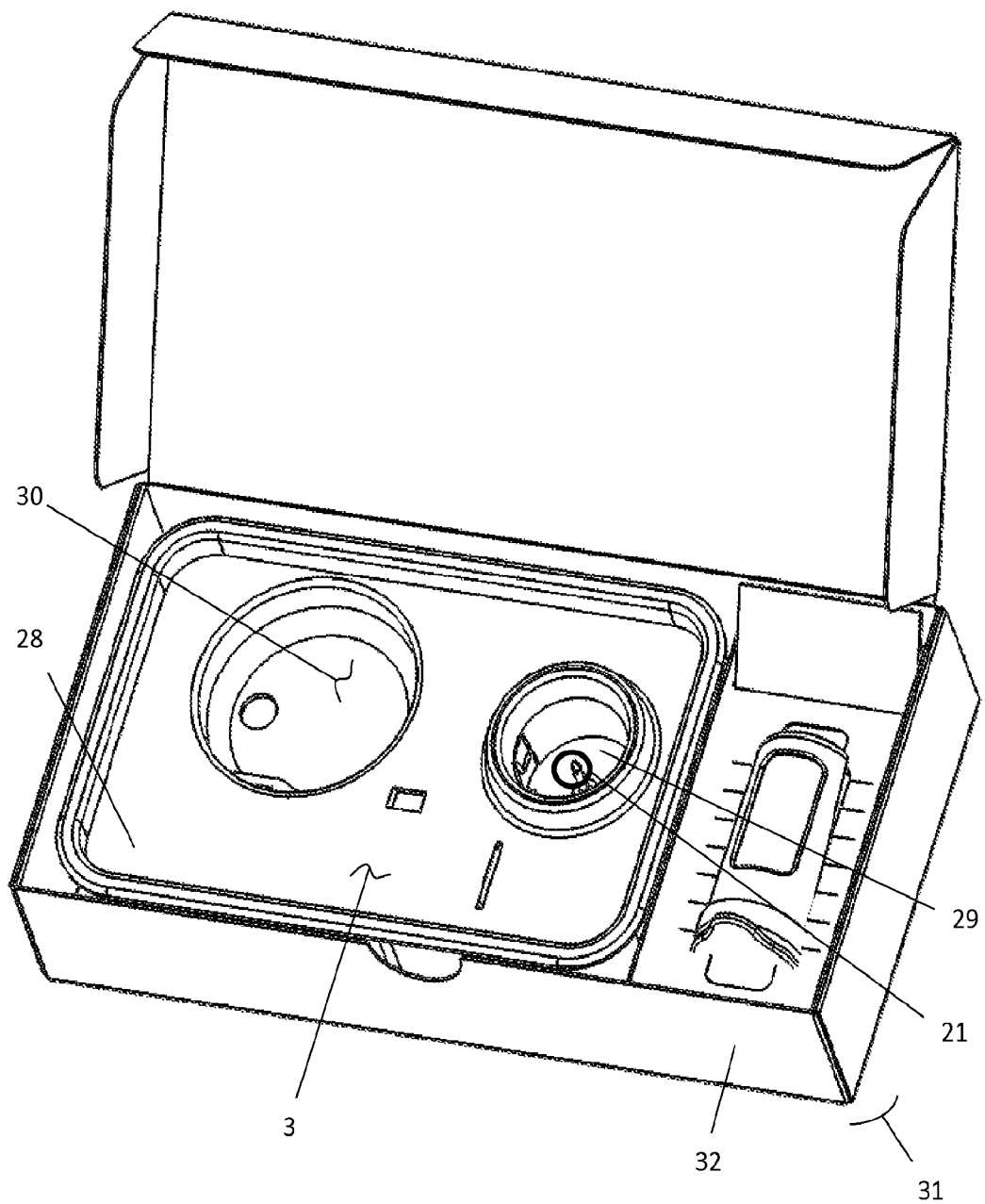
FIG. 7 is a perspective view of the transfer apparatus shown in FIG. 1 showing the vial holder and injection device receiving areas.

Referring to FIG. 7, the transfer apparatus 3 comprises an outer housing 28 and defines a vial holder docking area or first receiving station 29 and an injection device docking station or second receiving station 30 (for removable injection devices). In the illustrated structure, the vial holder docking station 29 and injection device docking station 30 are at opposite ends of the transfer apparatus housing 28.

Referring to FIG. 7, the transfer apparatus 3 may have an outer housing 28 that is integrated into the packaging 31 of the system. The outer packaging 31 may essentially form the bottom and side walls of the transfer apparatus outer housing 28. All of the operational steps in using the system up to the point of removal of the injection device may occur in this packaging 31. This may provide cost reduction and increase ease of use for the user. Additionally, incorporating the entire transfer apparatus 3 into the packaging 31 eliminates the possible user error that could occur if the user was required to remove the transfer apparatus 3 from the package 31. The packaging 31 could include a plastic tub or tray that contains the system. Furthermore, the packaging 31 could include everything within a shipping carton 32 that houses the entire system.

Figure 8:
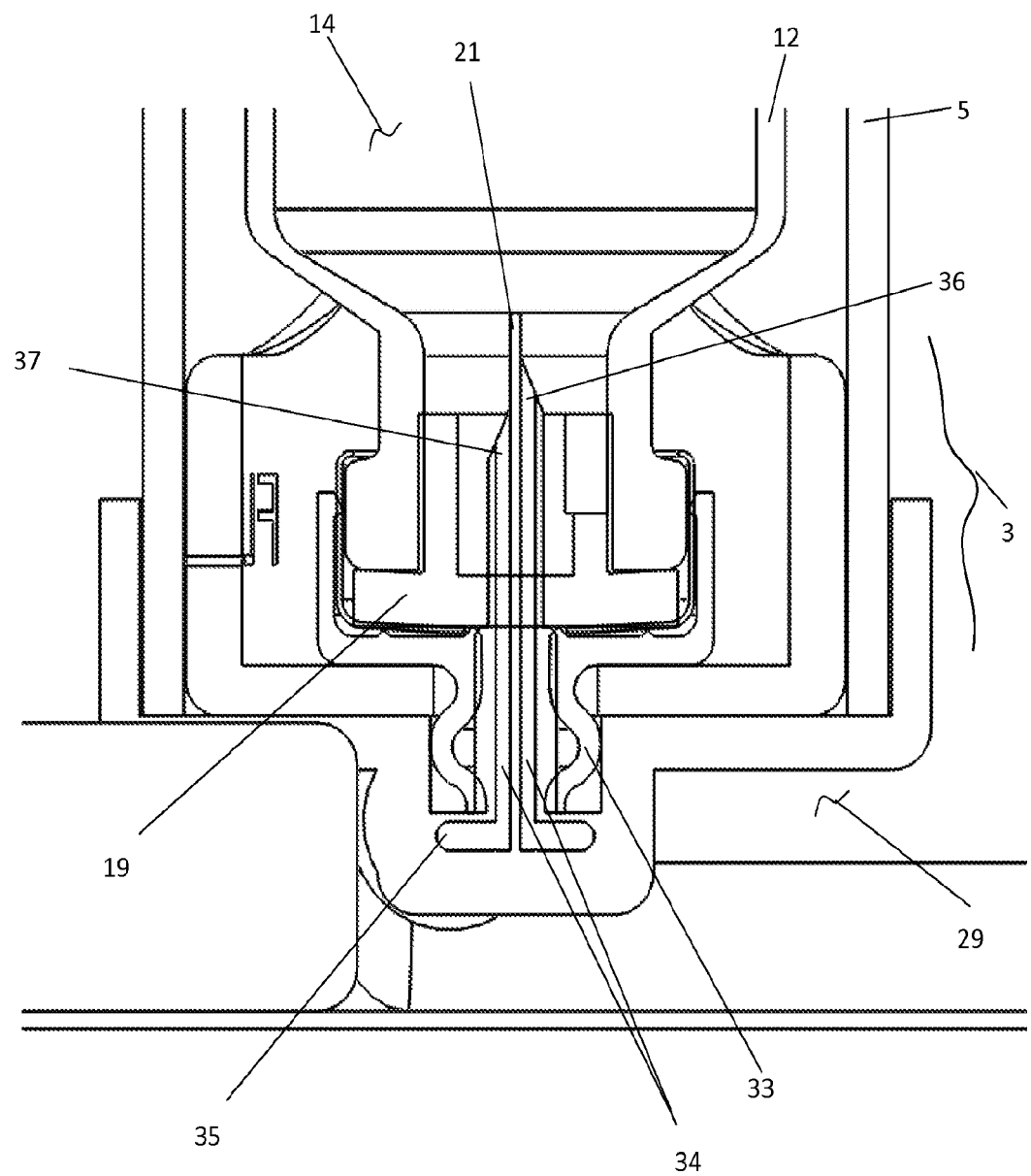
FIG. 8 is a close up of FIG. 5 illustrating the vial access member piercing the septum of the vial with the collapsible vial access member shield.

Referring to FIG. 7, the transfer apparatus 3 comprises a vial holder docking area 29 that may include elongated a vial access member or piercing member 21. This access member or piercing member 21 could be configured as pointed or blunt cannulas or needles. Referring to FIG. 8, the vial holder 5 with attached vial 12 is shown inserted into the vial docking station 29 and the vial access member 21 piercing the vial septum 19 allowing access to the contents 14 of the vial 12. The vial access member 21 may include a collapsible seal 33 to maintain sterility of the vial access member 21 and fluid path prior to activation. The collapsible seal 33 may also attach and seal on the outside of the vial 12 relative to the vial access member 21 to maintain sterility prior to activation.

Referring to FIG. 8, the vial access member 21 of the transfer apparatus 3 may comprise of multi-lumen tubes 34 to communicate with the internal fluid pathways 35 of the transfer apparatus 3. The vial access member 21 preferably comprises one inlet tube 36 allowing air or fluid to enter the vial 12 and one outlet tube 37 allowing for air or fluid to exit the vial 12. These inlet 36 and outlet 37 tubes may be separate and distinct and communicate with different fluid pathways in the transfer apparatus 3. Because of the vertical orientation of the vial 12 in the upside-down position, the lumen openings 38 in the vial access member 21 can be oriented so the inlet tube opening 36 is above the output tube opening 37. This orientation allows for introduction of pressurized air or liquid through the upper inlet tube 36 and output of the vial contents 14 through the lower output tube 37. Further, the outlet opening 37 may be positioned near the bottom of the vial 12, adjacent to the septum 19 to encourage the entire contents 14 of the vial 12 to enter the outlet port 37 and be removed from the vial 12.

Figure 9:
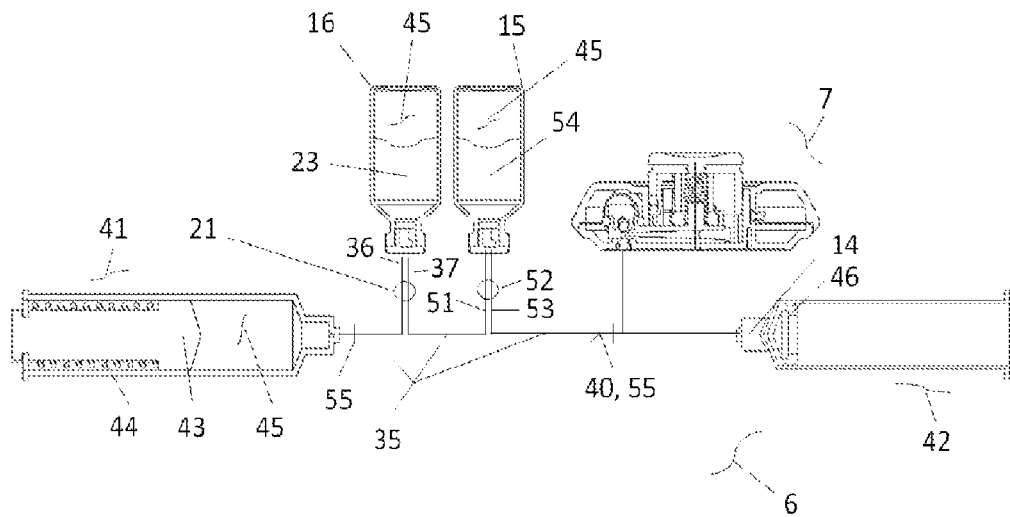
FIG. 9 is a schematic of the dual vial transfer system in FIG. 2 with a first vial, a second vial, a transfer apparatus with a first and second variable pressure chambers and injection device including the fluid pathways.
Figure 10:
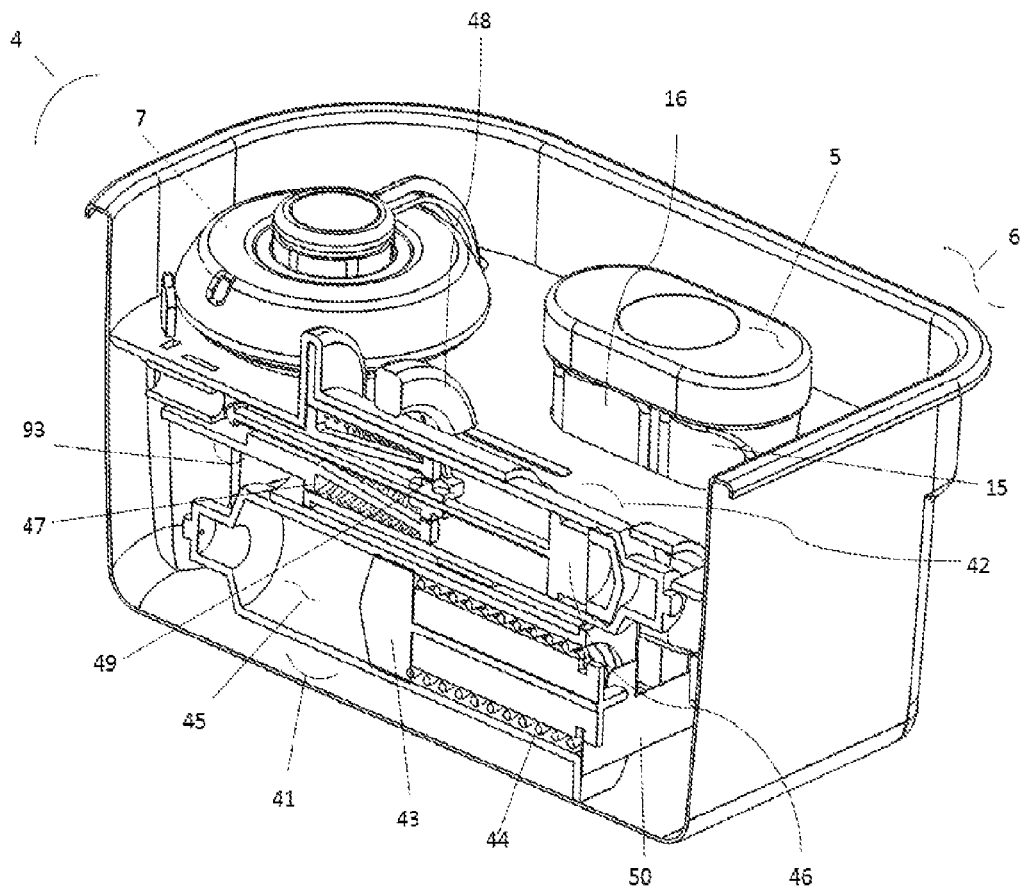
FIG. 10 is a cross-section of FIG. 2 in a pre-fire position.

Referring to FIGS. 9 and 10, the transfer apparatus 6 is configured to carry out all of the necessary steps to transfer and reconstitute (if necessary) injectable 14 contained within the vials 15,16 and transfer the mixture to the injection device 7 preferably automatically after user initiation of the process. The transfer apparatus 6 is configured and preferably includes a propulsion system or systems, such as electrically (e.g., battery powered) or mechanically (e.g., spring loaded) actuated pumps, to direct diluent from the diluent vial 16 into the injectable powder vial 15 and to direct the injectable 14 through the transfer apparatus 6 into the injection device 7.

Referring to FIGS. 9 and 10, the transfer apparatus 6 may also include an array of internal fluid pathways 35, as required to perform any transfer, reconstitution, mixing, dilution or other processing of the injectable 14 and transferring it from the vials 15, 16 in the vial holder 5 to the injection device 7. The fluid pathways 35 may include flexible or rigid conduits or tubes. These fluid pathways 35 may also include check valves, filters, flow restrictors or other means 40 to direct the drug from the vials 15, 16 through transfer apparatus 6, into the injection device 7.

Referring to FIGS. 9 and 10, the transfer apparatus 6 may include variable volume pressure chambers or cylinders that have movable spring-loaded pistons therein and directly communicate with the internal fluid pathways 35. The chamber capacity for each variable volume chamber may be defined by chamber diameter and location of the piston within the chamber. The first pressure chamber 41 in transfer apparatus 6 may preferably have an initial volume set by the manufacturer in the range of 1 to 30 milliliters. The initial contents of the first pressure chamber 41 may preferably include air 45. The piston 43 may be driven by a compression spring 44 in the first pressure chamber 41 whose volume is defined and set by the manufacturer. The spring-loaded piston 43 may be of adequate size and configuration to produce 1 to 50 psi of static air pressure in the first pressure chamber 41. The volume of air 45 will depend on the diameter of the chamber 41 and stroke position of the piston 43 during operation. This pressure will depend on the relative volume of air 45 displaced by the piston 43 and the force exerted by the spring 44. In other words, the force exerted by the spring 44 multiplied by the area of the piston 43 inside the chamber 41 will determine the static pressure within the chamber 41. The force exerted by the spring 44 at its solid height or the beginning of the stroke may be much higher than the force exerted by the spring 44 at end of its travel. The spring 44 may be appropriately sized to control the rate at which air 45 is expelled out of the pressure chamber 41 and thus the speed of the fluid transfer in the transfer apparatus 6. The first pressure chamber 41 is preferably configured to expel all of the air 45 out of the first pressure chamber 41. Alternatively, a flow restrictor 55 in the output path 35 of the pressure chamber 41 could be used to control the rate at which air 45 is expelled out of the pressure chamber 41.

Referring to FIGS. 9 and 10, the chamber volume for the second pressure chamber 42 may be set by the manufacturer. Alternatively, the filled chamber volume for the second pressure chamber 42 may be set by the user at time of use using a dose selector or volume controller 48 in the range of 0.5 to 30 milliliters. The spring-loaded piston 46 in the second pressure chamber 42 may be of adequate size and configuration to produce 1 to 200 psi of pressure in the second pressure chamber 42. A dose selector or volume controller 48 permits the user to select a prescribed dosage to be injected by the injection device 7 by setting the filled volume of chamber 42. The dose selector 48 may be of any suitable configuration. The dose selector 48 may be directly coupled to the pressure plunger assembly chamber 93 which is moveable inside the pressure chamber 42. A trigger 49 within the pressure plunger assembly 93 releases the piston 46 in the second pressure chamber 42 once the piston has reached a position corresponding to the filled volume setting. The user selects the desired dosage positions in the second pressure chamber 42 by moving the dose selector 48 which positions the pressure chamber plunger assembly 93 to define a filled chamber volume equal to the desired injection dosage. Alternatively, the position of the pressure plunger assembly 93 may already be set by the manufacture corresponding to the delivery dose and the user operates the device without making a dose adjustment.

Referring to FIGS. 9 and 10, the transfer apparatus 6 for a dual vial system 4 that provides for mixing and transfer includes a vial holder 5 with a first vial 16 and second vial 15, a first variable volume pressure chamber 41, a second variable volume dose pressure chamber 42, fluid pathways 35, and check valves 40 to direct air from the first pressure chamber 41 into the first vial 16 and the contents 23 of the first vial 16 into the second vial 15 and the resulting mixture 14 in the second vial 15 into the second pressure chamber 42 which is then transferred into the injection device 7.

Referring to FIG. 8, upon complete insertion of the vial holder 5 into the transfer apparatus 6 and the subsequent introduction of the vial access members 21 through the septums 19 and into the vial chambers 12 by the user allows for the release of the pressure chamber trigger 50 shown in FIG. 10.

Referring to FIGS. 9 and 10, release of the trigger 50 then releases the first pressure chamber spring 44 allowing the advance of the first pressure chamber piston 43 in the first pressure chamber 41 causing the air 45 in the first pressure chamber 41 to be forced through the inlet tube 36 of the first vial access member 21 and into the first vial 16 through internal passage ways 35 in the transfer apparatus 6. As more air 45 is forced out of the first pressure chamber 41 and into the first vial 16 through the inlet tube 36, the air 45 rises to the top of the first vial 16 due to its vertical orientation within the vial holder 5. The increasing air pressure in the first vial 16 causes the fluid 23 in the vial 16 to be expelled through the outlet tube 37 of the first vial access member 21 and through the inlet tube 51 of the second vial access member 52. The fluid 23 from the first vial 16 entering the second vial 15 mixes with the contents 54 of the second vial 15 containing the liquid or powdered drug and exits though the outlet tube 53 of the second vial access member 52 and into the second pressure chamber 42. In the same manner within the reconstitution configuration, the advancing plunger 43 in the first pressure chamber 41 continues to push a first fluid 23 then air 45 mixture through the first vial 16 into the second vial 15. The increasing air pressure in the top of the second vial 15 causes the reconstituted mixture 14 in the bottom of the second vial 15 to be expelled out into the second pressure chamber 42. A 'popoff' or check valve 40 or other type of valve may be present on the outlet tube 53 of the second vial access member 52 to encourage all of the contents 23 of the first vial 16 to enter the second vial 15 before the contents 14 of the second vial 15 are expelled out into the second pressure chamber 42. The valve would not open until the pressure corresponding to the plunger 43 pushing substantially all the air 45 out of the first pressure chamber 41. This ensures that the contents 54 of the second vial 15 may be thoroughly mixed with the contents 23 of the first vial 16 before the mixture 14 exits the second vial 15 and into the second pressure chamber 42. Alternatively, a flow restrictor 55 may be used in the fluid pathway 35 to delay the transfer and increase the mixing time.

Referring to FIGS. 9 and 10, injectable drug 14 flows from the second vial 15 after reconstitution, into the second pressure chamber 42, filling the chamber 42 to the extent permitted by the piston 46 position as selected using the dose indicator 48 by the user or manufacturer, which corresponds to the desired dosage. When the desired volume of the second pressure chamber 42 has been achieved, the second pressure chamber trigger 49 releases the spring 47 and forces the piston 46 forward, expelling the selected dosage of injectable drug 14 under pressure into the injection device 7. Calibration of the dose volume shown on the dose selector 48 and the actual dose received by the user may be required to account for fluid loss in the internal pathways 35 of the transfer apparatus 6. The injection device 7 is now full and ready to remove from the transfer apparatus 6.

Figure 11:
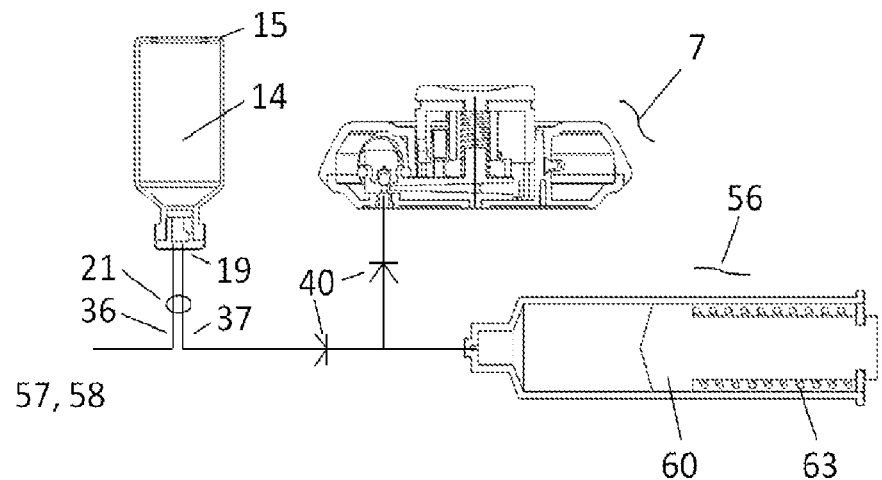
FIG. 11 is a schematic of the single vial transfer system in FIG. 1 with a drug vial, a transfer apparatus with a first variable pressure chamber and injection device including the fluid pathways.
Figure 12:
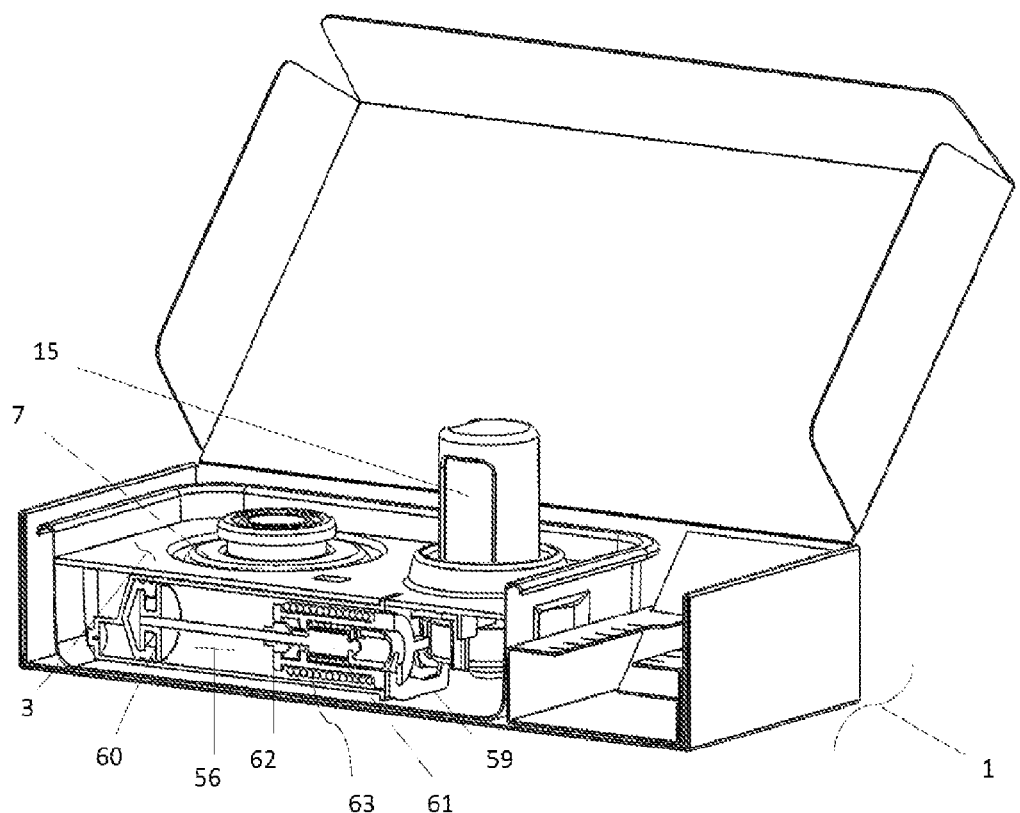
FIG. 12 is a cross-section of FIG. 1.

Referring to FIGS. 11 and 12, an alternative transfer apparatus 3 within a single vial system 1 that does not perform mixing but only transfers fluid 14 from a single vial 15 to the injection device 7 is provided. This alternative transfer apparatus 3 includes a vial holder 2 with single vial 15, a variable volume pressure chamber 56, fluid pathways 35, and check valves 40 to direct the contents 14 from the vial 15 into the injection device 7. The inlet tube 36 of the vial access member 21 is vented to the environment 57 to allow air 58 to enter the vial 1. The outlet tube 37 of the vial access member 21 is connected to the pressure chamber 56.

Referring to FIGS. 11 and 12, the full insertion of the vial holder 2 into the transfer apparatus 3 by the user causes the introduction of the vial access member 21 through the septum 19 of the vial 15 to access the contents 14 of the vial 15. This also triggers the release of the pressure chamber trigger 59. The pressure release trigger 59 releases the plunger 60 within the pressure chamber 56 connected to a withdraw spring 61. The withdraw spring 61 forces the plunger 60 to retract and withdraw fluid 14 from the vial 15 and fill the pressure chamber 56. A specified amount of fluid 14 withdrawn by the chamber 56 could be set by the manufacturer by limiting the retraction of the plunger 60. Additionally, the chamber 56 can be configured to withdraw all of the fluid 14 from the vial 15 by retracting the plunger 60 to its full travel. Once the plunger 60 reaches a set position within the pressure chamber 56, it interacts with a dispense trigger 62 that releases a dispense spring 63 to force the liquid 14 out of the pressure chamber 56 into the injection device 7. Check valves 40 could be employed to prevent fluid 14 from going back into the vial 15.

Figure 13:
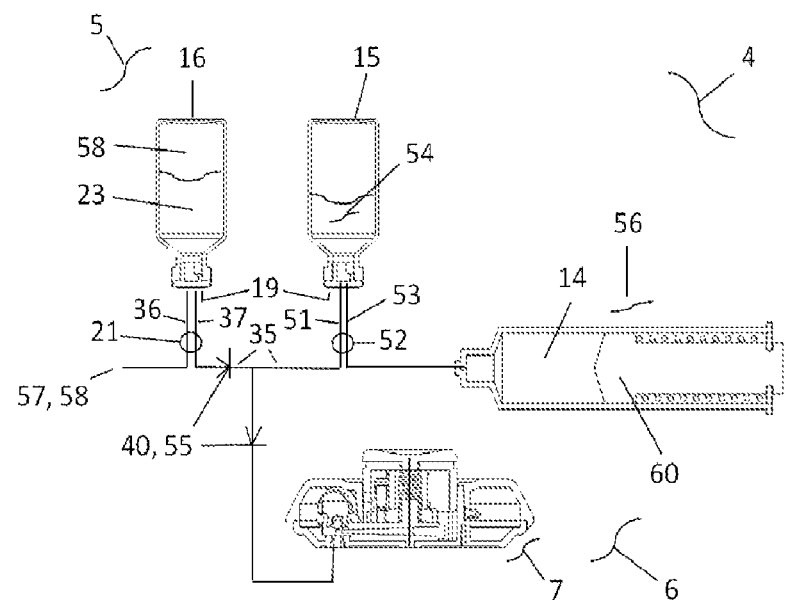
FIG. 13 is a schematic of an alternative embodiment for the dual vial transfer system in FIG. 2 with a first vial, a second vial, a transfer apparatus with a first pressure chamber and injection device including the fluid pathways.

Referring to FIG. 13, an alternative transfer apparatus 6 for a dual vial system 4 that provides for mixing and transfer includes a vial holder 5 with a first vial 16 and second vial 15, a variable volume pressure chamber 56, fluid pathways 35, and check valves 40 to direct the contents 23 of the first vial 16 into the second vial 15 and the resulting mixture 14 into the pressure chamber 56. This mixture 14 is then transferred back into the second vial 15 and then transferred into the injection device 7. In this embodiment, the inlet tube 36 of the first vial access member 21 is vented to the environment 57 to allow air 58 to enter the vial 16. The outlet tube 37 of the first vial access member 21 is connected to the inlet tube 51 of the second vial access member 52. The outlet tube 53 of the second vial access member 52 is connected to the variable volume pressure chamber 56. A fluid pathway 35 includes check valves 40 that are located between the first vial access member 21, the second vial access member 52 and the injection device 7.

Referring to FIG. 13, the full insertion of the vial holder 5 into the transfer apparatus 6 by the user causes the introduction of the vial access members 21, 52 through the septums 19 of the vials 15, 16 to access the contents 23, 54 of each vial 15, 16. This also triggers the release of the pressure chamber trigger. The pressure chamber trigger releases the plunger 60 within the pressure chamber 56 connected to a withdraw spring. The withdraw spring forces the plunger 60 to retract and withdraw fluid 23 from the first vial 16 which fills the second vial 15. This filling also results in mixing of the fluid 23 from the first vial 16 and the contents 54 of the second vial 15. The resulting mixture 14 from the second vial 15 fills the pressure chamber 56 until all of the fluid 23 is removed from the first vial 16. The rate at which the first vial 16 fills the second vial 15 can be controlled with check valves 40 or flow restrictors 55. The amount of fluid 23 withdrawn from the first vial 16 can be set in the chamber 56 by the manufacturer. Once the plunger 60 in the chamber 56 reaches a set position within the pressure chamber 56, it interacts with a dispense trigger that releases a dispense spring to force the liquid 14 out of the pressure chamber 56 back into the second vial 15. This has an advantage to allow for additional mixing of the fluid 23 from the first vial 16 and the contents 14 of the second vial 15. Once all of the fluid 14 from the chamber 56 is dispensed back to the second vial 15, the solution 14 is transferred to the injection device 7. The volume of the pressure chamber 56 could be set to be larger than the total fluid volume so that additional air 58 is drawn into chamber 56. This additional air 58 could be helpful in insuring that all of the liquid 14 is transferred into the injection device 7 that may otherwise have resided in the fluid pathways 35. Check valves 40 could be employed anywhere in the fluid pathways 35 to prevent fluid 14 from going back into the first vial 16 during transfer of the mixture 14 from the second vial 15 to the injection device 7. Flow restrictors 55 could be employed anywhere in the fluid pathway 35 to control the amount of mixing time of within the second vial 15 before transfer of the mixture 14 to the injection device 7.

Figure 14:
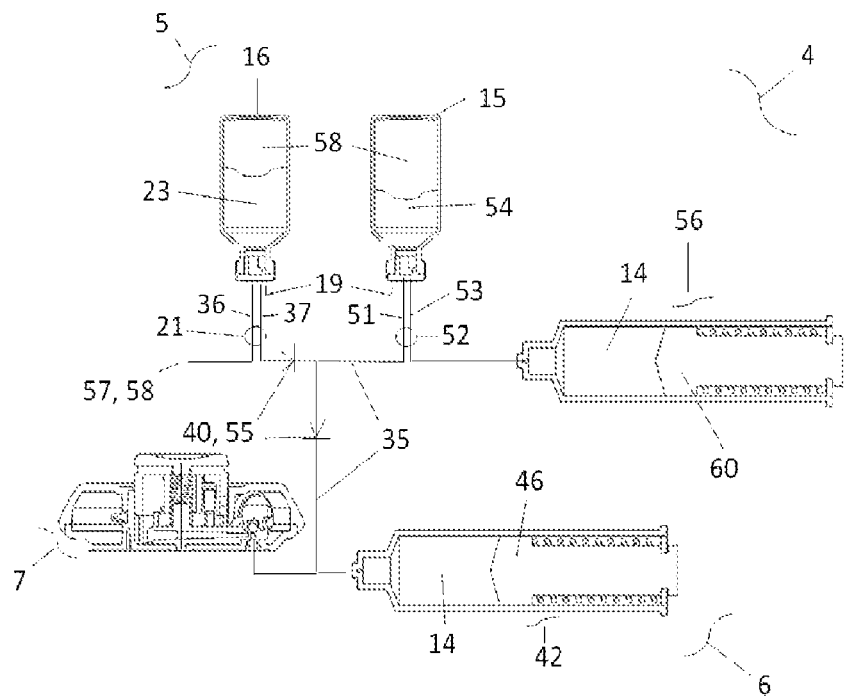
FIG. 14 is a schematic of an alternative embodiment of the dual vial transfer system in FIG. 2 with a first vial, a second vial, a transfer apparatus with a first and second variable pressure chamber and injection device including the fluid pathways.

Referring to FIG. 14, an alternative transfer apparatus 6 for a dual vial system 4 that provides for mixing and transfer includes a vial holder 5 with a first vial 16 and second vial 15, a first variable volume pressure chamber 56, a second variable volume pressure chamber 42, fluid pathways 35, and check valves 40 to direct the contents 23 of the first vial 16 into the second vial 15 and the resulting mixture 14 into the pressure chamber 56. This mixture 14 is then transferred from the first pressure chamber 56 to a second pressure chamber 42 and then transferred into the injection device 7. In this embodiment, the inlet tube 36 of the first vial access member 21 is vented to the environment 57 to allow air 58 to enter the vial 16. The outlet tube 37 of the first vial access member 21 is connected to the inlet tube 51 of the second vial access member 52. The outlet tube 53 of the second vial access member 52 is connected to the first variable volume pressure chamber 56. A fluid pathway 35 include a check valve 40 also exists between the first vial access member 21, the second vial access member 52 and the second pressure chamber 42 and the injection device 7.

Referring to FIG. 14, the full insertion of the vial holder 5 into the transfer apparatus 6 by the user causes the introduction of the vial access members 21, 52 through the septums 19 of the vials 15, 16 to access the contents 23, 54 of each vial 15, 16. This also triggers the release of the pressure chamber trigger. The pressure chamber trigger releases the plunger 60 within the pressure chamber 56 connected to a withdraw spring. The withdraw spring forces the plunger 60 to retract and withdraw fluid 23 from the first vial 16 which fills the second vial 15. This filling also results in mixing of the fluid 23 from the first vial 16 and the contents 54 of the second vial 15. The resulting mixture 14 from the second vial 15 fills the pressure chamber 56 until all of the fluid 23 is removed from the first vial 16. The rate at which the first vial 16 fills the second vial 15 can be controlled with check valves 40 or flow restrictors 55. The amount of fluid 23 withdrawn from the first vial 16 can be set in the chamber 56 by the manufacturer. Once the plunger 60 in the chamber 56 reaches a set position within the pressure chamber 56, it interacts with a dispense trigger that releases a dispense spring to force the liquid 14 out of the pressure chamber 56 back into the second vial 15. Once all of the fluid 14 from the chamber 56 is dispensed back to the second vial 15, the solution 14 is transferred into the second pressure chamber 42, filling the chamber 42 to the extent permitted by the piston 46 position as selected using the dose indicator by the user or manufacturer, which corresponds to the desired dosage. When the desired volume of the second pressure chamber 42 has been achieved, the second pressure chamber trigger releases the second pressure chamber spring and forces the piston 46 forward, expelling the selected dosage of injectable drug 14 under pressure into the injection device 7. Check valves 40 could be employed anywhere in the fluid pathway 35 to prevent fluid 14 from going back into the first vial 16 during transfer of the mixture 14 from the second vial 15 to the second pressure chamber 42 and to the injection device 7. Flow restrictors 55 could be employed anywhere in the fluid pathway 35 to control the amount of mixing time of within the second vial 15 before transfer of the mixture 14 to the second pressure chamber 42.

Figure 15:
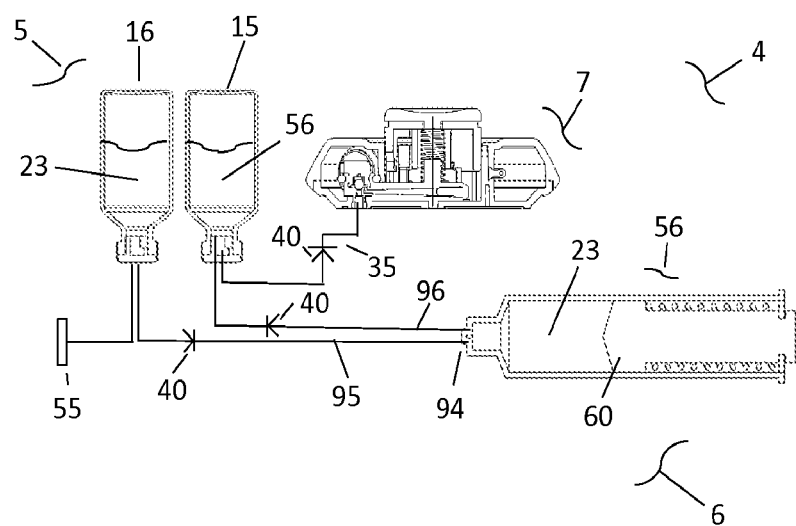
FIG. 15 is a schematic of an alternative embodiment of the dual vial transfer system in FIG. 2 with a first vial, a second vial, a transfer apparatus with a first pressure chamber, a dual lumen connector and injection device including the fluid pathways.

Referring to FIG. 15, an alternative transfer apparatus 6 for a dual vial system 4 that provides for mixing and transfer includes a vial holder 5 with a first vial 16 and second vial 15, a variable volume pressure chamber 56, a dual lumen connector 94, inlet fluid pathway 95, outlet fluid pathway 96 and check valves 40 to direct the contents 23 of the first vial 16 into the pressure chamber 56 through the inlet line 95 during retraction of the plunger 60 within the pressure chamber 56. The advancement of the plunger 60 after full retraction within the pressure chamber 56 causes the fluid contents 23 to flow from the pressure chamber 56 into the second vial 15, mix with the contents 56 of the second vial 15 and the resulting mixture 14 flows into the injection device 7. A check valve 40 in the outlet fluid pathway 96 would prevent the contents 56 of the second vial 15 from being pulled into the pressure chamber 56 during the retraction phase. A check valve 40 in the inlet fluid pathway 95 would prevent the fluid contents 23 in the pressure chamber 56 from being transferred back to the first vial 16 during advancement of the plunger 60. A check valve in the fluid pathway 35 from the second vial 15 and the injection device 7 prevents the mixture from being transferred back from the injection device 7 to the second vial 15. Flow restrictions 55 could be employed anywhere in the fluid pathways 35, 95, 96 to control the rate of fluid transfer. Alternatively, the use of the dual lumen connector 94 could also be used for a single vial transfer system 1 in the same manner to remove and advance fluid in different fluid pathways.

Figure 16:
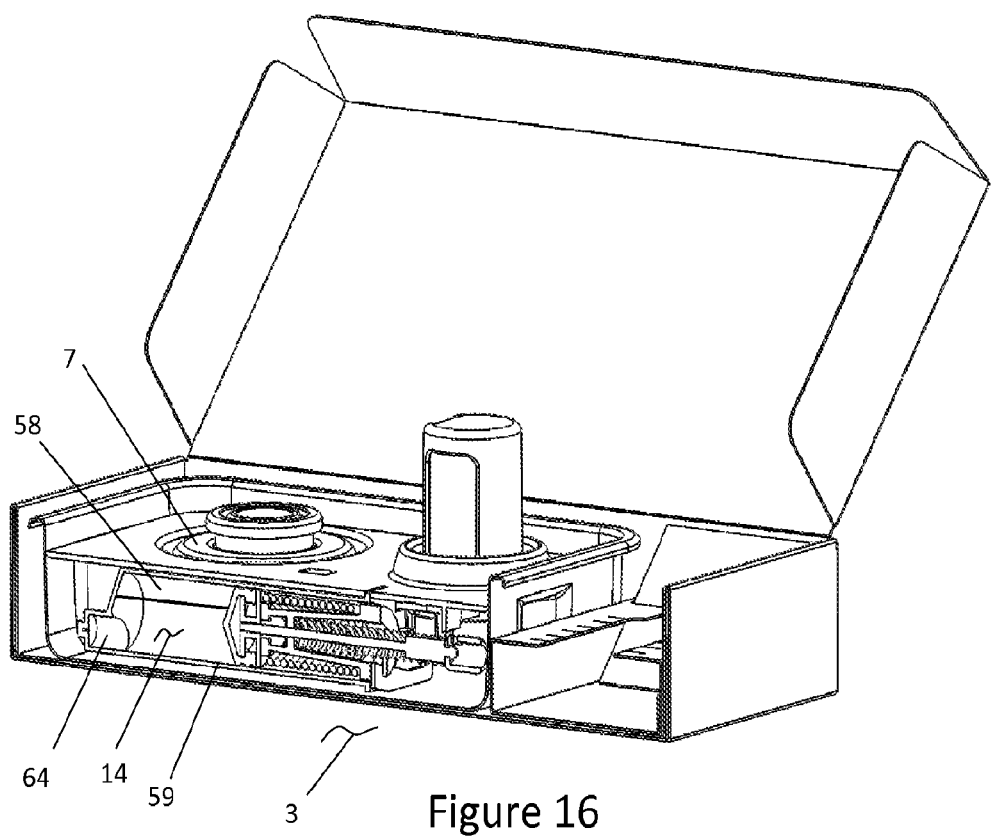
FIG. 16 is a cross-section of FIG. 1.

Referring to FIG. 16, the pressure chambers in the abovementioned embodiments may be configured with an outlet port 64 that is biased or off-center compared to a normal syringe to take advantage of gravity. When the pressure chamber 59 is filled with liquid 14 during a transfer process, there may be some air 58 that is introduced into the chamber 59 in addition to liquid 14. During the process of expelling the liquid 14 from the pressure chamber 59, it may be advantageous to control the order of when air 58 or liquid 14 is expelled from the pressure chamber 59. For example, if the outlet port 64 of the pressure chamber 59 is oriented down, during the process of expelling the liquid 14 from the pressure chamber 59, all of the liquid 14 is expelled first then the remaining air 58 is expelled last since the air bubble is oriented to the top of the pressure chamber 59. Conversely, if the outlet port 64 is oriented up, during the process of expelling the liquid 14 from the pressure chamber 59, all of the air 58 is expelled first then the remaining liquid 14 last. This has particular advantage when using hydrophobic or hydrophilic filters to remove unwanted air 58 from the lines during the transfer of liquid 14 to the injection device 7.

The transfer apparatus may employ a variety of devices or procedures to enhance mixing. For example, the transfer apparatus may inject the diluent into the drug-containing vial in a swirling manner to enhance mixing and/or may employ or introduce mixture-enhancing members such as dynamic or static mixers, e.g., mixing balls, augers or propellers, oscillating injection tubes, or the like. These techniques could be employed within the second vial or one of the syringes. Additionally, the transfer apparatus may have an intermediate chamber between the outlet tube of the second vial access member and the pressure chamber to allow for the abovementioned enhanced mixing techniques and procedures. The transfer apparatus also may be configured to move the injectable vial to induce turbulence and enhance mixing, such as by spinning the injectable vial. A flow restrictor may be used in the air or drug path to increase the transfer time to allow for greater mixing.

Figure 17:
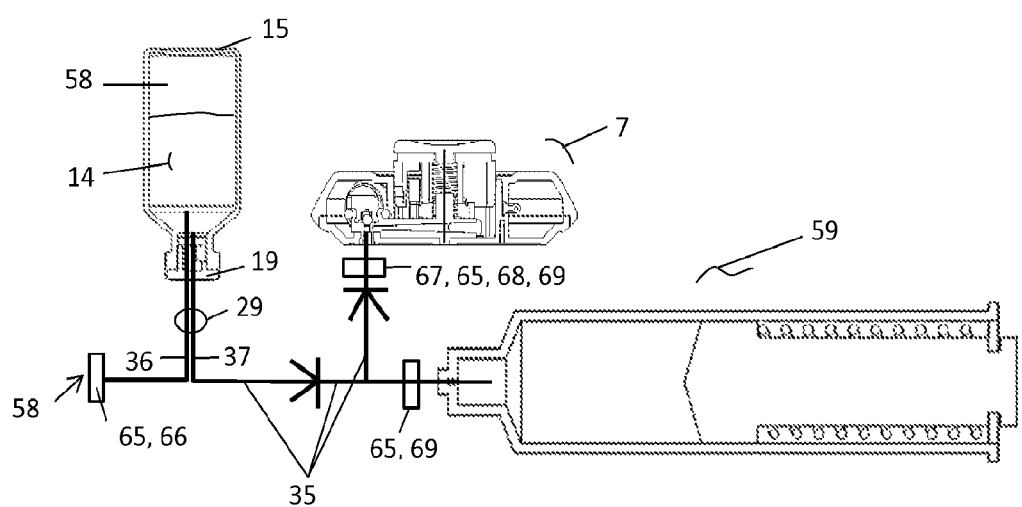
FIG. 17 is a schematic of an alternative embodiment of the single vial transfer system in FIG. 1 with a drug vial, a transfer apparatus with a first variable pressure chamber, an injection device including the fluid pathways with check valves and flow restrictors.

Referring to FIGS. 16 and 17, another optional feature of the transfer apparatus 3 is a filter 65 in the injectable fluid pathway 35 for filtering the injectable 14 to remove particulate before it is introduced into the injection device 7. The filter 65 may be a membrane, depth filter or other suitable filtration media that is of sufficiently small pore size or effective pore size to remove objectionable particulate, which may include but not be limited to undissolved injectable 14 in those situations where the injectable 14 is reconstituted by the transfer apparatus 3.

Referring to FIGS. 16 and 17, withdrawing injectable from the vial 15 may require or be enhanced by the introduction of displacement air 58 into the vial 15. In another aspect of the present subject matter, the transfer apparatus 3 may include a displacement air pathway or vent 66 that communicates with the interior of the vial(s) to allow displacement air 58 to enter the vial 15 as the injectable 14 is withdrawn. As previously discussed, the vial access member 29 for piercing the vial septum 19 may have inlet 36 and outlet 37 tubes, one for injectable 14 flowing from the vial 15 and one for displacement air 58 flowing into the vial 15. The displacement air 58 flow pathway 35 in the transfer apparatus 3 may include a sterile filter 65 such as membrane or depth filter 65 having an actual or effective pore size of about 0.22 microns or smaller for filtering the displacement air 58. Such a pore size is sufficiently small to prevent introduction of pathogens into the vial 15 with the displacement air 58, reducing the risk of contamination of the injectable 14.

Referring to FIGS. 16 and 17, the transfer apparatus 3 may include an air remover 67 in communication with injectable 14 fluid pathway 35 leading from the vial 15 to the injection device 7. Such an air remover 67 may include a bubble trap, air gap of other configuration in the injectable 14 fluid pathway 35 that removes air 58 from the injectable 14 fluid pathway 35 before it is introduced into the injection device 7. This air remover 67 may be configured with a hydrophobic filter 65 or a combination of hydrophobic 68 and hydrophilic 69 filters. A hydrophobic filter 68 would allow for the venting of air from the transfer apparatus 3 but not the passage of liquid 14. A hydrophilic filter 69 would allow the passage of liquid 14 but not the passage of particulate or air 58. The combination and position of the filter 69 in the fluid pathway 35 is preferable in removing all of the air 58 during the transfer process.

Figure 18:
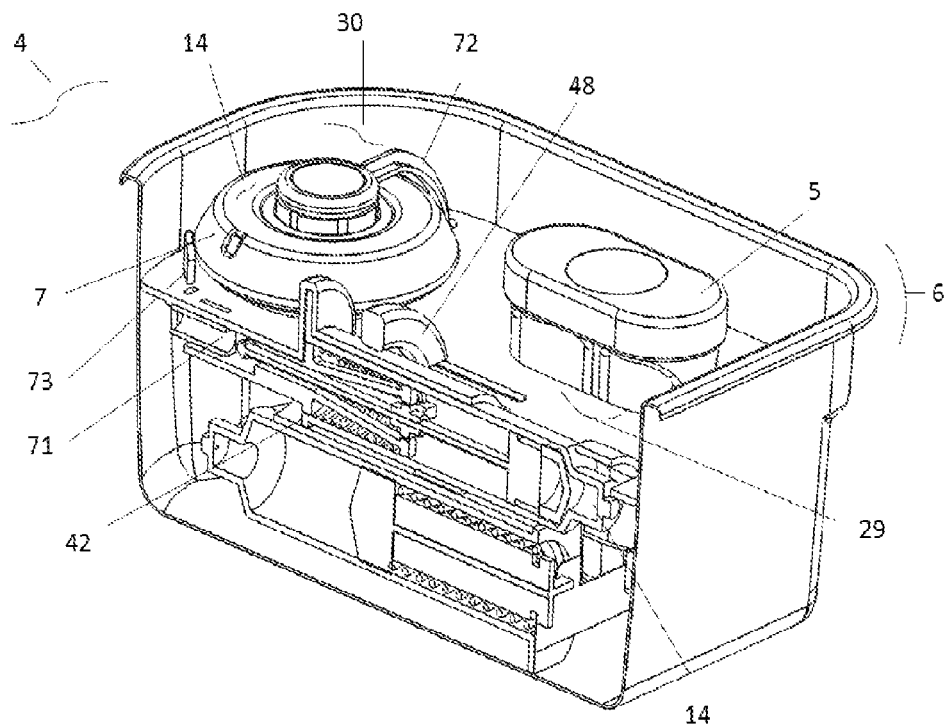
FIG. 18 is a cross-section of FIG. 2.
Figure 19:
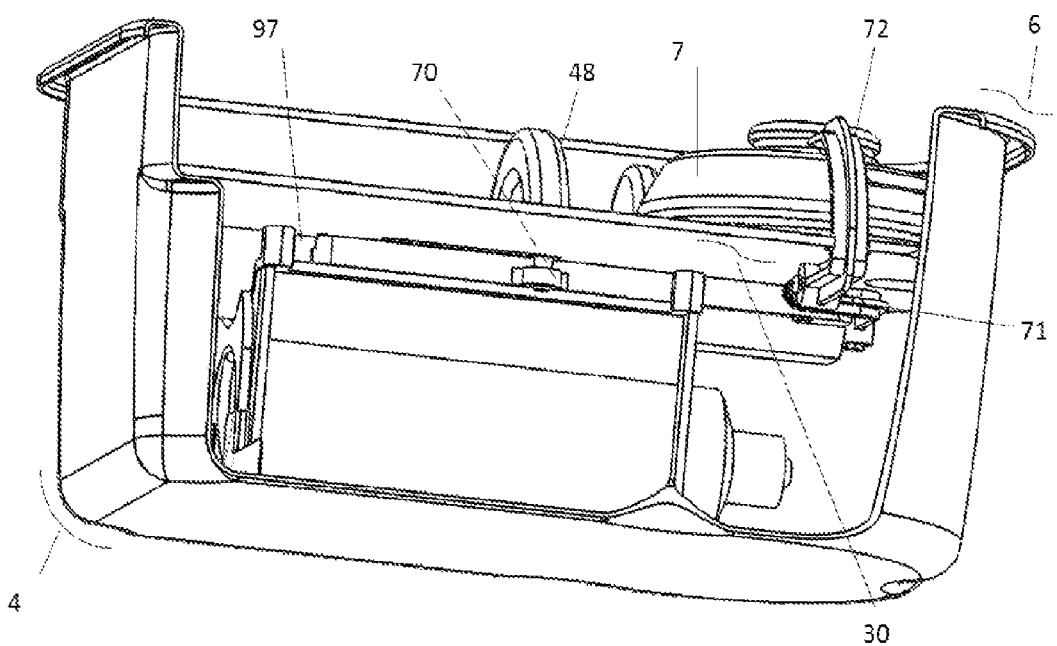
FIG. 19 is a cross-section of FIG. 2

Referring to FIGS. 18 and 19, the transfer apparatus 6 may also have additional features as well as those described above. One such feature is an interlock 70 between the dose selector 48 and the vial docking station 29. This can be, for example, a mechanical interference member 97 that prevents the user from loading vials into the docking station 29 until a dosage has been selected. Mechanically, the dosage selector 48 may be linked to an interference member 97 at the docking station 29 which normally resides in a load-prevention position to prevents insertion of the vial holder 5 into the vial holder station 29 unless moved to a load-permitting position when the dosage member 48 is moved to a dosage selected position. Of course, for administering injectable from a vial that contains a single dose of injectable or a single vial, all of which is to be injected, the transfer apparatus need not include a dose selection capability.

Referring to FIGS. 18 and 19, the transfer apparatus 6 may include an interlock 71 between the transfer apparatus 6 and the injection device 7 to prevent the injection device from being removed prior to filling and indicate when the injection device 7 is ready for removal from the transfer apparatus 6. Mechanically, a locking pin 72 may be linked to the injection device 7 to prevent removal prior to the injection device 7 being completely filled by the transfer apparatus 6. The locking pin 72 may be part of the transfer apparatus 6 and communicate with piston in the pressure chamber 42. When the pressure chamber 42 has expelled all of the injectable 14, this may mechanically trigger the locking pin 72 to move away from the injection device 7, allow for removal of the injection device 7 from the transfer apparatus 6 by the user.

Referring to FIG. 18, the transfer apparatus 6 may include an interlock between the transfer apparatus 6 and the injection device 7 to control how the injection device 7 is removed from the transfer apparatus 6. Mechanically, a flange or other protrusion 73 on the injection device 7 may mechanically interface with an undercut in the transfer apparatus 6. This configuration may allow for one-way rotation of the injection device 7 relative to the transfer apparatus 6 for removal by the user.

Referring to FIGS. 18 and 19, the transfer apparatus 6 may include a locking feature that prevents the injection device 7 from being activated while docked on the transfer apparatus 6. For example, a mechanical interference member such as a locking pin, arch or other means 72 could extend out of the transfer apparatus 6 and mechanically lock the injection device 7 at the actuator or button in the up position. Alternatively, the mechanical interference member 72 could be a shield that covers the entire injection device 7 to prevent access to the injection device 7 while on the transfer apparatus 6. The arch or shield 72 may be part of the transfer apparatus 6 and communicate with the pressure chamber 42. When the pressure chamber 42 has expelled all of the injectable 14 into the injection device 7, this may mechanically trigger the arch or shield 72 to unlock and move away from the injection device 7. This allows access to the injection device 7 and removal from the transfer apparatus 6 by the user.

Another optional feature on the transfer apparatus is a quick release filling port or access member feature between the transfer apparatus and the injection device to allow for the quick release of the injection device from the transfer apparatus and to prevent the injection device from being reattached to the transfer apparatus. After the injection device is filled and ready to remove from the transfer apparatus, the user may remove the injection device. The filling tube or access member 83 of the transfer apparatus may be spring loaded such that when the injection device is removed from the transfer apparatus, the filling tube 83 springs down into the transfer apparatus. This allows for quick release of the tube 83 from the filling port 81 of the injection device preventing inadvertent leaking of the injection device at the filling port 81. This also makes the filling tube 83 inaccessible to the user, thus preventing reattachment of the injection device onto the transfer apparatus.

Referring to FIG. 18, the injection device 7 and transfer apparatus 6 are preferably configured for removable attachment of the injection device 7. In the current embodiment, after transfer of the injectable fluid 14 from the second pressure chamber 42 within the transfer apparatus 6 into the injection device 7 and release of the interlock 71 on the transfer apparatus 6, the injection device 7 is ready to be separated from injection device docking station 30 of the transfer apparatus 6 for application to the skin of a subject. As previously mentioned, alternative embodiments described herein include the transfer of the injectable fluid from a single pressure chamber directly to the injection device.

Figure 20:
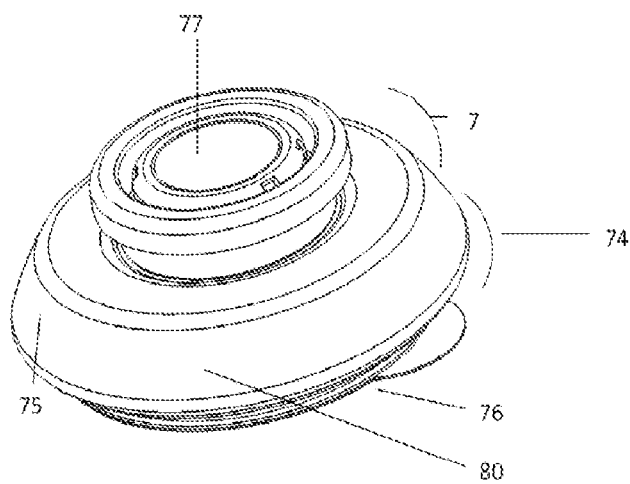
FIG. 20 is a perspective view of the injection device.

Referring to FIG. 20, the injection device 7 may be of any suitable configuration. As explained earlier, the injection device may advantageously employ one or more of the features of the injection devices described in U.S. patent application Ser. No. 61/326,492 filed Apr. 21, 2010; U.S. patent application Ser. No. 13/637,756, filed Sep. 27, 2012; and U.S. patent application No. 61/704,922, filed Sep. 24, 2012, which are all hereby incorporated by reference herein.

Figure 21:
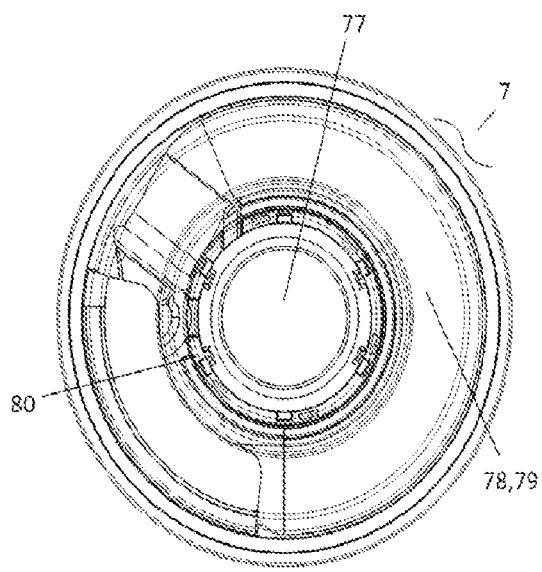
FIG. 21 is a top view of a filled injection device showing the delivery indicator in a full state.
Figure 22:
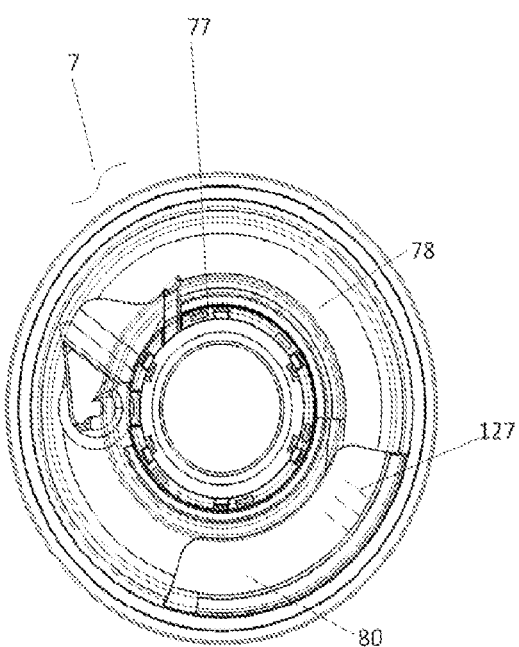
FIG. 22 is top view of a filled injection device showing the delivery indicator in an empty state.

Referring to FIGS. 20-22, the injection device 7 has a generally low-profile, disc shaped outer housing 74 with an upper surface 75 and a lower surface 76, through which an injection needle or cannula protrudes when actuated by the user. The upper surface 75 has an actuator or button 77 to start the injection and a clear section 80 of the housing 74 that allows the subject or medical professional to view the expandable member 78 to ascertain the amount of injectable fluid 79 in the device 7. For example, the user could determine whether the injection has commenced or concluded. More preferably, the expandable member 78 and/or the clear section 80 of the housing 74 may be graduated, such as by line markings 127 or the like, so that the patient or medical professional can visually determine the amount of injectable fluid 79 remaining with greater precision—such as, for example, about 50% complete or about 75% complete. In addition, the expandable member 78 may itself include or interact with a feature on the outer housing 74 to show the amount of injectable fluid 79 remaining. For example, when the injection device 7 is full of drug 79, the clear section 80 may show one color such as but not limited to green. When the injection device 7 is empty of drug 79, the clear section 80 may show a different color such as but not limited to red. In the middle of dispense, the clear section 80 could show a combination of colors.

Figure 23:
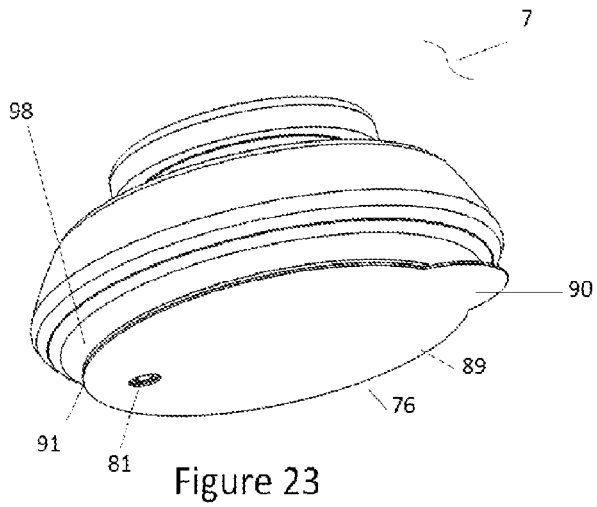
FIG. 23 is a perspective view showing the underside of the injection device with attached tape and fill port.
Figure 24:
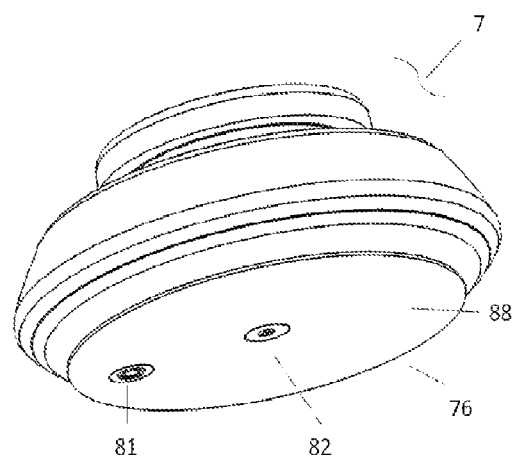
FIG. 24 is a perspective view showing the underside of the injection device with tape detached and the fill and dispense ports exposed.
Figure 25:
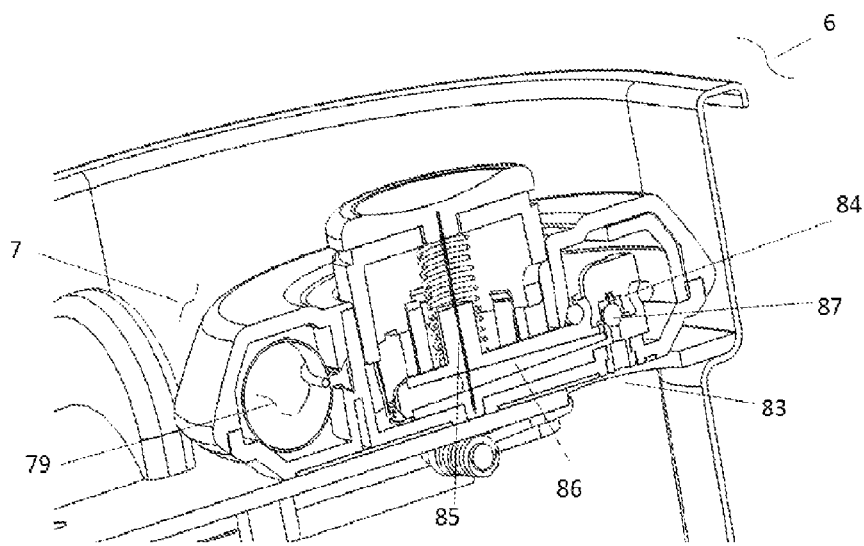
FIG. 25 is a cross-section of the injection device on the transfer apparatus.

Referring to FIGS. 23-25, the undersurface 76 of the injection device 7 includes a filling port 81 and a dispense port 82. The filling port 81 is the interface that allows the transfer apparatus filling tube 83 to transfer liquid 79 to the injection device 7. The dispense port 82 also contains an internal pathway 84 between the expelled injectable 79 from the expandable member 78 and the needle 85. The filling port 81 and dispense port 79 may be in direct fluid communication through internal pathways, such as fluid pathway 86, or they may be combined into a single port.

Referring to FIGS. 23-25, the injection device may preferably include a filling port 81 that includes a check valve 87 to prevent pressurized injectable 79 from leaking out of the injection device 7 when the injection device 7 is removed from the transfer apparatus 6 and the filling port 81 is removed from the filling tube 83.

Referring to FIGS. 23-25, the injection device 7 may also have a filling port 81 that is configured to accept the insertion of a syringe. This syringe may be configured with a luer fitting or a needle. This filling port 81 configuration allows for the manual filling of the injection device by the user. The transfer apparatus 6 may still be used but would not be required in this configuration.

Referring to FIGS. 23-25, the injection device 7 may also have a dispense port 82 that is configured to directly connect to an intravenous cannula via attached tubing or a standard needle port.

Referring to FIGS. 23-25, the undersurface 76 of the injection device 7 carries an adhesive 88 for securing the injection device 7 temporarily to the skin of a subject until the injection is complete. During removal of the injection device 7, an adhesive tape liner 89 may be removed automatically exposing an adhesive surface 88 on the undersurface 76 of the injection device 7 that may be used to adhere the injection device 7 to the patient's skin. Alternatively, the tape liner 89 may have a tab 90 that the user pulls to manually remove before adhering the injection device 7 to the skin. Alternatively this tab may be attached to the surface of the transfer device 4 so that the tape liner is automatically removed upon removal of the injection device 7.

Referring to FIGS. 23-25, the injection device 7 may have an adhesive tape flange 91 that extends beyond the undersurface base 76. This flange 91 of adhesive tape 88 can act as a strain relief between the injection device 7 and skin surface, reducing the risk of accidentally dislodging the injection device 7 from the skin. In other words, similar to a tapered strain relief on a wire where it enters into a connector, the extended adhesive flange 91 acts to distribute the load on both sides of the connection point between the adhesive tape 88 and the undersurface base 76 of the injection device 7 to reduce any stress risers at the adhesive tape 88 and skin interface.

Referring to FIGS. 23-25, the injection device 7 may be configured with a tapered underside surface 98 that presses on the adhesive flange 91 to securely attach the adhesive tape 88 to the skin as the user is securing the injection device 7 to the skin without additional user intervention. By using the compliance of a person's skin when pressing the injection device 7 against the skin, the tapered underside surface 98 of the injection device 7 effectively presses the flange 91 of the adhesive tape 88 against the skin but the upper exposed surface of the flange 91 portion does not have exposed adhesive and therefore is not attached to that portion of the tapered underside surface 98. The user is not required to run their finger around the flange 91 to secure the injection device 7 to the skin making it a much simpler method of adhesive tape 88 attachment.

Referring to FIGS. 23-25, the injection device 7 may have an underside surface 76 that is flexible or compliant in lieu of being rigid to allow for improved attachment by conforming of the injection device 7 to the skin during application.

Figure 26:
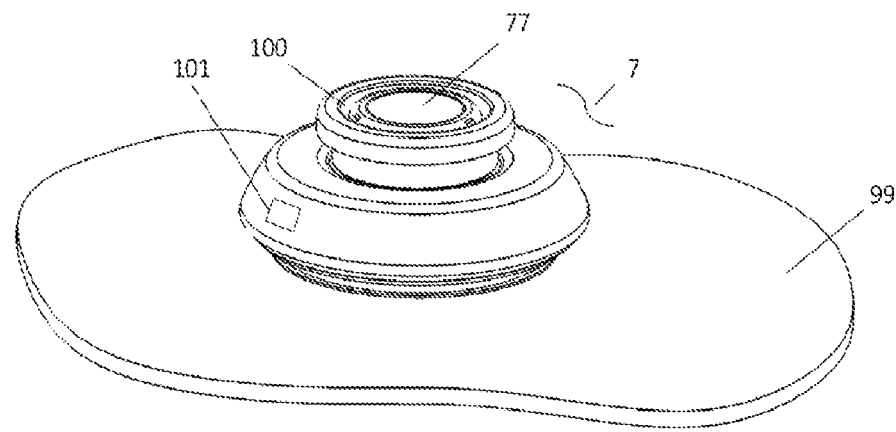
FIG. 26 is a perspective view of the injection device attached to the skin with the safety device installed.
Figure 27:
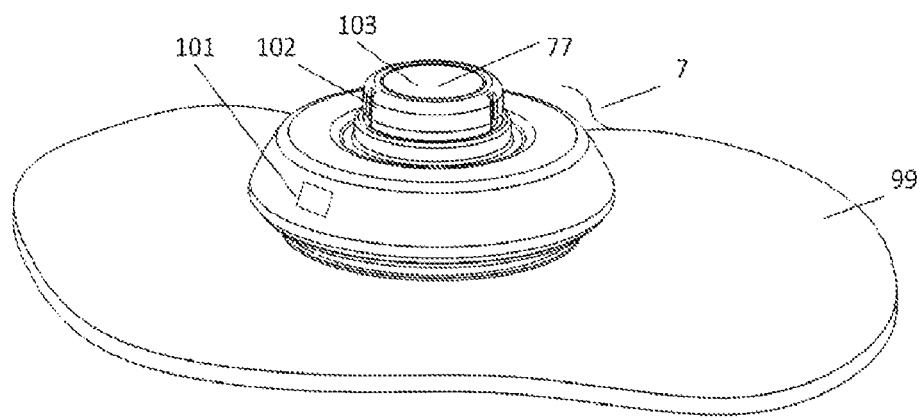
FIG. 27 is a perspective view of the injection device attached to the skin with the safety device removed and the button up in a pre-fire state.
Figure 28:
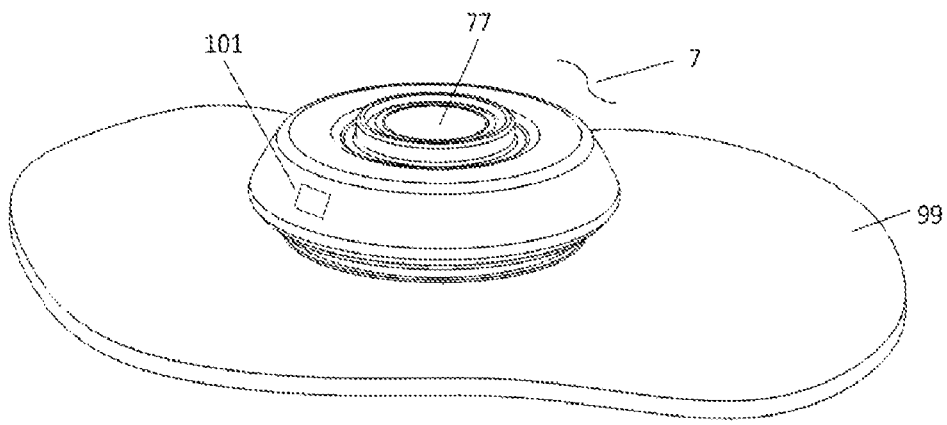
FIG. 28 is a perspective view of the injection device attached to the skin with the safety device removed and the button down in a fired state.

Referring to FIGS. 26-28, after the injection device 7 is placed against or adhered to the skin 99, a safety mechanism or lock-out mechanism may be automatically released and the injection device 7 is ready to fire (inject). In other words, the injection device 7 is prevented from being actuated (it is locked out) until it is placed against the skin. Alternatively, the user may manually remove a safety 100 such as a safety pin, safety sleeve, or collar to release the injection device to be ready to fire (inject). The injection device 7 preferably cannot be fired until the safety mechanism 100 is released. The safety mechanism 100 may be passive or active and manually triggered by the user or automatically triggered by the injection device 7.

Referring to FIGS. 26-28, the injection device 7 may use an actuator or button 77 and a visual indicator 101 in combination to define the state of the injection device 7 after it has been removed from the transfer apparatus. For example, when the button 77 is in the up position and the indicator 101 has one color such as but not limited to green, this may indicate that the injection device 7 is ready to start the injection. Additionally, the button 77 may have a side wall 102 that is a different color from its top 103. When the button 77 is depressed, the user cannot see the sidewall 102 of the button 77; this may indicate that the injection device 7 is in use. The injection device 7 may alert the user when the injection of the drug is completed. This alert could be in the form of visual indicators, audible sounds, mechanical movements or a combination. The button 77 is ideally designed to give the user audible, visual and tactile feedback when the button 77 'pops up' into the locked-out position. The injection device 7 may indicate to the user that it is has completed dispensing and the full dose has been delivered to the patient with the button 77 in the up position and indicator window 101 showing the injection device is empty. For example, when the button 77 is in the up position and indicator 101 shows a different color such as but not limited to red, this may indicate that the injection device 7 has completed the injection.

Figure 29:
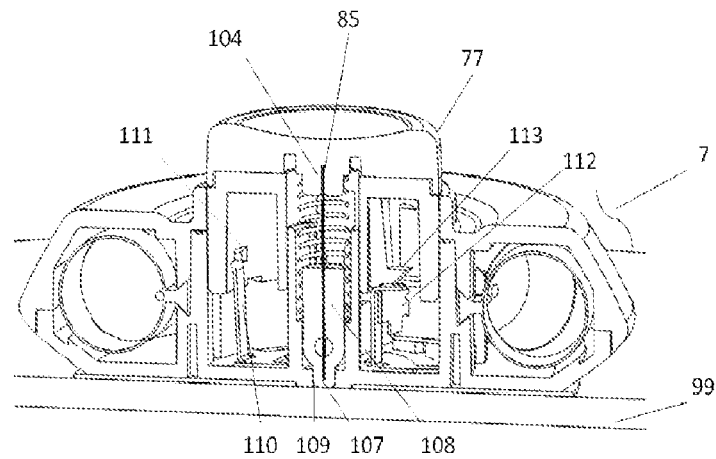
FIG. 29 is a cross-section view of the injection device attached to the skin with the button up in a pre-fire state.
Figure 30:
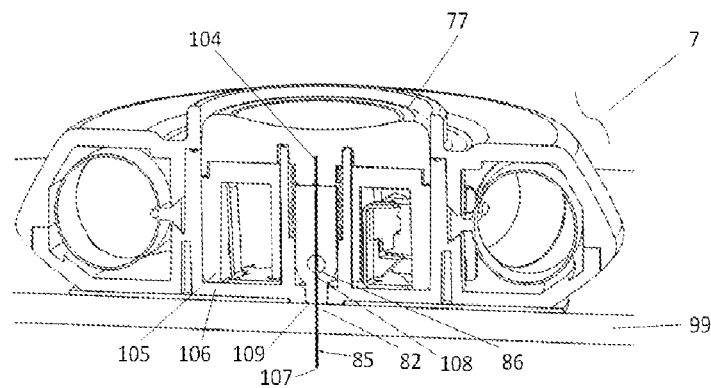
FIG. 30 is a cross-section view of the injection device attached to the skin with button down in a first fired state.
Figure 31:
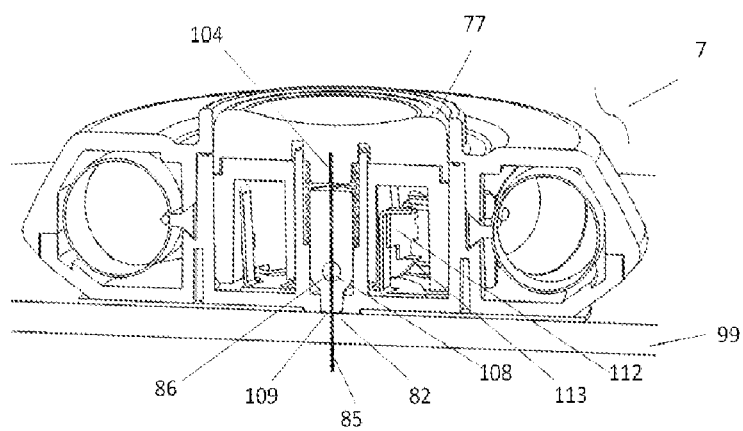
FIG. 31 is a cross-section view of the injection device attached to the skin with button down in a dispense state.

Referring to FIGS. 29-31, the injection device 7 may have an actuator or button 77 that the user depresses on the injection device 7 to start the injection. The button 77 may be configured to be an on/off switch, i.e., to only have two states, open and closed such as a light switch. This may prevent the user from pushing the button 77 half way and not actuating the injection device 7. Once activated, this 'light switch' type button 77 would insert the needle 85 rapidly into the skin 99, independent of the user manipulation of the button 77. Alternatively, the button 77 could have a continuous motion, allowing the user to slowly insert the needle 85 into skin 99. The button 77 may preferably be directly coupled to the needle 85 by using adhesive 104 creating a button 77 and needle 85.

Referring to FIGS. 29-31, the injection device 7 may have a needle 85 travel into the skin 99, upon actuation of the button 77 that initially goes to a first position or depth as shown in FIG. 30 and retracts slightly to a second position of depth preferably automatically as shown in FIG. 31. The first depth shown in FIG. 30 is achieved from over travel of the button 77 during actuation. The first depth may be controlled by features 105 in the button 77 in direct contact with the base 106 of the injection device 7. The final depth of the needle 85 is suitable for subcutaneous injections. Alternatively, the final depth of the needle 85 may be reduced for intradermal injections. Alternatively, the final depth of the needle 85 may be increased for intramuscular injections. Upon reaching the first depth, the needle 85 retracts back to a second depth as shown in FIG. 31. The retraction distance of the needle to the second depth is in the range of 0.1-2 mm. This retraction feature is preferable to prevent the needle 85 from being blocked by tissue during the initial insertion process. This tissue blockage could require a very high pressure to overcome and prevent the injection device 7 from delivering the drug. The retraction of the needle 85 from the first position to a second position creates an open pocket ahead of the needle tip 107 allowing reduced pressure for initiation of flow of drug from the needle 85. This reduced pressure for initiation of the flow of drug from the needle is preferable for the injection device 7 to maintain a relatively constant pressure during injection.

Referring to FIGS. 29-31, the injection device 7 may include a needle 85 with a side hole 108. As shown in FIG. 31, once the button 77 on the injection device 7 is fully depressed, the needle 85 will be fully inserted into the skin 99 through the dispense port 82 and the injection device 7 will begin dispensing of the injectable. Until the button 77 is fully depressed, the side-hole 108 and therefore the internal lumen of the needle 85 is not in communication with the fluid channel 86 of the dispense port 82. Both the side-hole 108 and needle-tip 107 are retained within a septum 109. With the side-hole 108 and needle-tip 107 being retained within the septum 109, the entire drug path is kept sterile until the time of use. When the button 77 is fully depressed and the needle 85 is in the dispense position, a side hole 108 in the needle 85 is in communication with the fluid channel 86 of the dispense port 82 and the injection of the liquid begins.

Referring to FIGS. 29-31, the septum 109 provides the advantage of sealing the needle tip 107 as well as the side hole 108 from the injectable before and after dispense. Sealing the needle tip 107 and the side hole 108 of the needle 85 at the end of the injection has a particular advantage to prevent dripping of injectable from the injection device 7 after end of dispense and/or after it is removed from the skin surface. It also prevents contaminates from entering the hollow needle prior to being actuated into the skin. The septum 109 may be made of any suitable material to allow for sealing once the needle 85 has punctured it. The material composition of septum 109 may preferably be silicone. Alternatively, the material composition of the septum may also be a blend of different materials including but not limited to bromobutyl, chlorobutyl, isoprene, polyisoprene, SBR, polybudtadiene, EPDM, natural rubber and silicone. Alternatively, the fluid pathway 86 including the dispense port 82 could be a rigid plastic with a silicone injected overmold to produce the septum previously described.

Referring to FIGS. 29-31, the septum 109 at the dispense port 82 could protrude slightly from the underneath surface into the skin surface 99 of the injection device 7 to provide for pressure on the skin surface 99 at the injection site. This pressure on the skin surface 99 by the dispense port 82 after the needle is retracted could eliminate injectable from coming out of the injection site commonly referred to as blowback.

Referring to FIGS. 29-31, the injection device 7 may include a set of spring tabs 110 that interface with the button 77 to perform locking functions. A spring tab 110 is biased to lock into an undercut 111 in the button 77 to keep the button 77 in a first up position or pre-fire position as shown in FIG. 29. The geometry of the undercut 111 and spring tab 110 help to produce the light switch actuation force described previously. This light switch actuation is accomplished by the translation of the button 77 relative to the spring tab 110 and the geometry of the mating undercut 111 surfaces.

Referring to FIGS. 29-31, the injection device 7 may include a spring tab 112 that interact with the button 77 in the injection device 7 to perform locking functions such that when the button 77 is actuated to the first depth and retracts slightly back to the second depth or dispense position, undercut features 113 in the button 77 allow a spring tab 112 to hold the button 77 in the dispense position until the injection device 7 has completed dispensing.

Figure 32:
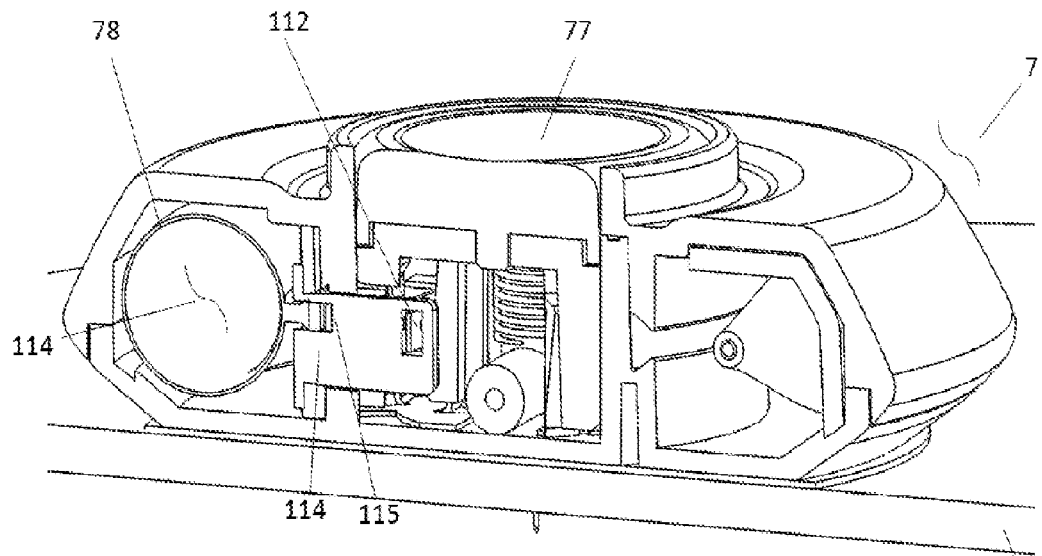
FIG. 32 is a cross-section view of the injection device attached to the skin showing the end of delivery indicator not triggered.
Figure 33:
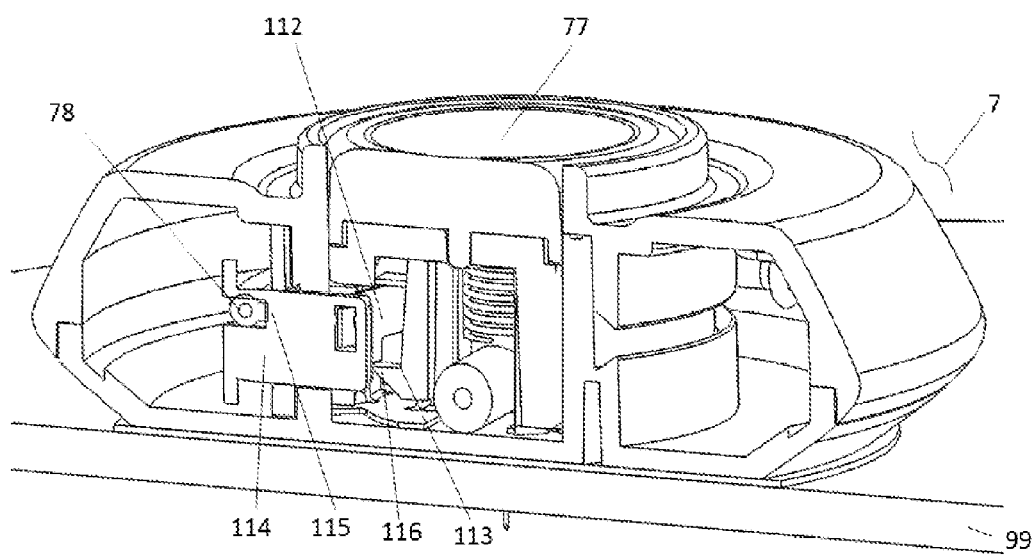
FIG. 33 is a cross-section view of the injection device attached to the skin showing the end of delivery indicator triggered.

Referring to FIGS. 32-33, the injection device 7 may include an end of delivery indication or empty indicator 114 to sense when all of the fluid 79 has been expelled from the expandable member 78 and the injection device 7 has completed dispensing. The empty indicator 114 may be configured with a slot or other opening 115 to slide over the expandable member 78 at the exit port when the expandable member 78 is in a deflated state after all of the fluid has been expelled. There may be two states of the empty indicator. As shown in FIG. 32, the empty indicator may be in a first position or deflected-out state when the expandable member 78 is full with fluid 79 at that section and is not contained within the slot or opening 115. This first position would translate to a non-empty state of the expandable member 78 when the diameter of the expandable member 78 is larger than its minimum due to residual fluid 79 contained within. As shown in FIG. 33, the empty indicator 114 may be in a second position or deflected-in state when the expandable member 78 is partially or fully contained within the slot or opening 115. This second position would translate to an empty state of the expandable member 78 when the diameter is at a minimum.

Referring to FIGS. 32-33, the injection device 7 may include an automatic needle retraction mechanism at the end of dispense. This mechanism includes a direct coupling between a spring tab 112, button undercut feature 113 and the empty indicator 114, all previously mentioned. When the expandable member 78 is filled with injectable 79 and the button 77 is depressed from a first pre-fire position to a second dispense position as shown in FIG. 33, undercut features 113 in the button 77 allow a spring tab 112 to hold the button 77 in the dispense position until the injection device 7 has completed dispensing. This spring tab 112 may also be directly coupled to the empty indicator 114 which is naturally in the first position or deflected-out state. The motion of depressing the button 77 to a second position or dispense position allows a post feature 116 in the button 77 to provide a bias or pre-tension on the spring tab 112 to urge the empty indicator 114 to its second position or deflected-in state. However, since the expandable member 78 is initially full with injectable 79 at a large diameter, the empty indicator 114 cannot move to the second position or deflected-in state as shown in FIG. 32. After the button 77 is depressed, the fluid 79 starts to expel out of the expandable member 78 through the needle as previously mentioned. Once the expandable member 78 has expelled all of the fluid 79 and is at a minimum diameter, the empty indicator 114 (under pretension from the spring tab 112) will move to the second position or deflected-in state as shown in FIG. 33. The spring tab 112 directly coupled to the empty indicator 114 also moves with the empty indicator 114. This movement releases the spring tab 112 from the undercut feature 113 in the button 77 to allow the button 77 (and needle) to move up to a final position or post fire position after the dispense is completed as shown in FIG. 34.

Figure 34:
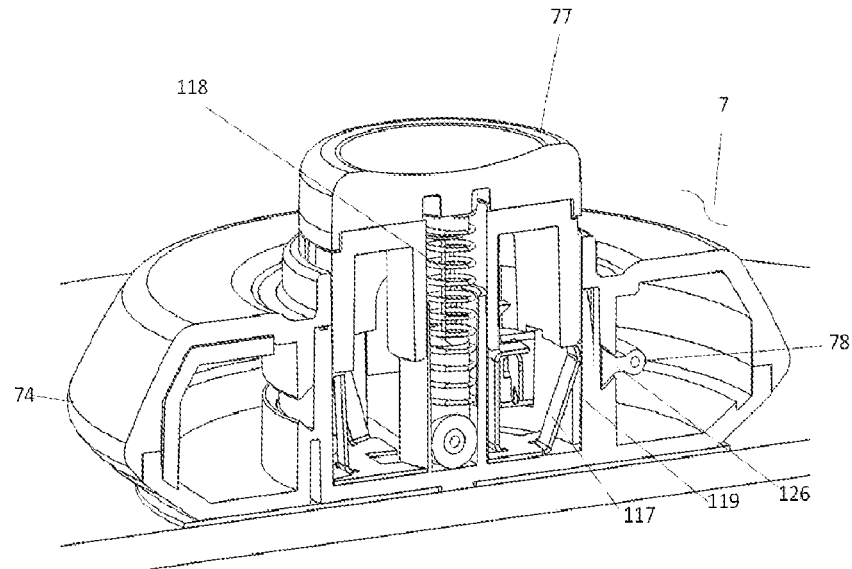
FIG. 34 is a cross-section view of the injection device attached to the skin with button locked up in a post-fired state.

Referring to FIG. 34, lock out spring tabs 117 may also interact with the button 77 in the injection device 7 to perform locking functions such that when the injection is complete the button 77 is released, and the button 77 is urged up by the return spring 118 to a final up position or post-fire position. The button height 77 relative to the top of the injection device 7 in the final up position or post-fire position (shown in FIG. 34) may be higher than the pre-firing position (shown in FIG. 29). The end of the lock out spring tabs 117 move out to the outer diameter surface 119 of the button 77 within the outer housing 74 to lock the button 77 in the up position or post-fire position and prevent the button 77 from being actuated again.

Referring to FIG. 34, the injection device 7 may include a return spring 118 that interacts with the button 77 to provide a bias to the button 77 into a first up position or pre-fire position. When the button is actuated down to a second depth or dispense position, the return spring 118 is compressed causing more of a bias or preload. At the end of the dispense period, the button 77 is unlocked from the second depth or dispense position (shown in FIG. 31) to move up to a final position or post fire position after the dispense is completed as previously mentioned. It is the bias of the return spring 118 that forces the button 77 up to a final position or post-fire position.

Figure 35:
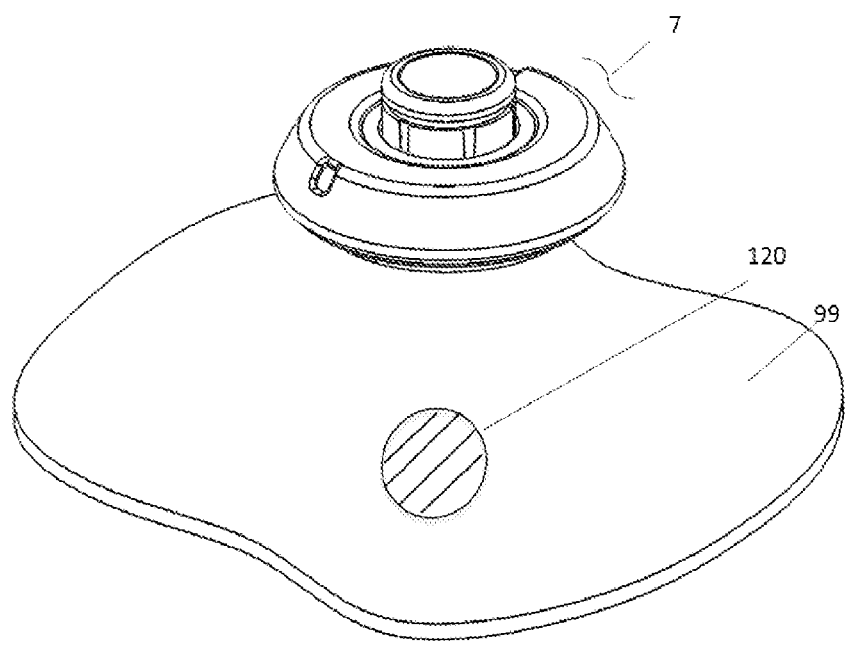
FIG. 35 is a perspective view of the injection device removed from the skin with the bandage remaining on the skin.

Referring to FIG. 34-35, upon removal of the injection device 7 from the skin 99, the injection device 7 will preferably be locked out, preventing non-destructive access to the needle or reuse of the injection device 7. The injection device 7 may indicate to the user that the full dose has been delivered. This indication could be in the form of a visual indictor, audible sound, mechanical movement or a combination.

Referring to FIG. 35, upon removal of the injection device 7 from the skin 35, a bandage 120 may release from the injection device 7 and remain on the skin surface 35. This can be affected by using an adhesive on the bandage portion that more strongly attaches the bandage to the skin than the adhesive that attaches the bandage to the injection device 7. Thus when the housing is lifted from the skin, the bandage 120 remains in place over the injection site as described in U.S. Pat. No. 7,637,891 and U.S. patent application Ser. No. 12/630,996, filed Dec. 4, 2009 incorporated by reference herein.

Referring to FIGS. 36-39, the injection device 7 may preferably include a manifold 121 that assembles to both the expandable member 78 and the filling port 81 and dispensing ports 82, and provides direct fluid communication between the expandable member 78 and the filling 81 and dispensing 82 ports of the injection device 7. The manifold 121 may be configured on the end that assembles to the expandable member 78 to be large in diameter to facilitate filling and expelling all of the fluid 79 out of the expandable member 78 as previously discussed. The manifold 121 may preferably include internal passageways 122 to allow for fluid flow in and out of the expandable member 78. The manifold 121 may be configured with a filter 123 in the injectable fluid pathway 122 for filtering the injectable 79 to remove particulate before and after it is introduced into the expandable member 78. The filter 123 may be a membrane, depth filter or other suitable filtration media that is of sufficiently small pore size or effective pore size to remove objectionable particulate, which may include but not be limited to undissolved injectable 79 in those situations where the injectable 79 is reconstituted by the transfer apparatus. The manifold 121 may also be configured with a filter 123 for the removal or air. Such an air remover filter 123 may include a bubble trap, air gap of other configuration in the injectable fluid pathway 122 that removes air from the injectable fluid pathway 122 before it is introduced into the expandable member 78. This air remover filter 123 may be configured with a hydrophobic filter or a combination of hydrophobic and hydrophilic filters. A hydrophobic filter would allow for the venting of air from the transfer apparatus but not the passage of liquid. A hydrophilic filter would allow the passage of liquid but not the passage of particulate or air. The air remover filter 123 may also have check valves to allow for venting of trapped air. Alternately, the air remover and filters 123 may be located at any point in the fluid pathway from the filling port 81 to the needle 85. For example, the most downstream point in the fluid pathway is the distal end 128 of the expandable member 78. An internal mandrel 124 may be connected to distal end 128 of the expandable member 78. An air remover or filter 123 may be integrated into this downstream point to allow for venting of trapped air during filling of the injection device 7. Furthermore, the mandrel 124 could include a slot along its length that is in communication with the downstream filter 123 to aid in the venting of air during the filling process.

Referring to FIGS. 36-39, the injection device 7 may include a resilient expandable member 78 such as an elastomeric balloon or bladder. The material composition of expandable member 78 may preferably be silicone. Alternatively, the material composition of the expandable member 78 may also be a blend of different materials including but not limited to bromobutyl, chlorobutyl, isoprene, polyisoprene, SBR, polybudtadiene, EPDM, natural rubber and silicone. In addition, the expandable member 78 may be coated to improve their surface properties. Coatings may include parylene, silicone, Teflon and fluorine gas treatments. Alternatively, the expandable member 78 may be made from a thermoplastic elastomer.

Referring to FIGS. 36-39, the injection device 7 may include a resilient expandable member 78 which the injectable 79 is transferred under pressure. This causes the expandable member 78 to enlarge and the resilience of the expandable member 78 creates a pressure which tends to expel the injectable 79. The pressure chamber of the transfer apparatus described previously (or such other pump or pressurizing means as may be employed in the transfer apparatus) transfers the injectable 79 to the injection device 7 under pressure. Introducing the injectable 79 into the expandable member 78 under pressure causes it to stretch and expand both in diameter and length. An example of this would be blowing up a long, skinny balloon. The volume range of the injection device 7 may be 0.5 to 30 milliliter. When expanded, the resilient expandable member 78 exerts an expulsion pressure in the range of 1 to 200 psi on the injectable 79 contained in the expandable member 78 so that the injection device 7 is ready to administer the injectable 79 automatically when triggered by the user by depression of the button as previously described. Thus, the transfer apparatus as previously described operates not only to transfer a measured amount of injectable 79 (and if necessary mix, dilute and filter it) to the injection device 7, but also simultaneously charges or provides the motive pressure to the injection device 7 (by expanding the resilient expandable member 78) so that the injection device 7 is ready to automatically dispense the injectable 79 under the pressure exerted by the resilient expandable member 78 when actuated by the user.

This aspect of the transfer apparatus (simultaneous transferring and charging) is particularly beneficial. While the above applications show the injection device 7 in a pre-filled or charged condition for injection of the drug 79 when the injection device 7 is actuated, the present disclosure contemplates that the injection device 7 can remain empty and the expandable member 78 in a more relaxed and un-filled condition, i.e., in a non-charged or non-filled condition, until administration of the injectable 79 is required. Only then is the injectable 79 mixed or processed as necessary and introduced into the injection device 7, expanding the expandable member 78 to a filled (charged) condition. In the present disclosure, the drug is stored in its original container closure (vial) until the time of use. Because the injectable 79 will typically be injected within seconds to hours after transfer from the vial into injection device 7, shelf life and material compatibility of the drug with the materials in the fluid pathway within the injection device 7 are not significant issues. The challenges and expense of designing an injection device 7 and selecting materials for an extended shelf life of pre-filled injection device 7 are significantly reduced.

Referring to FIGS. 36-39, the present subject matter may use features of the injection device 7 described in the patent applications incorporated by reference herein as previously described. However, the expandable member 78 employed in the injection device 7 here may also preferably take the form of an elongated balloon or bladder arra ed, for example, in a planar helical or spiral configuration as illustrated. As previously mentioned, the injection device 7 includes a circular shaped outer housing 74 that has a spiral slot or recess 125 formed therein. The elongated balloon or bladder (the expandable member 78) rests in the slot 125, with one end for communicating directly or indirectly with an injection needle 85 through fluid pathways 122 and the other end for communicating directly or indirectly with a dispense indicator 101. The elongated spiral configuration allows the balloon or bladder (expandable member 78) to have substantial volume for such quantity of injectable 79 as may be desired, while also contributing to the low profile configuration of the injection device 7. In other words, by utilizing a relatively long expandable member 78 with a large length to diameter ratio, very high pressures and volumes can be achieve with a minimum of forces required. Additionally the volume of the expandable member 78 can be changed by changing the filling length, without significantly altering the pressure/volume curves of the expandable member 78.

Figure 36:
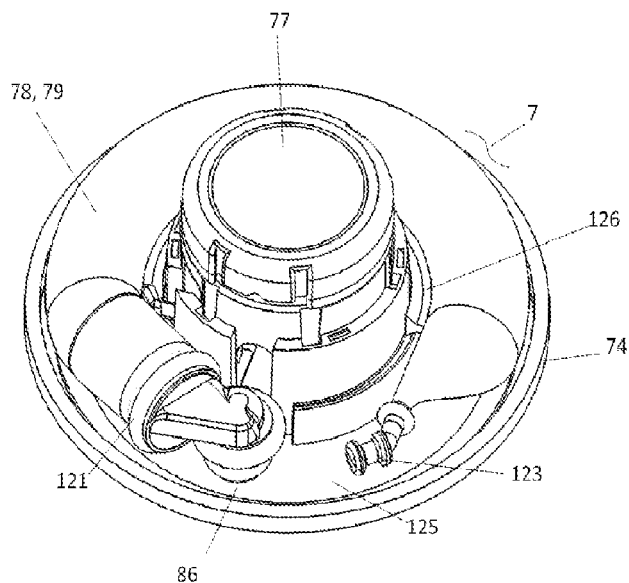
FIG. 36 is a perspective view of the injection device with the top housing removed in a filled state.
Figure 37:
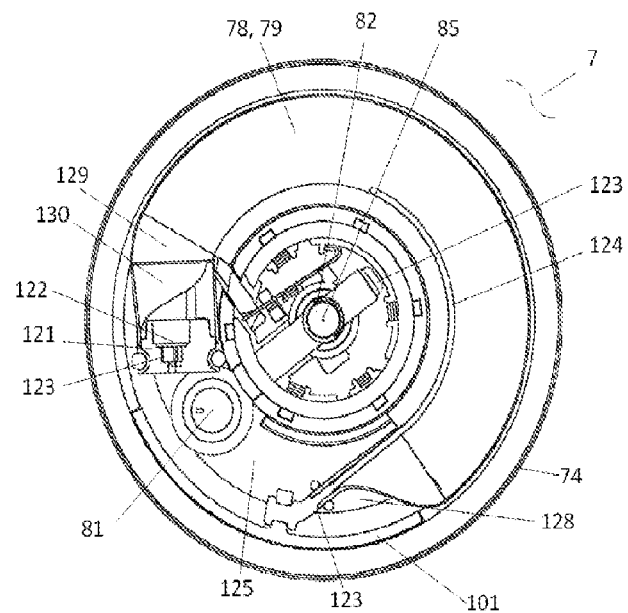
FIG. 37 is a top view of the injection device shown in FIG. 36.
Figure 38:
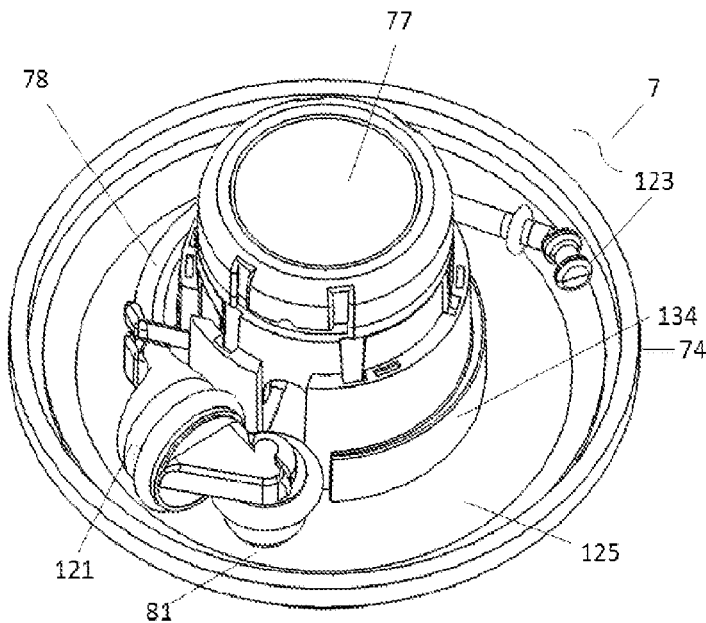
FIG. 38 is a perspective view of the injection device with the top housing removed in an empty state.
Figure 39:
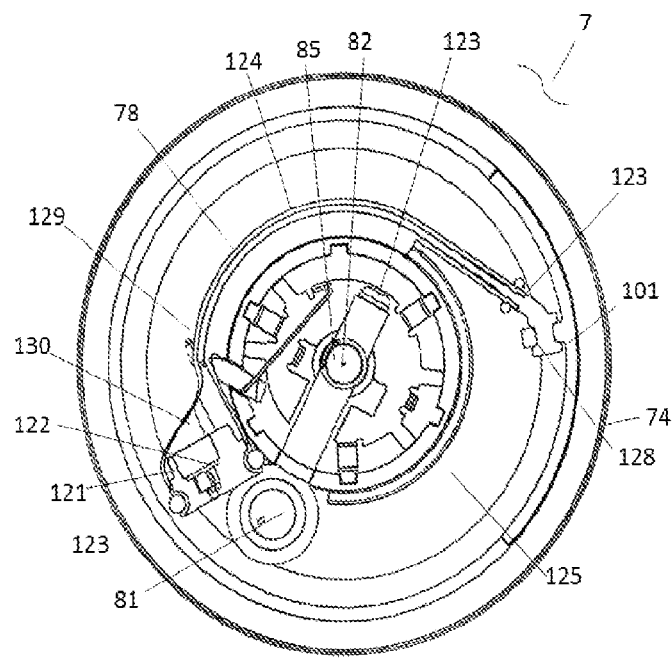
FIG. 39 is a top view of the injection device shown in FIG. 38.

Referring to FIGS. 36-39, one of the other aspects described in U.S. patent application No. 61/704,922, filed Sep. 24, 2012, that may be employed in the present subject matter is the use of an insert or plug or mandrel 124 within the expandable member 78 to pre-stress the expandable member 78 to a slightly expanded position when unfilled, so that when the expandable member 78 expels the injectable 79, it will contract or collapse to a condition where it is still stretched or stressed and continues to exert pressure on any fluid there within as shown in FIGS. 38 and 39. This better assures that all or substantially all of the injectable 79 is fully expelled from the injection device 7. The mandrel or shaft 124 could be a fluid filled expandable member if desired. This would allow for a variable size mandrel 124. Alternatively, the expandable member 78 could have a sufficiently small internal volume (small diameter) when unstressed so that virtually all the injectable 79 is expelled without the need for and internal mandrel or shaft 124. Additionally, the expandable member 78 could be flattened/stretched by 'wrapping' it around a surface within the injection device such as a cylindrical wall 134. The pre-stress created in the expandable member 78 would act to eliminate any residual fluid volume remaining within.

There are a number of different ways to cause an expandable member 78 to expand and/or contract in an arcuate manner as previously described. Referring back to FIG. 34, one way is to design the expandable member 78 with a thicker wall cross section 126 in one area around the circumference of the expandable member 78 that would cause the expandable member 78 to expand in a circular fashion. Alternatively, a separate element 126 could be affixed along the length of the expandable member 78 to effectively stiffen the expandable member 78 in that portion of the circumference that would cause the expandable member 78 to expand in an arcuate manner. Referring back to FIG. 36, another way is to use internal features such as slots or recesses 125 in the housing 74 of the injection device 7 to guide the expandable member 78 around a circular or spiral path. These features 125 could interact with the expandable member 78 in a number of ways, the simplest being the outer shape of the expandable member is constrained by a slot 125 in the housing 74 of the injection device 7. Friction between the expandable member 78 and the inner surfaces 125 of the housing 74 could be reduced by lubricating the outside surface of the expandable member 78, or by inserting the expandable member 78 within a low spring rate spring that would limit both the friction and outer diameter of the expandable member 78 while not constraining the length.

Referring to FIGS. 36-39, the elongated expandable member 78 may be preferably configured to expand along an arc with a predetermined tube diameter without the aid of walls or a guide within the injection device. Referring back to FIG. 34, looking at a cross-section of the elongated expandable member 78, a thicker wall area 126 in a small portion of the circumference of the expandable member 78 may be added to cause the elongated expandable member 78 to expand in an arc as previously described. The arcuate expandable member 78 grows in length due to increase in pressure and volume there within; the thicker section 126 deflects less than the thinner section.

Referring to FIG. 36, the arcuate expandable member 78 will expand in length in an arc shape as to orient its heavy wall thickness zone 126 or less deflecting zone to the inside of the circle. Increasing the wall thickness 126 of the expandable member 78 within the small zone 126 around the circumference will effectively continue to decrease the radius of the arc of the expandable member 78. The increase in wall thickness 126 may be achieved by molding or extruding it into the arcuate expandable member 78 or by bonding a strip of material to one side 126 of the expandable member to cause that portion of the wall 126 to lengthen at a slower rate, thereby causing the expandable member 78 to expand in an arc shape as previously discussed.

Referring to FIG. 37, the distal end of the expandable member 78 could be affixed an element such as an indicator 101, which is constrained to follow guide path within the inner surfaces 125 of the housing 74. Alternately, the expandable member 78 could be pre-stretched and flattened around a circular diameter inside the injection device 7 such as wall 134 so that there would be no change in expandable member length. Alternatively, a straight or curved mandrel 124 whose length is more than the unstressed expandable member could be used to stretch the expandable member into a circular shape within the injection device 7 prior to filling. Alternatively, the mandrel 124 could be used as a visual indicator to show the state of the injection device 7 and the progress of the injection. The mandrel 124 could be colored to allow it to be easily viewed through the housing.

Referring to FIGS. 36-39, the injectable 79 is injected into the expandable member 78 by the transfer apparatus and the expandable member 78 is expanded to a certain outer diameter controlled by the configuration of the inner surfaces 125 of the housing 74. In this way, the entire length of the expandable member 78 can be filled with a known volume of drug, and the outer diameter is known at each lengthwise location along the expandable member 78. It is desirable to have the expandable member 78 fill and empty along its length in a controlled way, from one end to the other to encourage the expandable member 78 to completely empty, and to allow the easy and accurate measurement of fluid 79 in the expandable member. To visually aid in determining how much fluid 79 is in the expandable member 78, graduated markings could be printed on the expandable member 78, like a syringe, to indicate the volume remaining in the expandable member 78. As previously described and referring to FIGS. 21-22, the expandable member 78 and housing 74 could be clear to allow the user to see the drug 74 and the volume remaining in the injection device 7. Alternatively, graduated markings 127 could be printed on the housing 74 to indicate the volume remaining in the expandable member 78.

Referring to FIGS. 36-39, in accordance with an aspect of this subject matter mentioned above, the injectable 79 is preferably expelled progressively from the distal end 128 of the elongated expandable member 78 toward the proximal end 129. The proximal end 129 of the expandable member is closest to the dispensing needle 82 or cannula. This allows the user to visually ascertain or approximate the injection status visually alone or with the aid of graduation markings 127 on the injection housing 74, the window 80 or the expandable member 78. Progressive expulsion may be achieved in a variety of ways. For example, the injectable 79 exits the expandable member 78 at the manifold 121 at the proximal exit port section 130 and is preferably located at the proximal end 129 of the elongated expandable member (e.g., balloon or bladder). The thickness of the wall of the expandable member 78 may be varied, uniformly or stepwise increased, along its length from the distal end 128 toward the proximal end 129. Due to restraint by the walls of the spiral channel 125 in which the expandable member 78 resides, the expandable member 78 would be inflated with injectable 79 to a substantially uniform diameter along its length. However, the thicker wall at the distal end 128 of the expandable member 78 would exert greater contraction force on the injectable 79 than the thinner wall at the proximal end 129 and thus collapse or contract in diameter first during expulsion of the injectable 79. The expandable member 78 would then collapse progressively from the distal end 128 toward the proximal end 129 as the wall of the expandable member 78 becomes thinner along its length in that direction. Because the thickness of the expandable member 78 preferably substantially uniformly increases from the proximal end 129 toward the distal or closed end 128, the contractive force of the expandable member 78 wall when expanded will increase substantially uniformly along the length of the elongated expandable member 78 from the proximal port end 129 to the distal or closed end 128. Thus, when the injectable 79 is expelled into the subject, the expandable member 78 will progressively collapse in diameter as well as shrink in length, which collapse in diameter and shrinkage in length is preferably viewable by the user as described above. The distal end 128 of the elongated expandable member may allow for the connection of a movable indicator component 101 in the injection device 7 which will follow the shrinkage in length of the elongated expandable member 78. This indicator 101 is preferably viewable by the user through the outer housing 74 and indicates the state of the injection device 7 and the progress of the injection. Alternatively, the expandable member 78 is configured with a constant wall thickness and could be prestressed in manufacturing to bias it to fill from the proximal end 129 to the distal end 128 and collapse or empty from the distal end 128 to the proximal end 129 in a progressive manner as previously discussed.

Referring to FIGS. 36-39, the elongated expandable member 78 of the injection device 7 may be configured to have a section 130 of the expandable member 7 adjacent to the proximal exit port end 130 that fills first and collapses last during filling and expulsion of the injectable 79 from the injection device 7. In other words, during filling of the injection device 7 by the transfer apparatus, it is advantageous to have the most proximal exit port section 130 of the expandable member 79 to fill with injectable first. Additionally, during dispense of the injectable 79 from the injection device 7, it is advantageous to have the last remaining volume of injectable 79 to be contained within the most proximal exit port section 130 the expandable member 79. There are several advantages to the abovementioned configuration. The proximal end section 130 of the expandable member 78 could have a thin wall that would cause it to remain inflated under a lower pressure than the rest of the expandable member 78. This would assure that the section 130 of the expandable member 78 would remain inflated until all injectable 79 had been expelled from the rest of the expandable member 78. As previously discussed, this section 130 may be directly coupled to an empty indicator to provide for full or empty indication. Additionally, as previously mentioned, this section 130 could be mechanically coupled to the empty indicator to allow for the automatic withdrawal of the button 77 and needle 82 upon complete expulsion of the injectable 79.

Referring to FIGS. 36-39, alternatively or in addition to varying the wall thickness 126 of the expandable member 78, an elongated internal mandrel or shaft 124 within the expandable member 78 may progressively (linearly or stepwise) decrease in cross-sectional size along the length of the expandable member 78 from proximal end (the exit port end) 129 toward the distal end (closed end) 128 of the expandable member 78. Additionally, the manifold 121 which allows for attachment of the expandable member 78 to the injection device 7 may also be configured with a large diameter section 130 at the proximal end 129 of the expandable member 78. A large diameter section 130 of the mandrel 124 or manifold 121 at the proximal end exit port 129 of the expandable member 78 insures that the expandable member 78 will fill with injectable 79 in this area 129 first. In other words, the expandable member 78 is being held at nearly a fill diameter at the proximal end exit port 129 by the large diameter section 130 of the mandrel 120 or manifold 121. As fluid 79 first starts to fill the expandable member 78, it reaches a fill diameter first in the large diameter section 130 then fills progressively along the length of the expandable member 78 from the proximal end 129 to the distal end 128 as previously discussed.

Referring to FIGS. 36-39, as previously discussed, during dispense of injectable 79 from the expandable member 78, the diameter of the expandable member 78 at its distal end continuously collapses in a progressive fashion (similar to deflating a long skinny balloon) from its distal 128 to proximal end 129 until all of the fluid is expelled from the expandable member 78. A large diameter section 130 of the mandrel 124 or manifold 121 at the proximal end exit port 129 of the expandable member 78 provides the same benefit (as previously described for filling) during dispense of the injectable 79. This large diameter section 130 insures that the last remaining fluid 79 in the expandable member 78 will be contained and dispensed from this area 130. As previously discussed, this section 130 may be directly coupled to an empty indicator to provide for full or empty indication as well as for the automatic withdrawal of the button 77 and needle 82 upon complete expulsion of the injectable 79.

Operation and Method

Figure 40:
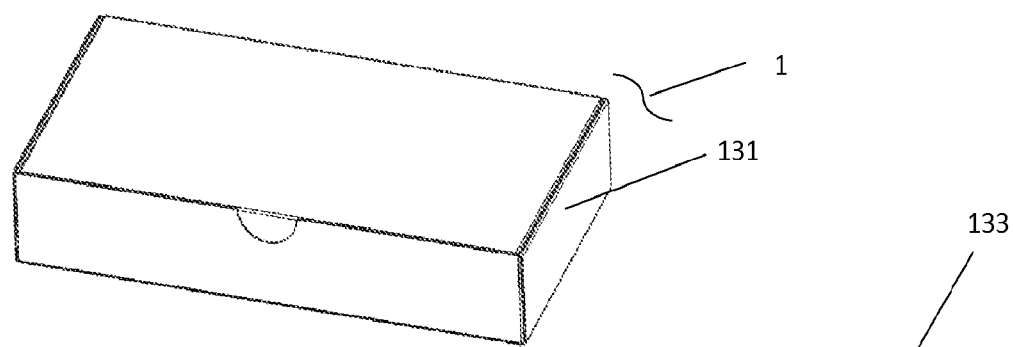
FIG. 40 is a perspective view of the single vial system in the packaging.
Figure 41:
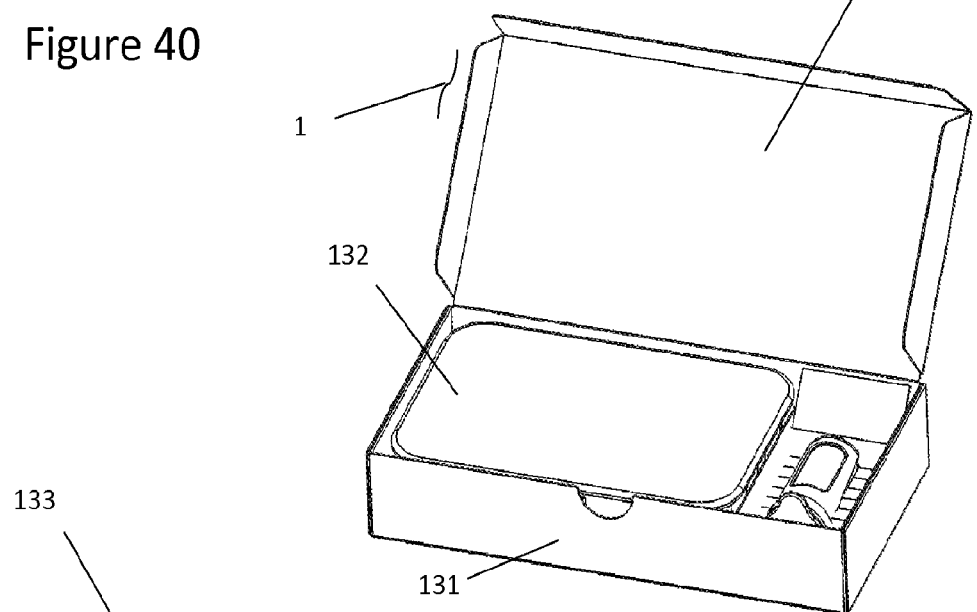
FIG. 41 is a perspective view of the single vial system in the packaging open.
Figure 42:
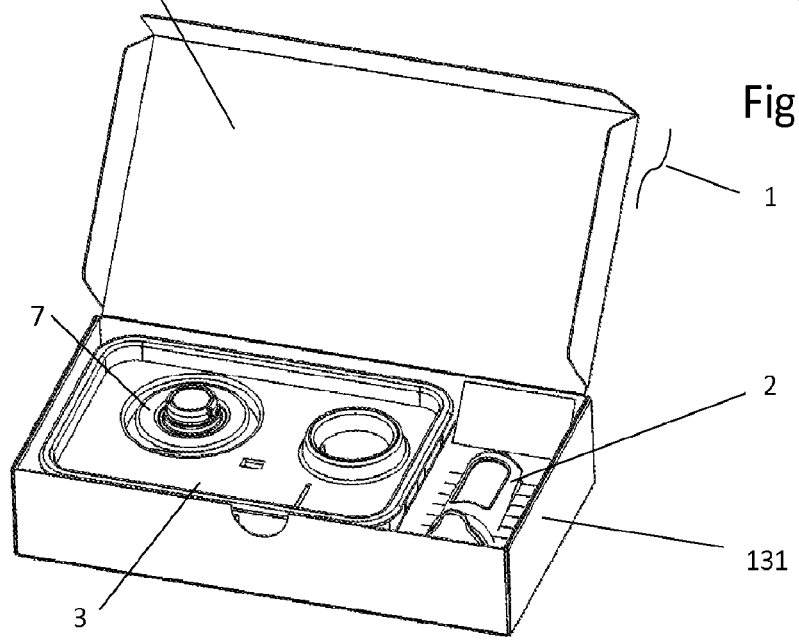
FIG. 42 is a perspective view of the single vial system in the packaging with the lid removed exposing the contents of the package.

Referring to FIGS. 40-42, the sterile injection device 7 is attached to the transfer apparatus 3 within a covered tray 132 and a separately packaged vial holder 2 with filled vial(s) is provided in a carton 131. The user places the carton 131 on a clean, flat surface. The user opens the lid 133 to the carton 131 to expose the transfer apparatus 3 and vial holder assembly 2. The user removes the cover 132 from the transfer apparatus tray 3 to expose the transfer apparatus 3 and injection device 7. The user is instructed to leave the transfer apparatus 3 in the carton 131 and only remove the injection device 7 when prompted.

Figure 43:
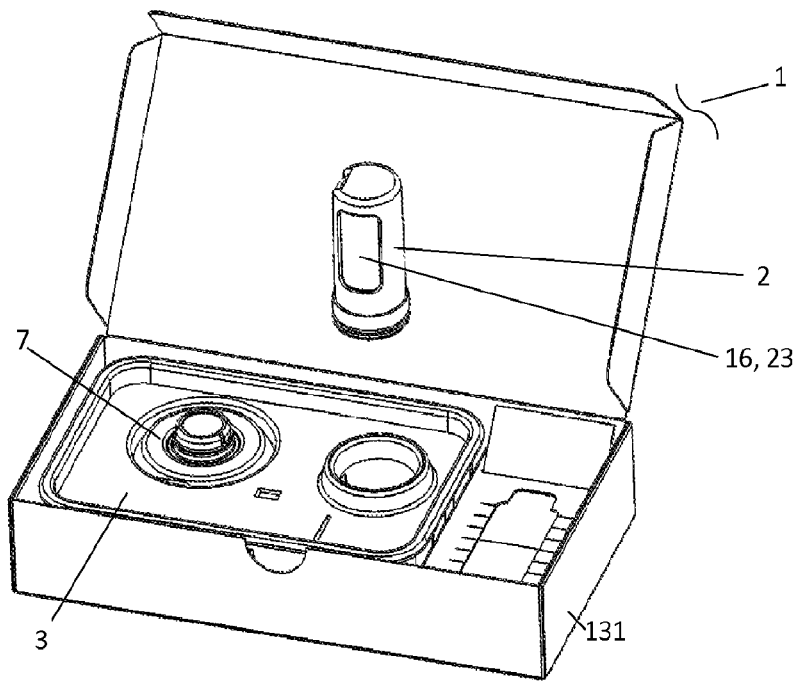
FIG. 43 is a perspective view of the single vial system with the vial holder removed from the package and the vial cap removed.
Figure 44:
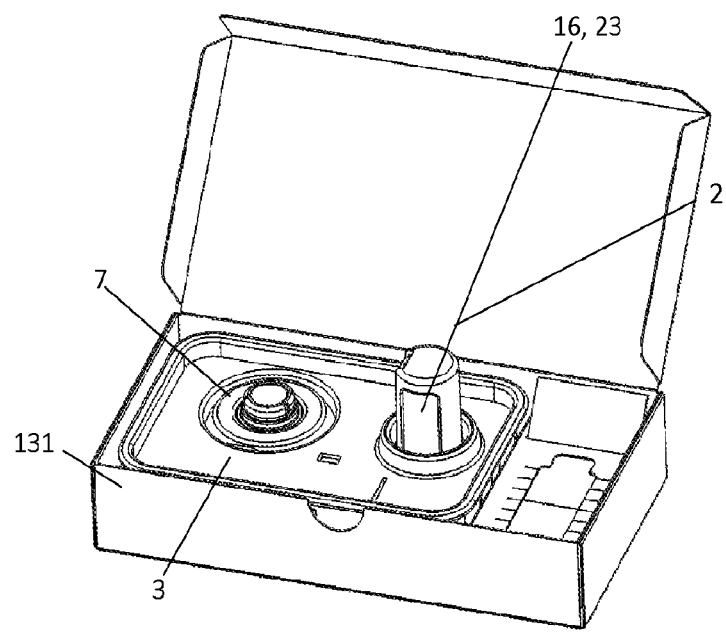
FIG. 44 is a perspective view of the single vial system with the vial holder fully inserted into the transfer apparatus.

Referring to FIG. 43-44, at the time of use, the user will remove the vial holder assembly 2 from the carton 131. The user will then remove the vial cap from the vial using the attached cap remover. The user will insert the vial holder 2 into the transfer apparatus 3. The user will push the vial holder 2 with attached vial 16 into the transfer apparatus 3 to actuate the system 1. This will do three things in the illustrated embodiment. First it will lock the vial holder 2 with attached vial 16 into a down position within the transfer apparatus 3. Then it will automatically initiate fluid communication between the contents 23 of the vial 16 and the transfer apparatus 3 by introducing an access member through the septum of the vial. Third it will initiate the mixing (if needed) and transfer sequence of the transfer apparatus 3. This sequence of events will occur automatically and require no additional input by the user to proceed.

Figure 45:
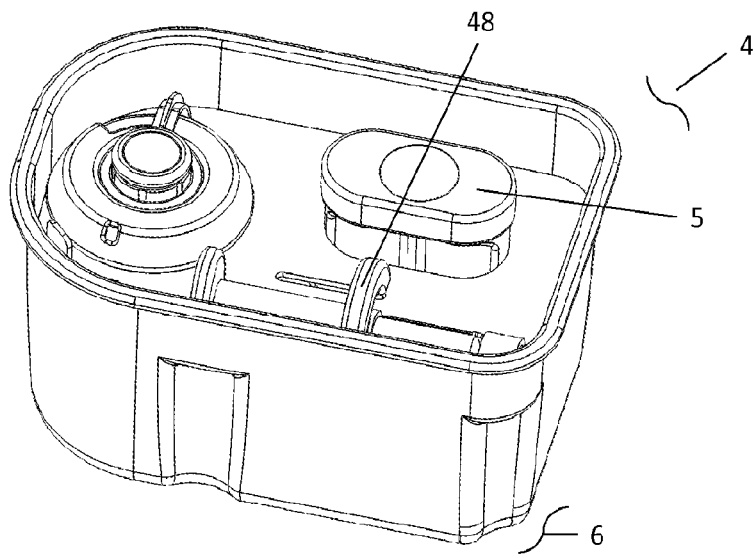
FIG. 45 is a perspective view of a dual vial system showing the vial holder installed.
Figure 46:
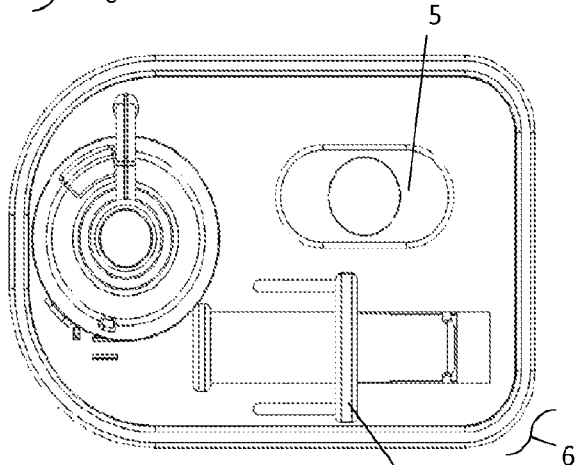
FIG. 46 is a top view of FIG. 45 showing the volume controller in a preset state.
Figure 47:
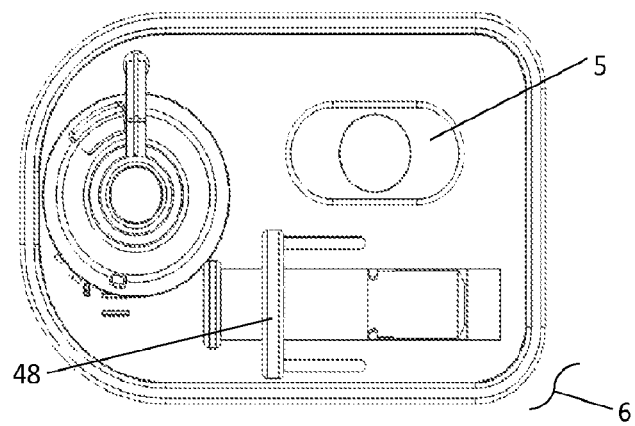
FIG. 47 is a top view of FIG. 45 showing the volume controller in a set state.

Referring to FIGS. 45-47, in a dual vial system 4 where mixing is required; the user may have the ability to adjust the delivery dose. A dose selector 48 is moved from an initial position shown in FIG. 46 to a final delivery volume position in FIG. 47. At this point, the vial holder 5 is free to depress by the user allow for the mixing and transfer to initiate. First, the diluent fluid is transferred from the diluent vial and introduced into the powdered lyophilized injectable vial. The fluid will be introduced into the powdered vial in such a way so that when the fluid is transferred from the vial, all the powder is removed as well. Mixing of the diluent and powder may occur completely in the powdered vial, or may be completed in the transfer apparatus. Static or dynamic mixing elements may be incorporated into the transfer apparatus or introduced into the powder vial by the transfer apparatus to allow for adequate mixing of the powered drug or other injectable and diluent. The mixing may take up to several minutes to complete. The mixing will be done in as gentle a way as possible to minimize bubbles/foaming and shear stresses in the mixture. The mixing also will be done in such a way to encourage the powder to be completely mixed, and no particles are present. In-line filters, valves or other means may be employed to remove particles or air. There may be an indicator on the transfer apparatus showing that mixing is progressing.

Referring to FIGS. 45-47, in a dual vial system 5, the reconstituted solution is mixed in the powdered vial or transfer apparatus 6, a set volume of solution prescribed by the manufacturer or set by the user is automatically transferred into the pressure dose chamber. This set volume is then automatically transferred to the injection device 7. The tubes, conduits valves and any other volume of the fluid path between the vials and transfer apparatus 6 will be minimized to encourage transfer of the maximum percentage of the drug to the injection device 7.

Figure 48:
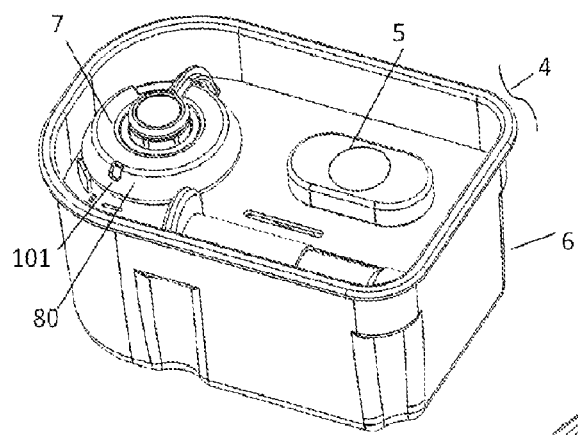
FIG. 48 is a perspective view of a dual vial system with the volume controller removed and the vial holder depressed into the transfer apparatus to start the mixing and transfer process.
Figure 49:
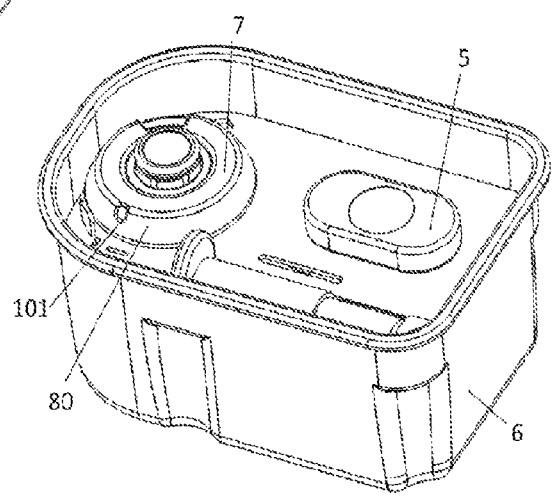
FIG. 49 is a perspective view of a dual vial system after completion of the mixing and transfer process, filling of the injection device and release of the injection device removal interlock.
Figure 50:
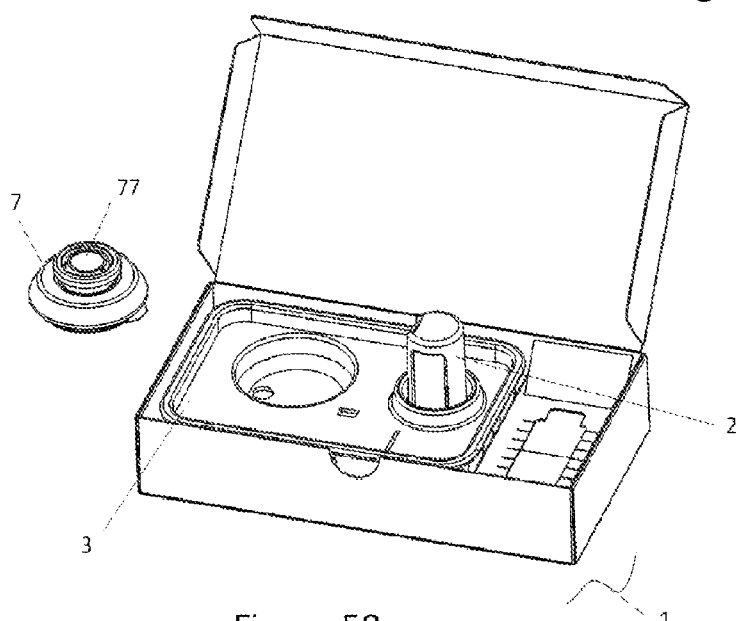
FIG. 50 is a perspective view of the single vial system with the injection device filled and removed from the package.

Referring to FIGS. 48-50, once the required dose volume has been delivered to the injection device 7, there is a clear area or other indicator 80, 101 in the injection device 7 to allow the user to view the mixed solution to verify complete mixing. Ideally, the user could view the entire drug volume within the injection device 7. There could also be an indicator 101, such a relative fill gage, to show that the correct dose had been delivered to the injection device 7. Completion of the mixing and transfer to the injection device 7 would then 'unlock' the injection device 7 and allow it to be removed from the transfer apparatus 3, 6 or injection device docking station. The injection device 7 may indicate to the user that it is in a ready state with the button 77 in the up or ready position and the indicator window 80, 101 showing the injection device is full.

Referring to FIG. 50, the user may disconnect the injection device 7 from the transfer apparatus 3 by twisting or pulling the injection device 7 off of the transfer apparatus 3. During removal of the injection device 7, an adhesive tape liner may be removed automatically exposing an adhesive surface on the bottom of the injection device that may be used to adhere the device to the patient's skin. Alternatively, the tape liner may have a tab that the user pulls to manually remove before adhering the device to the skin.

Figure 51:
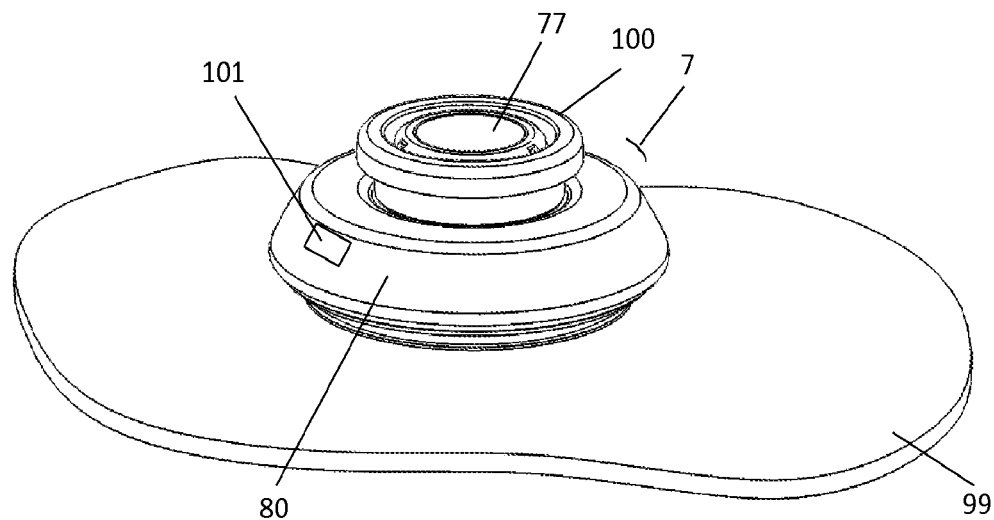
FIG. 51 is a perspective view of the injection device placed on the skin and the safety in place.

Referring to FIG. 51, the user attaches the injection device 7 to their skin 99. There may be an adhesive on the bottom of the injection device 7 that allows for adhesion to the skin 99 surface and hands-free operation. The adhesive may extend past the outline of the injection device to allow the user to firmly adhere the tape to the skin. Alternatively, the user may hold the injection device 7 against the skin 99 for the duration of the injection.

Figure 52:
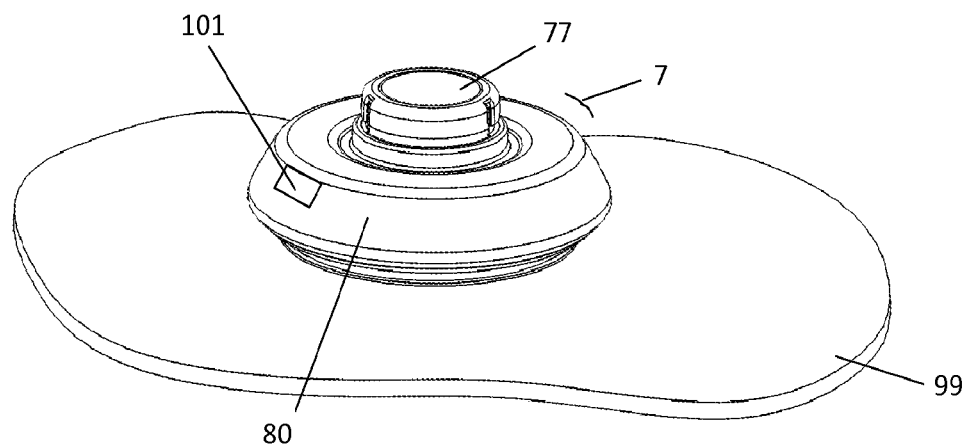
FIG. 52 is a perspective view of the injection device placed on the skin and the safety removed.
Figure 53:
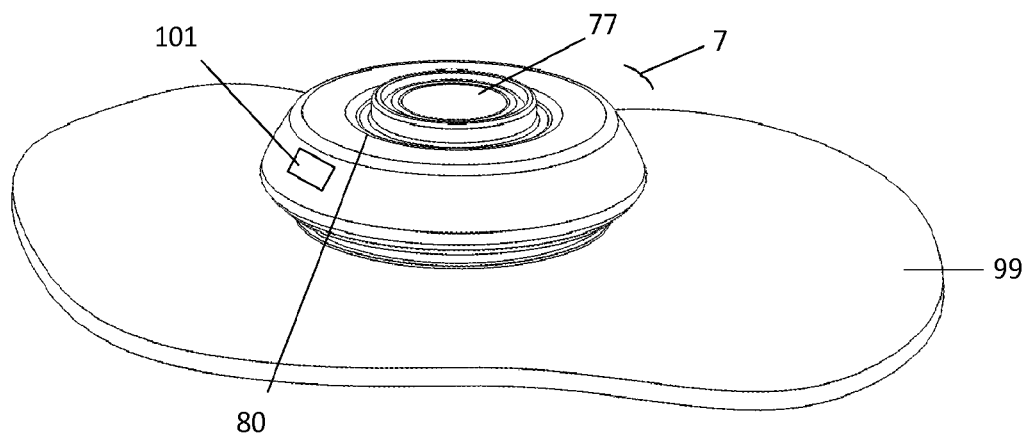
FIG. 53 is a perspective view of the injection device placed on the skin and the button depressed to fire start the injection.

Referring to FIGS. 51-53, the user removes the safety 100 and depresses the button 77 on the injection device 7 to start the injection. Once the button 77 on the injection device 7 is fully depressed, it is locked into place and the needle will be fully inserted into the patient and the injection device 7 will begin dispensing the injectable drug. The injection device 7 may alert the user that injection of the drug has started. This alert could be in the form of visual indictors, audible sounds, mechanical movements or a combination. The time of the injection could be in a range of a few seconds to several hours. The injection device 7 may indicate to the user that it is dispensing with the button 77 locked in the down position and indicator window 101 showing the injection device 7 is less than full. The injection device 7 preferably has a clear section 80 that allows the user to easily determine the amount of drug remaining in the injection device 7.

Figure 54:
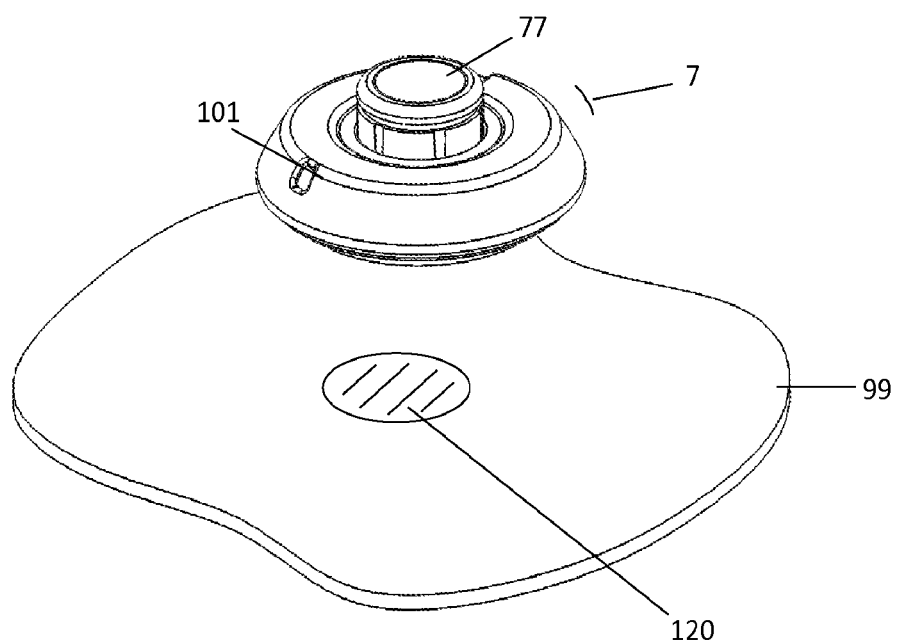
FIG. 54 is a perspective view of the injection device removed from the skin after the injection with the button in a locked up position and a bandage remaining on the skin.

Referring to FIG. 54, the user will be alerted when the injection of the drug is completed. This alert could be in the form of visual indicators, audible sounds, mechanical movements or a combination. The injection device 7 may indicate to the user that it is has completed dispensing with the button 77 moving to a locked up position with tactile and audible sounds and indicator window 101 showing the injection device is empty. At the end of the dispense, the needle will automatically retract into a locked position within the injection device 7.

Referring to FIG. 54, upon removal of the injection device 7 from the skin 99, a bandage 120 could release from the injection device 7 and remain on the skin surface 99. Upon removal from the skin 99, the injection device 7 will preferably be locked out, preventing non-destructive access to the needle or reuse of the injection device 7. The injection device 7 may indicate to the user that the full dose has been delivered. This indication could be in the form of a visual indictor, audible sound, mechanical movement or a combination.

In accordance with further aspects of the present subject matter, when administering an injection with a syringe and needle that is meant to be infused under the skin, it is desirable to know if the needle is properly placed within the skin or improperly placed within a blood vessel. It is common for a user performing an intradermal (ID), subcutaneous (SC) or intramuscular (IM) injection to aspirate the syringe by pulling back on the plunger to create a pressure drop within the syringe to see if any visible blood comes up the needle into the syringe. If blood is visualized, this means the tip of the needle is in a blood vessel. A number of injectable drugs meant for infusion under the skin specifically indicate not to inject into a blood vessel. Blood aspiration using a syringe and needle is a common technique and can be performed by anyone with adequate training. However, as more drugs are being presented in automatic injection devices, the ability to manual aspirate these types of systems does not exist. Once an injection device is placed on the skin and the needle is fired, there is no way for the user to know if the needle is properly placed within the skin or improperly placed within a blood vessel. Accordingly, there exists a need for a blood aspiration device and method within an automatic injection device.

Figure 55:
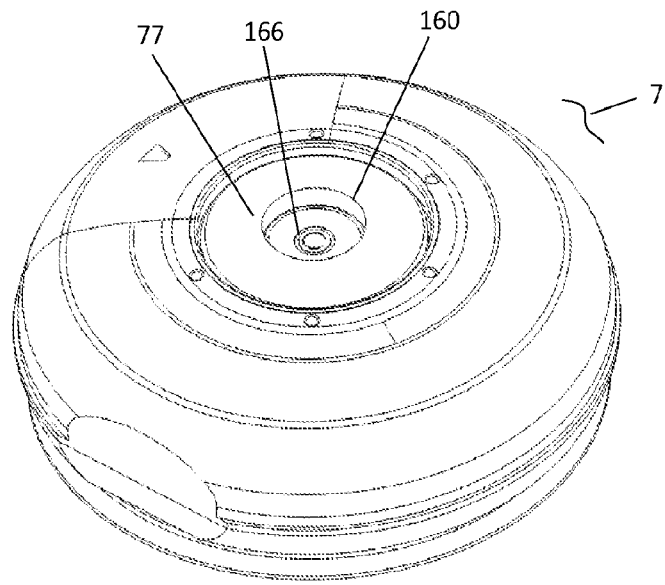
FIG. 55 is a perspective view of injection device embodying the present subject matter.
Figure 56:
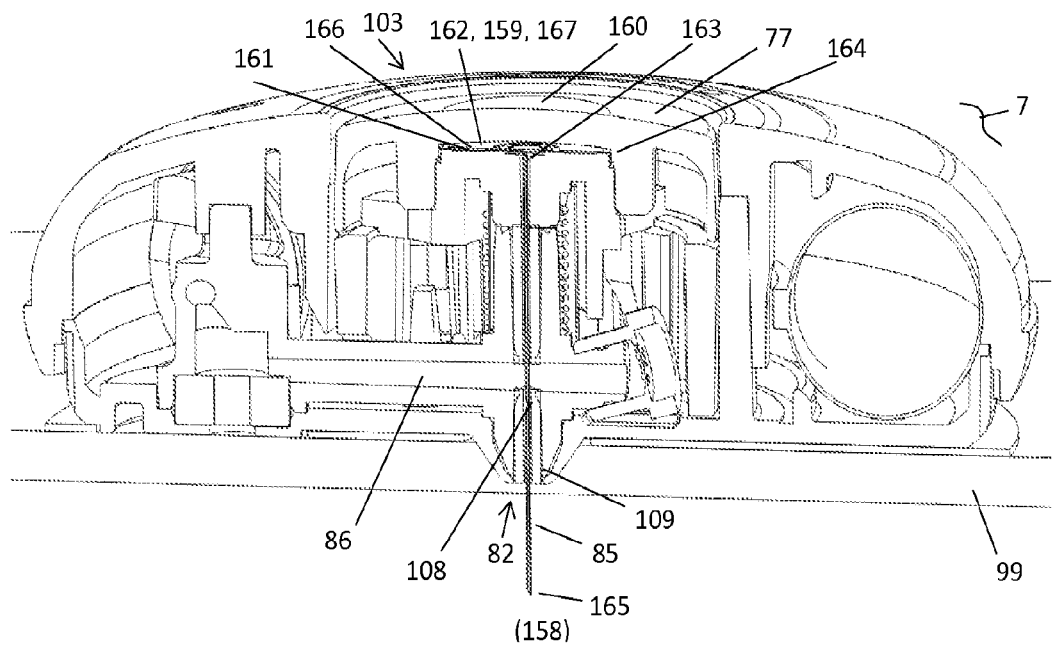
FIG. 56 is a cross-section of FIG. 55 showing the injection device with the button in the first position.

Referring to FIGS. 55-56, the injection device 7 may have a needle 85 with a side-hole 108 in operative engagement with the button 77 slidable within a septum 109 advancing into the skin 99. The button 77 may have a viewing window 160 on the button top 103 that is in fluid communication with the proximal end 161 of the needle 85. The button top 103 may include a cavity 162 for blood 159 to accumulate and be seen through the button window 160 by a user. The cavity 162 may include a center hole 163 that allows fluid communication with the proximal end 161 of the needle 85 via needle lumen 165. The outer walls 164 of the cavity 162 are formed by the button top 103. Additionally, a portion of the outer walls 164 may include a hydrophobic filter 166. In this configuration, the proximal end 161 of the needle 85 is at atmospheric pressure. If fluid 14 or blood 159 travel up the internal lumen 165 of the needle 85, it exits the proximal end 161 of the needle 85 and fills the cavity 162. The air 167 in the cavity 162 is easily displaced through the hydrophobic filter 166 until all of the air 167 has been displaced from the cavity 162 and it is full of fluid 14 or blood 159. At this point, the flow of fluid 14 or blood 159 stops as the fluid 14 or blood 159 cannot penetrate the hydrophobic filter 166 and can be easily viewed through the window 160 of the button top 103 by the user.

Referring to FIG. 56, upon actuation (or depression) of the button 77, the needle 85 and button 77 travel to a first position or depth as shown in FIG. 56. In this first position or depth, the side-hole 108 is covered by the septum 109 and therefore the internal lumen 165 of the needle 85 is not in communication with the fluid pathway 86 of the dispense port 82. If the needle tip 107 in the first position or depth is within a blood vessel 158, the pressure in the vessel 158 will advance blood 159 up through the internal lumen 165 and to the proximal end 161 of the needle 85, filling the cavity 162 with blood 159 which may be seen through the button window 160 on the top 103 of the button 77 thus providing a method for determining if the injection device 7 needle 85 is in a blood vessel 158.

Figure 57:
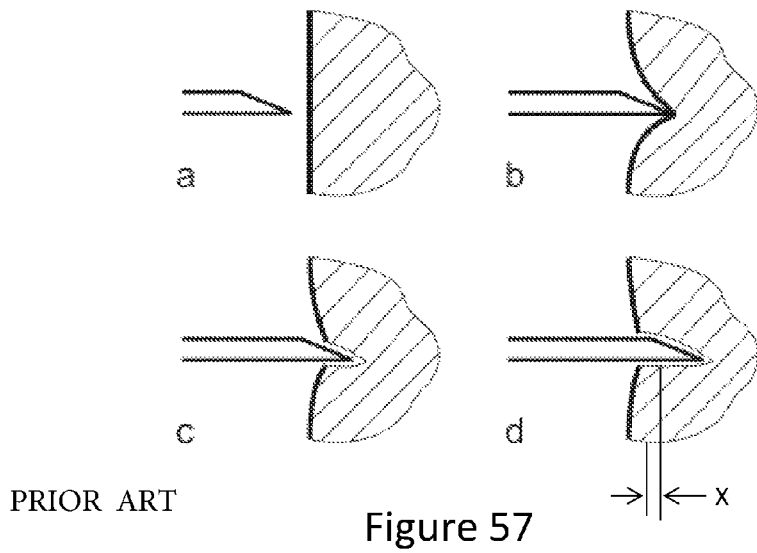
FIG. 57 is an illustration (Van Gerwen, D. J. *Needle-Tissue Interaction by Experiment*. Ph.D. Thesis, Delft University of Technology, 2013. ISBN 978-94-6186-238-9, pg. 11) showing four stages of needle penetration into tissue including a.) no contact, b.) boundary displacement, c.) tip insertion and d.) shaft insertion.

Referring to FIG. 57, needle insertion into tissue can be generally divided into four stages. These include no contact, boundary displacement, tip insertion and shaft insertion. During boundary displacement, the tissue boundary in the contact area deflects under the influence of the load applied by the needle tip, but the needle tip does not penetrate the tissue. The boundary of the skin follows the tip of the needle up to a maximum boundary displacement point in the contact area as the needle tip starts to penetrate the skin. After the needle tip penetrates the skin, the shaft is inserted into the tissue. Even after tip and shaft insertion, the boundary of the skin surface in the contact area does not return to its original no contact state but remains displaced by a distance x. The amount of boundary displacement x is a function of several parameters including but not limited to needle diameter, needle tip geometry, needle shaft friction, needle insertion speed and physical skin properties. Boundary displacement x of the skin in the contact area is characterized in needle-based injection devices because it effects how much of the needle penetrates the skin and therefore reduces the actual needle penetration depth by the amount of boundary displacement x. If the boundary displacement x could be intentionally induced by stretching or preloading such as pushing the skin out at the contact site prior to needle tip insertion, there would be no additional boundary displacement by the needle tip or shaft during insertion and the needle tip depth could be predictably defined. The advantage of this intentional displacement is the amount of needle penetration into tissue would not be affected by variations in the boundary displacement x. Without intentionally inducing boundary displacement at the skin surface prior to needle tip insertion, the actual needle penetration depth into the skin is not specifically known because some of the needle length (depending on the abovementioned parameters) is outside the skin due to the naturally occurring boundary displacement x shown in FIG. 57. On the other hand, if the maximum boundary displacement could be induced at the contact site, the actual needle penetration depth would not change with the variations in the abovementioned parameters including needle diameter, needle tip geometry, needle shaft friction, needle insertion speed and physical skin properties.

Figure 58:
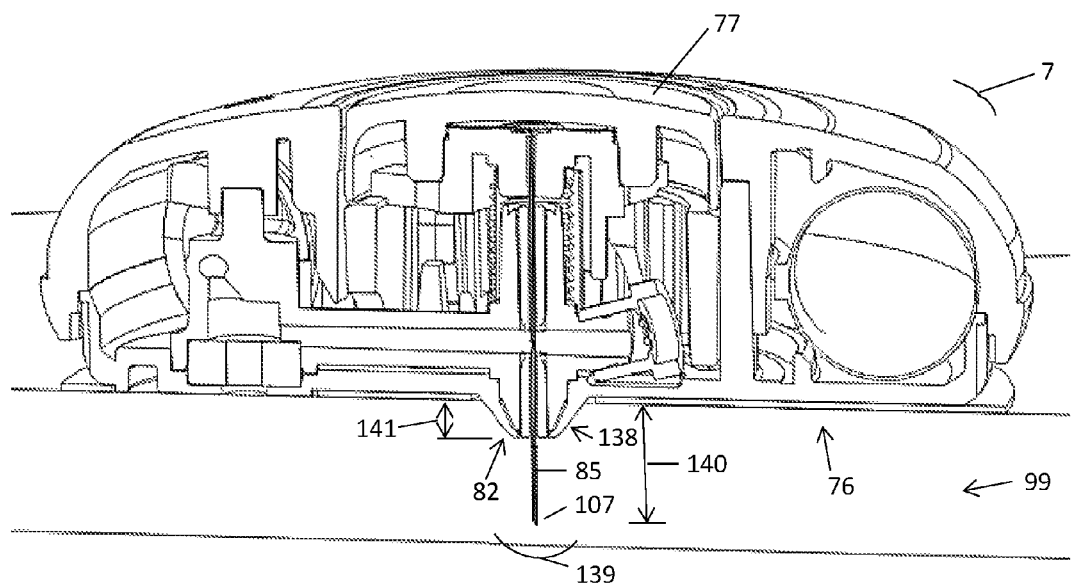
FIG. 58 is a cross-section of FIG. 55 showing an injection device with the button in a second position or dispense position.

Referring to FIG. 58, the injection device 7 may have a skin boundary displacement extension or structure, such as an underside surface 76 that includes an extension 138 at or around the dispense port 82 or as part of the dispense port 82. When the injection device 7 is attached to the skin 99, the extension 138 will protrude into the skin 99 surface resulting in displacement of the skin 99 in this contact area 139. During actuation of the button 77 from a pre-fire state to first position, the needle 85 advances out of the injection device 7 through the dispense port 82 and/or extension 138 into the skin 99 to start the dispense of drug. For the reasons described above, as the needle 85 advances out of the injection device 7, the tip of the needle 107 does not produce additional boundary displacement 141 (already intentionally induced by the extension 138) in the skin 99 at the contact area 139. Thus the actual needle penetration depth 140 into the skin 99 is better characterized and controlled.

Figure 59:
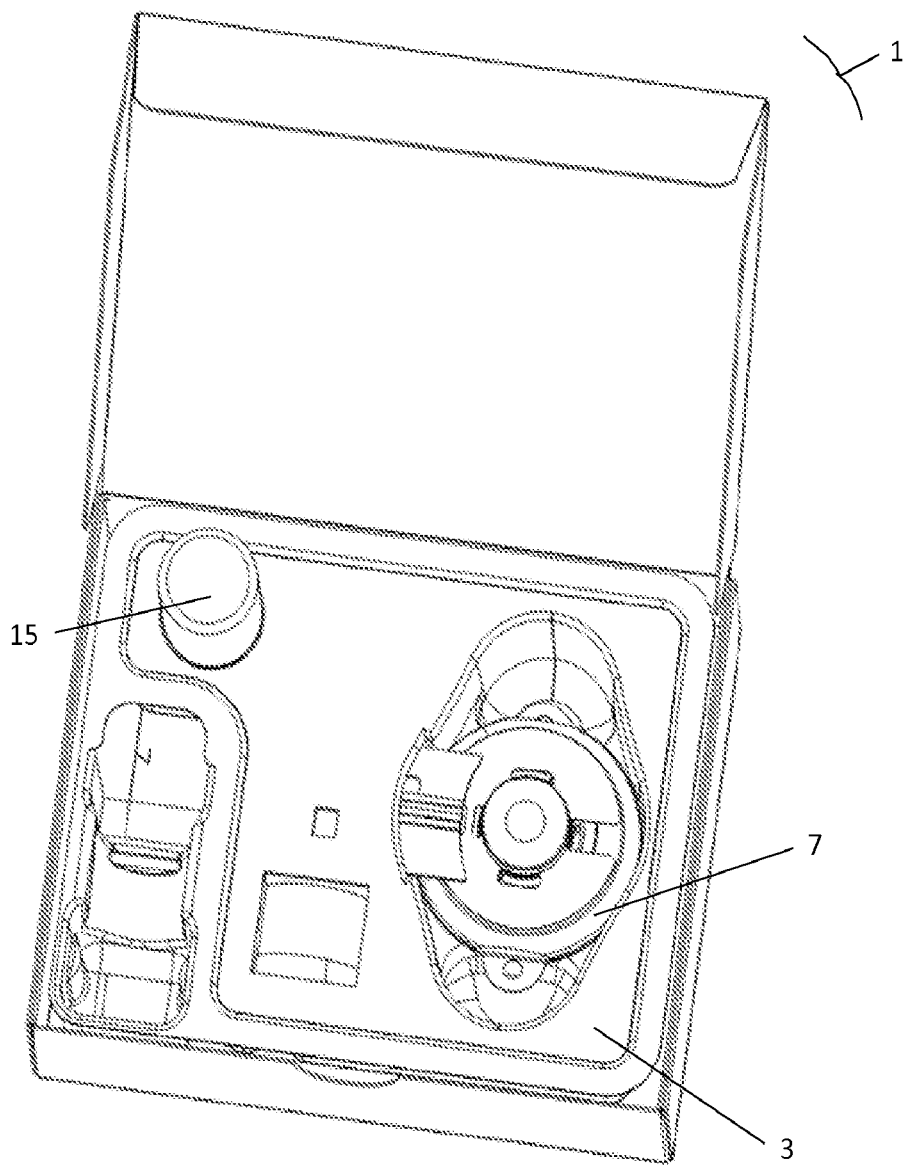
FIG. 59 is a perspective view of a single vial transfer system with the drug vial and injection device installed embodying the present subject matter.
Figure 60:
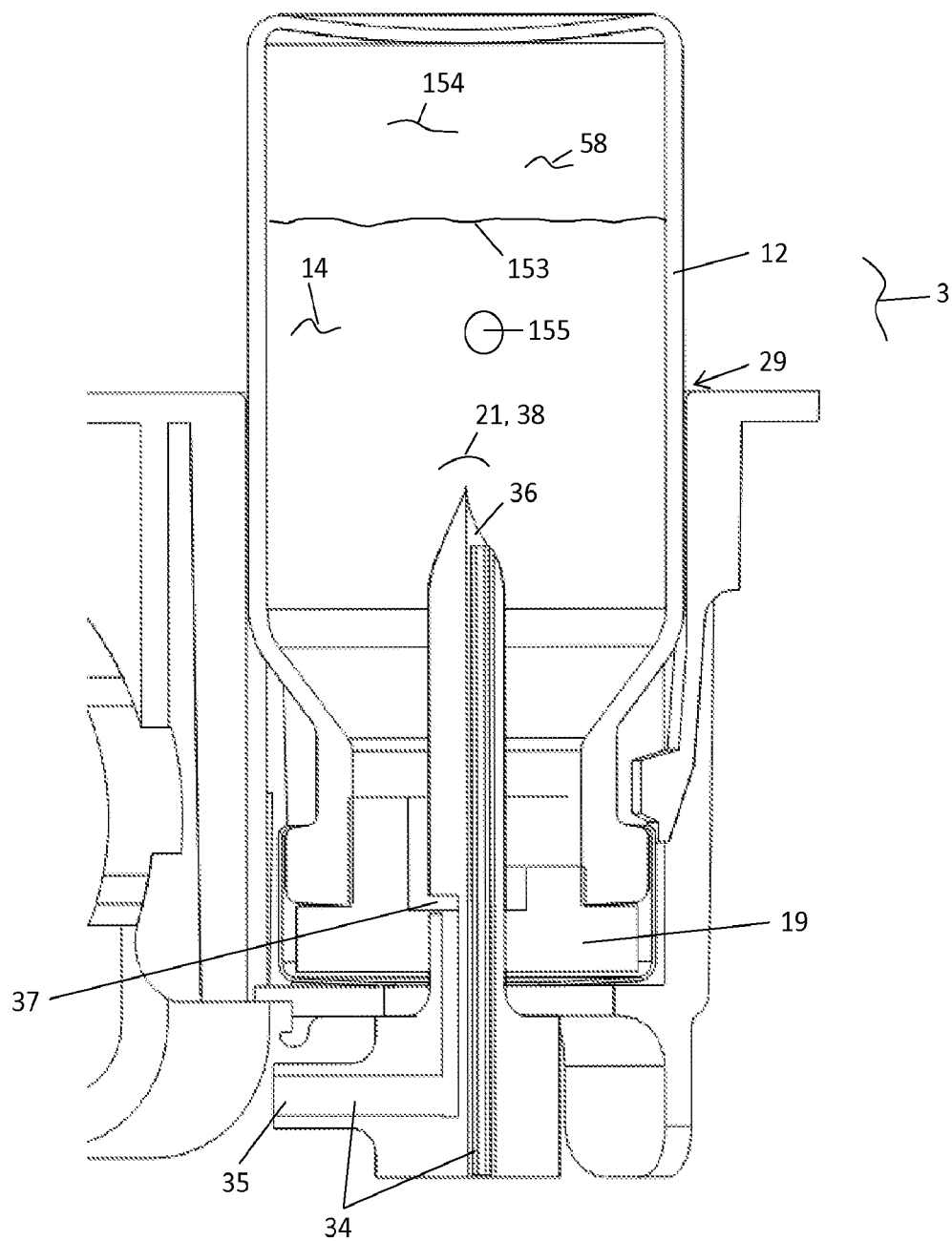
FIG. 60 is a cross-section of FIG. 59 with depicting an aspect of the vial holder area showing the drug vial, a vial access member and an extension member in the down position.

Referring to FIG. 60, the vial access member 21 of the transfer apparatus 3 may be comprised of multiple lumens, such as multi-lumen tubes 34 to communicate with the internal fluid pathways 35 of the transfer apparatus 3. The vial access member 21 preferably comprises one inlet tube 36 allowing air or fluid to enter the vial 12 and one outlet tube 37 allowing for air or fluid to exit the vial 12. The lumen openings 38 in the vial access member 21 can be oriented so the inlet tube opening 36 is above the output tube opening 37 when the vial is inverted and attached as illustrated, for example, in FIG. 59. This orientation allows for introduction of air or liquid through the upper inlet tube 36 and output of the vial contents 14 through the lower output tube 37. Further, the outlet opening 37 may be positioned near the lower end bottom of the inverted vial 12, adjacent to the septum 19 to encourage the entire contents 14 of the vial 12 to enter the outlet port 37 and be removed from the vial 12. Once the vial 12 is installed in the vial holder docking area 29 in the transfer apparatus 3, the vial access member 21 is able to access the contents 14 of the vial 12. When the transfer apparatus 3 begins to withdraw the contents 14 from the vial 12 through the outlet tube 37, a pressure drop 154 occurs in the vial 12. This pressure drop 154 causes displacement air 58 to be drawn into the vial 12 through the inlet opening 37 of the vial access member 21 to replace the fluid 14 that is being withdrawn. In some cases depending on the amount of injectable 14 in the vial 12, the liquid level 153 in the vial 12 may be above the vial access member 21 and specifically above inlet tube opening 37. When air 58 is drawn into the vial 12 through the inlet opening 37, it creates a bubble 155 in the fluid 14. Buoyancy causes the bubble 155 to migrate to the top of the vial 12 with the existing air 58. In some injectables 14, it is undesirable to introduce air bubbles 155 into the solution. This causes more bubbling, frothing and or foaming within the fluid 14.

Figure 61:
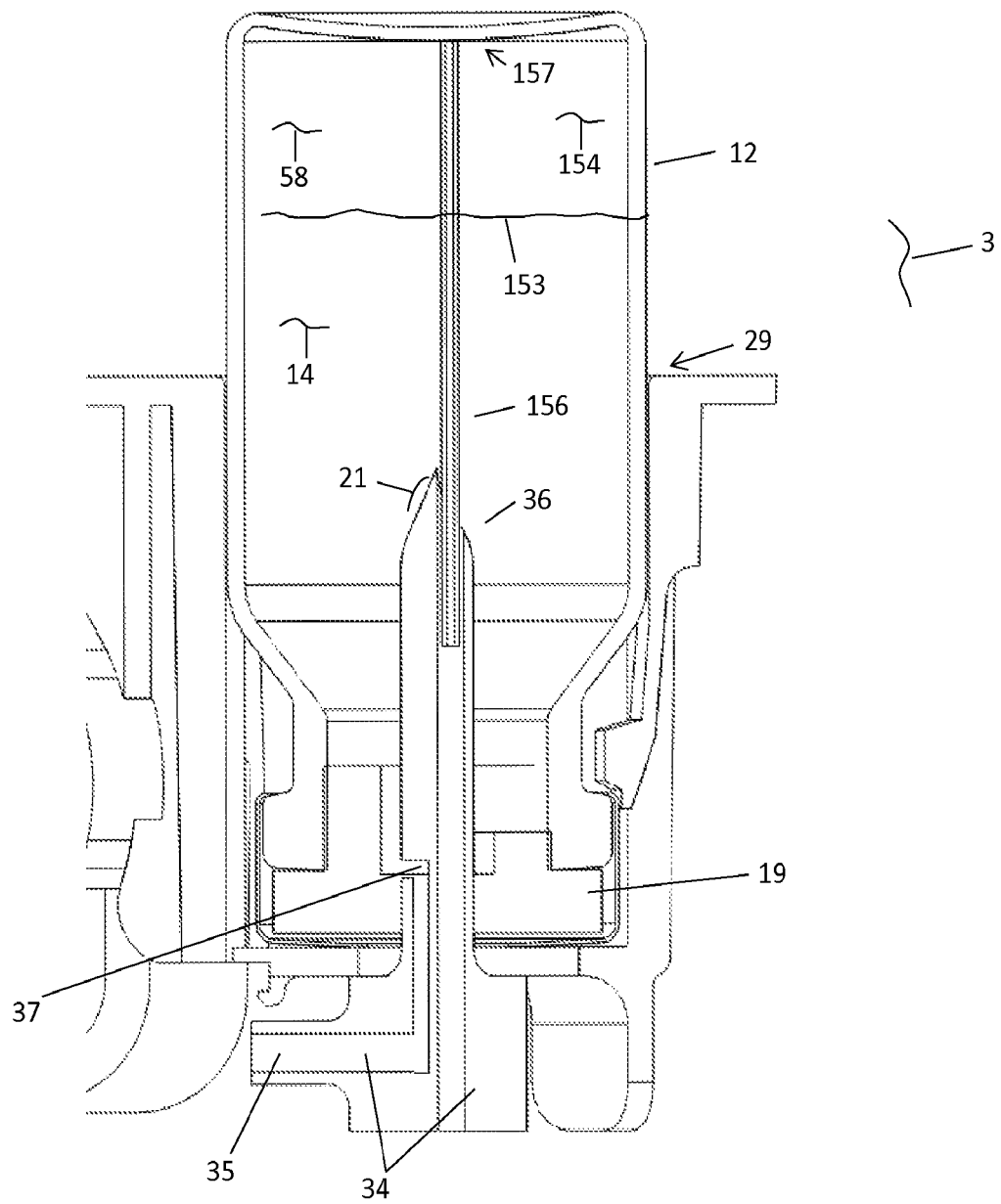
FIG. 61 is a cross-section of FIG. 59 depicting an aspect of the vial holder area showing the drug vial, a vial access member and an extension member in the up position.

Referring to FIG. 61, an extension member 156 could be slideably moveable within the inlet opening 36 of the vial access member 21. The outer diameter of the extension member 156 may be close fitting to the inner diameter of the inlet opening 36. The extension member 156 may have an inner diameter that allows air 58 to pass through it. When air 58 is drawn into the vial 12 through the inlet vent opening 36 due to the pressure drop 154 in the vial 12, the air 58 first pushes the extension member 156 like a piston within the inlet opening 36. The extension member 156 is sufficiently long as to not come out of the inlet opening 36. The extension member 156 continues to slide through the inlet opening 36 until the end of the extension member 156 stops at the top 157 of the vial 12 well above the liquid level in the vial 153. The top of the inverted vial 12 acts as a stop to the extension member 156. The tip of the extension member 156 may be tapered as to not block flow through its inner diameter when in contact with the top of the inverted vial 12. Air 58 continues to travel through the inner diameter of the extension member 156 until all of the fluid 14 in the vial 12 has been withdrawn from the vial 12 through the outlet tube 37. As previously mentioned, the outer diameter of the extension member 156 is close fitting to the inlet opening 36 inner diameter as to not allow air to leak between this interface. The extension member 156 insures that no air 58 is introduced into the liquid 14 within the vial 12 causing bubbles 155.

Figure 62:
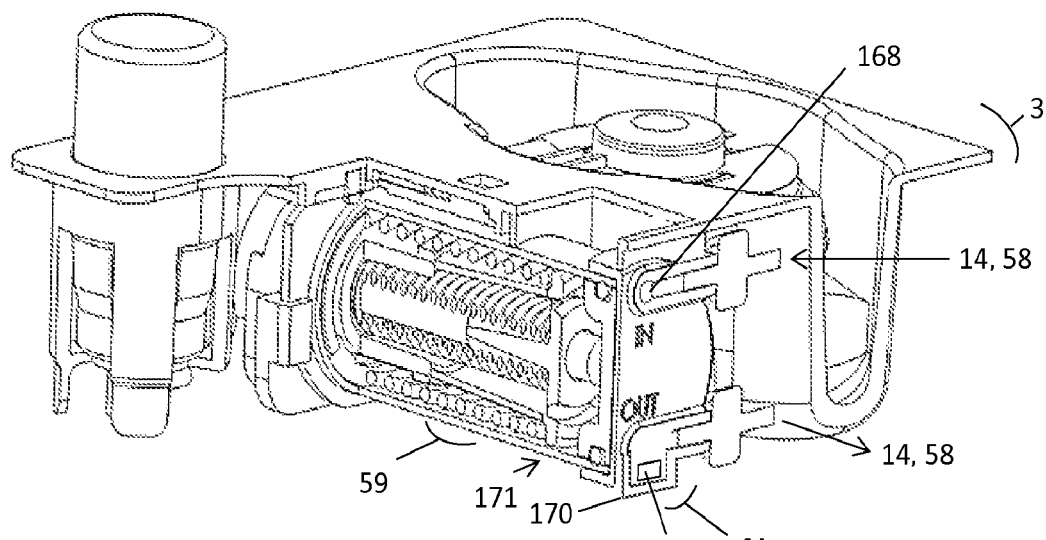
FIG. 62 is a cross-section of FIG. 59 with the box and tray removed and depicting an aspect of the pressure chamber and fluid passageways.

Referring to FIG. 62, the pressure chamber 59 may be configured with an inlet port 168 used to bring fluid 14 and air 58 into the chamber. Additionally, the pressure chamber 59 may be configured with an outlet port 64 used to expel fluid 14 and/or air 58 out of the chamber 59. These ports 168, 64 may be positioned off-center of the pressure chamber 59 to help control the sequence of liquid 14 and air 58 introduction into and/or expulsion from the pressure chamber 59. As previously mentioned, the outlet port 64 of the pressure chamber 59 may be oriented below the inlet port, during the process of expelling the liquid 14 from the pressure chamber 59, all of the liquid 14 is expelled first then the remaining air 58 is expelled last any air in the chamber 59 would be oriented to the top of the pressure chamber 59. Additionally, as shown in FIG. 62, the exit port profile 169 may be configured in a non-circular shape to further encourage the entire liquid contents 14 of the pressure chamber 59 to enter the outlet port 64 and be removed from the pressure chamber 59 prior to removal of air 58 from the pressure chamber 59. Additionally, as shown in FIG. 62, a portion 170 of the outlet port 64 may be positioned below the surface 171 of the pressure chamber 59. This may act as a trap to further encourage the entire liquid contents 14 of the pressure chamber 59 to enter the outlet port 64 and be removed from the pressure chamber 59 prior to removal of air 58 from the pressure chamber 59.

Figure 63:
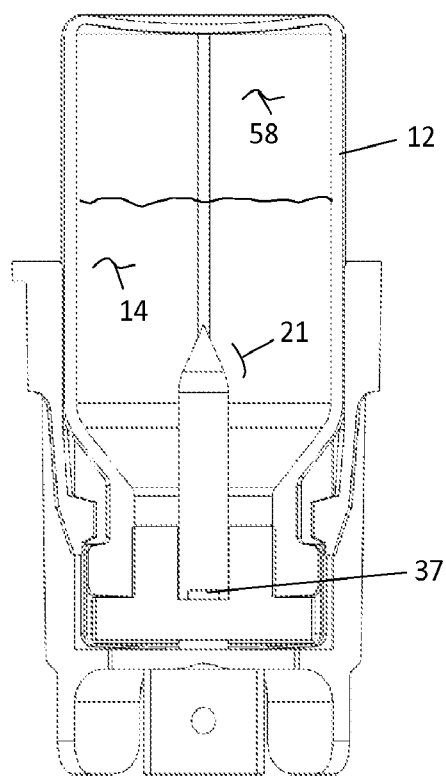
FIG. 63 is a cross-section of FIG. 59 depicting an aspect of the vial holder area showing the drug vial, the vial access member and outlet opening.

Referring to FIG. 63, when liquid 14 is removed from a vial 12 using a vial access member 21, only fluid 14 through the outlet opening 37 is removed until the liquid level 153 drops to the top of the outlet opening 137. At this point, a mixture of liquid 14 and air 58 will be removed. Referring to FIG. 63, the vial access member 21 may additionally have an outlet opening 37 configured in a non-circular shape such that the opening height is reduced and the opening width is increased to further allow for more liquid content 14 of the vial 12 to enter the outlet port 37 and be removed from the vial 12 prior to removal of air 58 from the vial 12.

Figure 64:
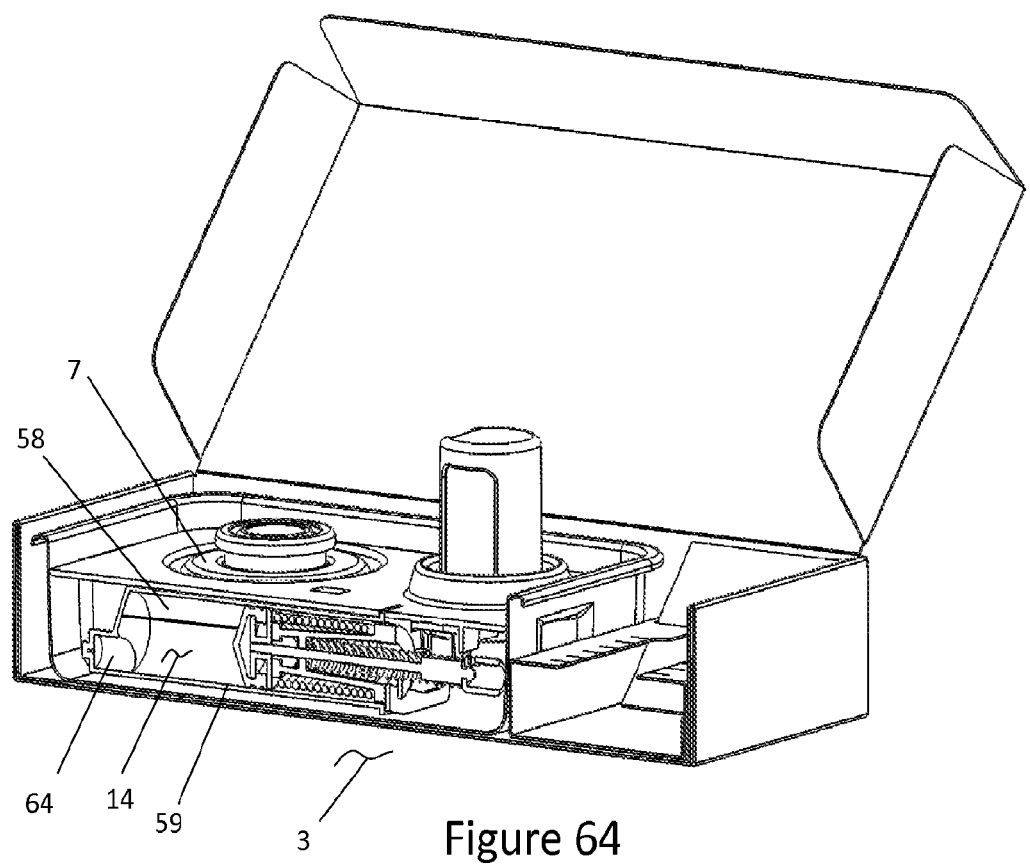
FIG. 64 is a cross-section of a single-vial system including the single vial holder, transfer apparatus and injection device system.
Figure 65:
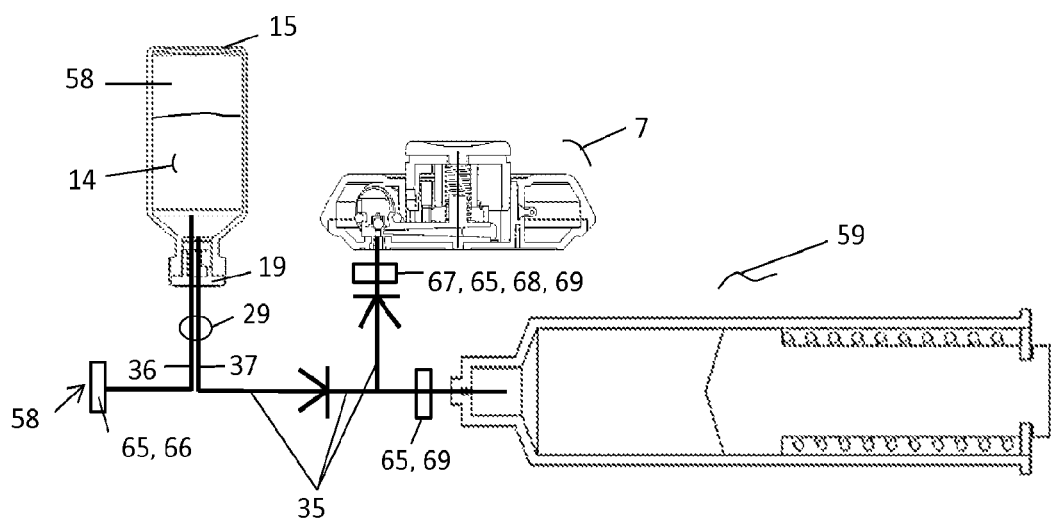
FIG. 65 is a schematic of an alternative embodiment of the single vial transfer system in FIG. 64 with a drug vial, a transfer apparatus with a first variable pressure chamber, an injection device including the fluid pathways with check valves and flow restrictors.

Referring to FIGS. 64 and 65, the combination of hydrophobic 68 and hydrophilic 69 filters in the fluid pathway 35 between the vial 15 and the injection device 7 may preferably allow for filtering of drug 14 and removal of air 58 during the transfer process. These filters may be separate components or combined into one component. Each filter may be constructed from different materials including but not limited to Mixed Cellulose Ester (MCE), Polyvinylidene Difluoride (PVDF), Polytetrafluoroethylene (PTFE), Nylon and polyethersulfone (PES). Each filter may have a range of pore sizes from 0.22 to 3 micron. Each filter may have a coating to make it hydrophilic or hydrophobic.

When administering an injection that is meant to be infused under the skin, a common reaction is infusion site swelling. This reaction is particularly pronounced in single subcutaneous sites where the infusion volume is high and/or the infusion rate is fast. When these infusions are administered with a syringe and needle or administration set, infusion site swelling has no consequence to the injection device. However, as more drugs are being presented in automatic injection devices that are adhered and worn on the body during the infusion, site swelling presents a challenge in keeping the automatic injection device secured to the body. In particular, the lump or bulge formed by the infused solution at the skin surface may dislodge an automatic injection device from the infusion site if the adhesive on the injection device is not properly designed. Accordingly, there exists the need for an automatic injection device with properly designed adhesive that allows for bulging at the injection site without compromising the adherence of the device to the patient.

Figure 66:
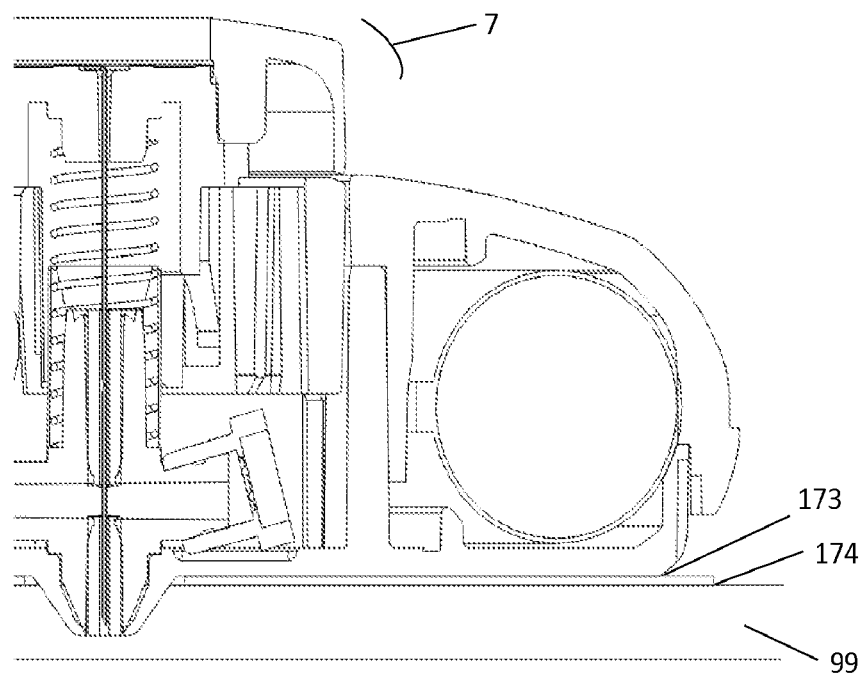
FIG. 66 is a cross-section of FIG. 55 showing adhesive/device and adhesive/skin interfaces.

Referring to FIG. 66, there are two interfaces related to adhering the injection device 7 to the skin 99. The first is the adhesive/device interface 173 and the second is the adhesive/skin interface 174.

Figure 67:
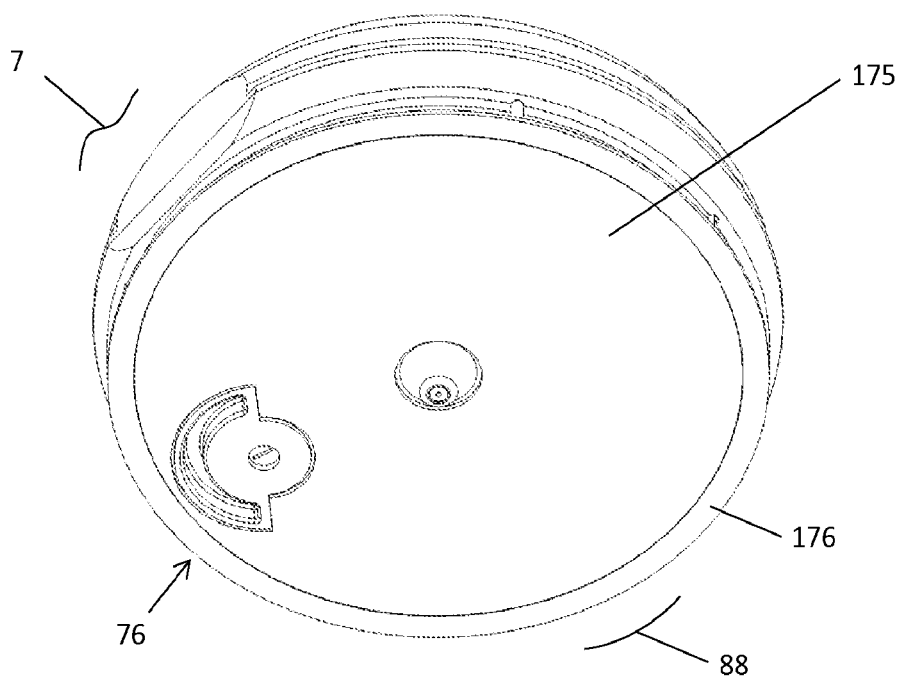
FIG. 67 is a perspective view of the bottom of an injection device showing the different zones of the adhesive.

Referring to FIG. 67, the adhesive 88 could be configured on the injection device 7 with at least two zones. The first zone 175 may include a permanent bond using mechanical or chemical means between the adhesive 88 and the injection device 7 and preferably be positioned within the perimeter of the injection device 7. The second zone 176 may be configured to be detachable or unattached from the injection device 7 and preferably be adjacent and on the outside (e.g., radially outward) of zone 1.

Figure 68:
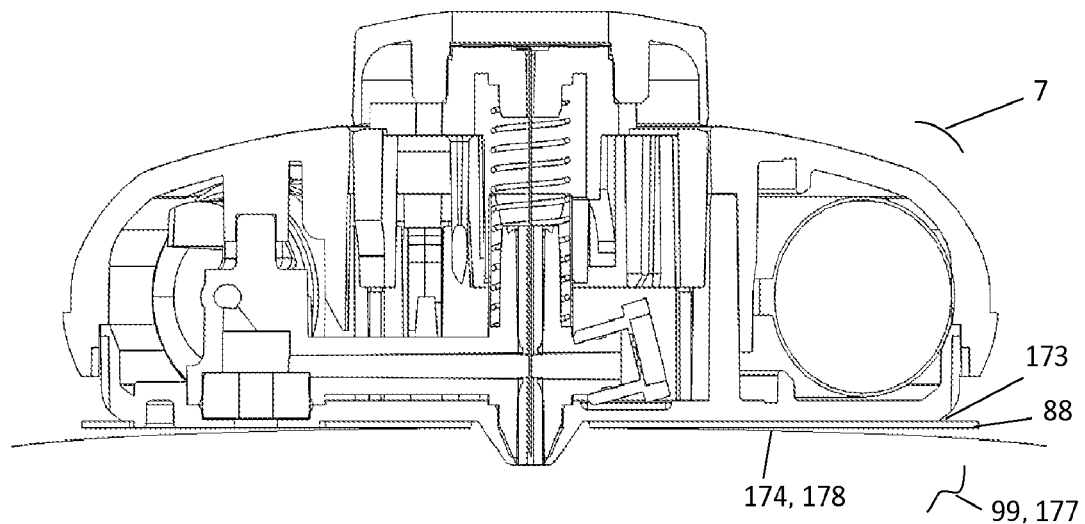
FIG. 68 is a cross-section of FIG. 55 showing bulging tissue on a device with permanently attached adhesive.

Referring to FIG. 68, if the adhesive 88 were completely attached to the bottom 76 of the device 7, during a tissue bulge 177 event the adhesive 88 at the adhesive/skin interface 174 would start to peel from the skin 99 because this interface 174 is weaker than the adhesive/device interface 173. This is demonstrated on a bulging surface in FIG. 68. This may result in the injection device 7 becoming dislodged from the skin surface 99 and falling off the patient.

Figure 69:
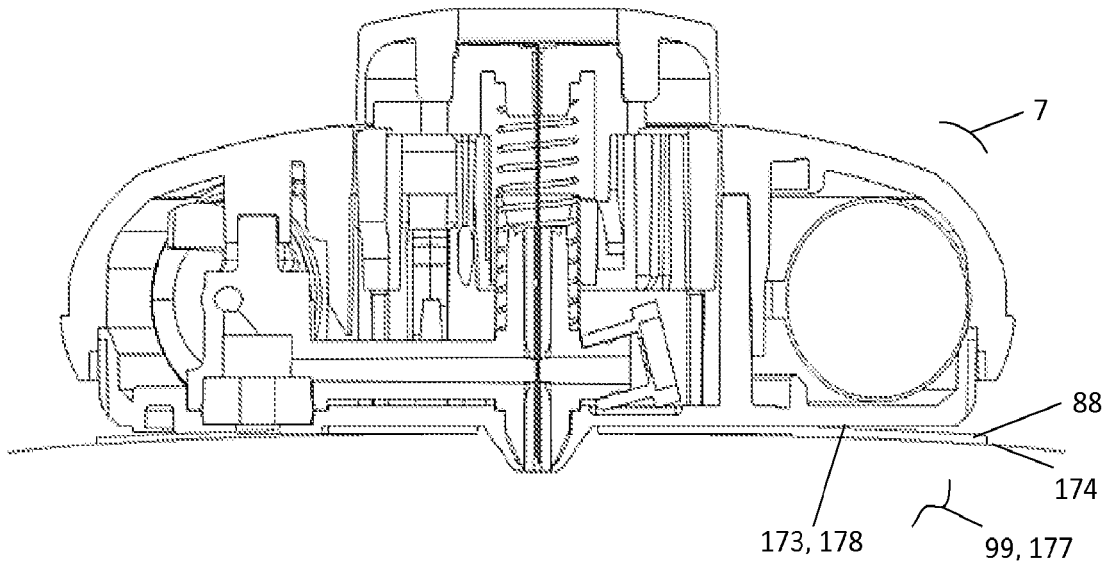
FIG. 69 is a cross-section of FIG. 55 showing bulging tissue on a device with multi-zone attached adhesive.

Referring to FIGS. 67 and 69, instead of permanently attaching the adhesive 88 completely to the bottom 76 of the injection device 7 as shown in FIG. 68, the adhesive 88 could be configured on the injection device 7 with the abovementioned zones 175, 176. During a tissue bulge event 177 in this configuration, the adhesive 88 in zone two 176 would detach from the injection device 7 and be firmly attached to the skin 99 surface at the adhesive/skin interface 174. This would allow for transfer of the peel edge 178 from the adhesive skin interface 174 to the adhesive/device interface 173 effectively creating a strain relief at the adhesive/skin interface. The adhesive/device interface 173 may be designed to be much stronger and prevent injection device 7 separation from the skin surface 99.

When performing self-injections with automatic injection devices, protecting the user from accidental needle sticks is a beneficial requirement for the device. Typically, the needle is retracted within the device before and after use, preventing the user from accessing the needle. However, during the injection, the needle is extended outside of the device. If the automatic injection device were body worn and inadvertently fell off the user during the injection, the needle would be exposed creating a potential needle stick hazard to the user. Accordingly, there exists the need for an automatic injection device with a skin dislodgement sensor to automatically retract a needle if the device becomes dislodged from the skin during the injection.

Figure 70:
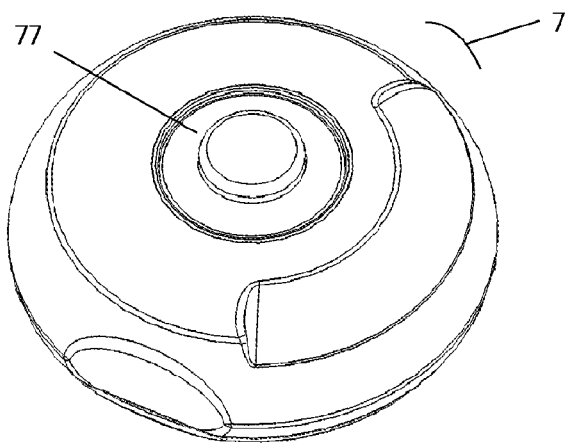
FIG. 70 is a perspective view of the top of an alternative injection device.
Figure 71:
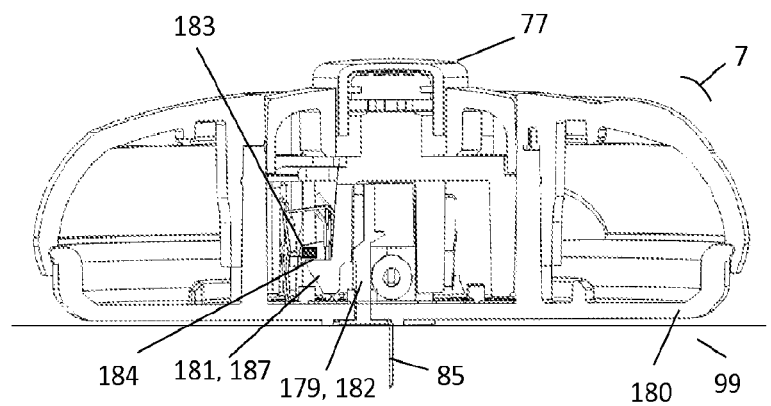
FIG. 71 is a cross-section of FIG. 70 showing a dislodgment sensor non-engaged and the needle locked in the dispense position.
Figure 72:
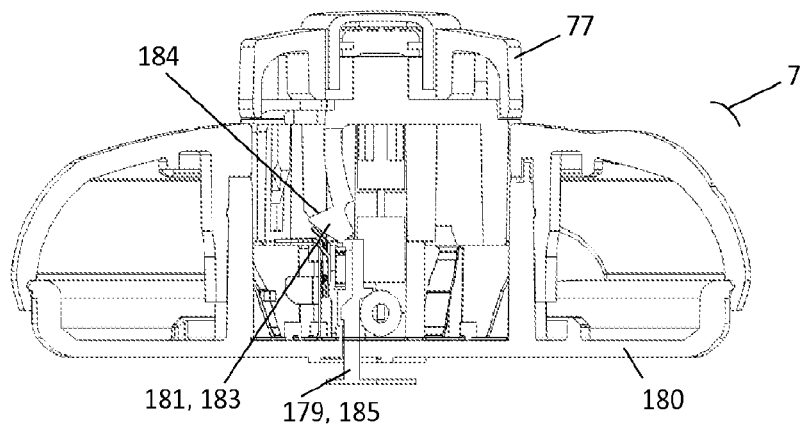
FIG. 72 is a cross-section of FIG. 70 showing a dislodgment sensor engaged and the needle and button retracted to post-fire position.

Referring to FIG. 70-72, a skin dislodgement sensor 179 may be in operative engagement with a flexible latch 181 of the button 77 and slidable within the lower housing 180 of the injection device 7. Referring to FIG. 71, when the injection device 7 is attached to the skin surface 99, the skin dislodgement sensor 179 is forced into a first or up position 182 inside the injection device 7. When the button 77 is actuated to a fired state or second position or dispense position (exposing the needle 85), the flexible latch 181 is forced into a lock position 187 by the skin dislodgement sensor 179 under the latch board 183. The latch board 183 holds the button 77 at the latch board surface 184 on the button 77 down in the fired state or dispense position until the end of dispense. At the end of dispense, the latch board 183 translates away from the latch board surface 184 on the button 77, allowing the button 77 and needle 85 to retract to a post fire position where the needle 85 is contained within the injection device 7. Referring to FIG. 72, in the event that the injection device 7 becomes dislodged from the skin surface 99 during injection, the skin dislodgement sensor 179 extends to a second or down position 185 out of the injection device 7. This allows the flexible latch 181 to spring back to an unlocked position and disengage from the latch board 183. This allows the button 77 and needle 85 to retract to a post fire position where the needle 85 is contained within the injection device 7.

When performing self-injections with a syringe and needle, users may have the need to temporarily stop or pause the injection due to acute pain or irritation at the injection site. This pause in flow of injectable into the injection site, accomplished by removing pressure on the plunger rod of the syringe, helps to reduce the pain at the injection site by allowing the injectable fluid bolus more time to diffuse into the surrounding tissue and thus reducing the local pressure and associated pain and irritation. However, as more drugs are being presented in automatic injection devices, the ability to manually pause these types of automatic systems does not exist. Once an automatic injection device is placed on the skin and the cannula is introduced, there is no way for the user to pause the injection due to pain or irritation at the injection site. Accordingly, there exists a need for a user to be able to pause an automatic injection system.

Figure 73:
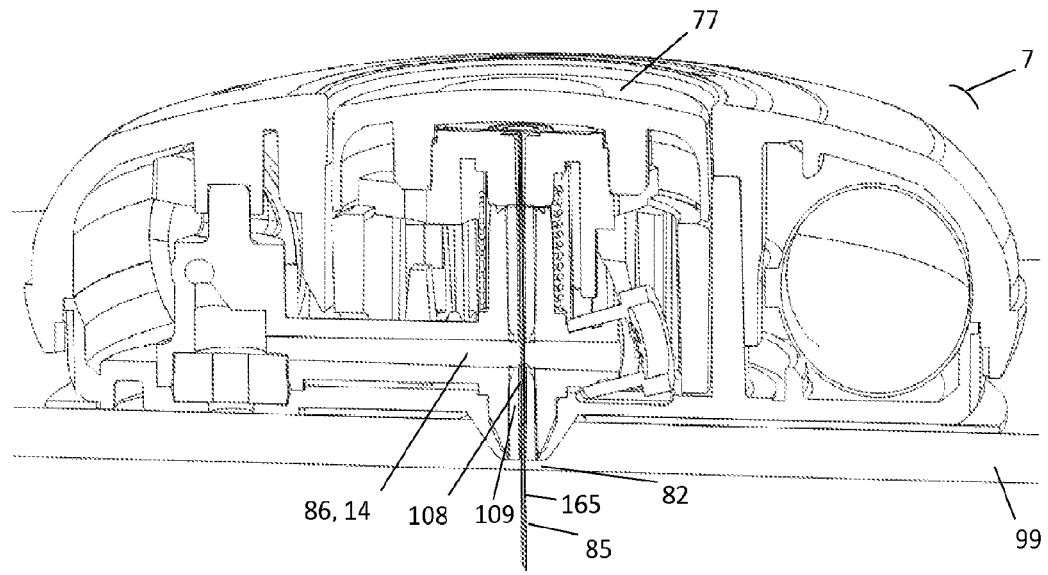
FIG. 73 is a cross-section of FIG. 55 showing an injection device with the button in the first position or pause position.
Figure 74:
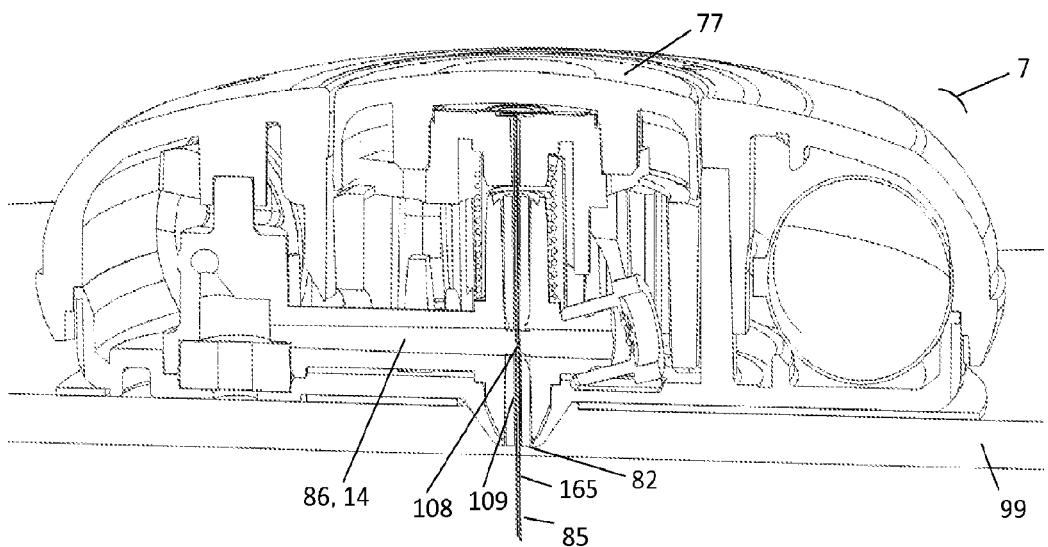
FIG. 74 is a cross-section of FIG. 55 showing an injection device with the button in a second position or dispense position.

Referring to FIGS. 73-74, upon actuation of the button 77, the needle 85 and button 77 travel to a first position or depth as shown in FIG. 73. In this first position or depth, the side-hole 108 is covered by the septum 109 and therefore the internal lumen 165 of the needle 85 is not in communication with the fluid pathway 86 of the dispense port 82. The button 77 may be intentionally held in this first position or depth to prevent flow of injectable 14 from the fluid pathway 86 into the side-hole 108 of the needle 85 and into the skin 99. As shown in FIG. 74, when the button 77 is released, the needle 85 and button 77 return to a second position or dispense position where the side-hole 108 is exposed to the fluid pathway 86 allowing the flow of injectable 14 from the fluid pathway 86 into the side-hole 108 of the needle 85 and into the skin 99 until the end of the injection. This action of pushing the button 77 to the first position or depth may be performed as many times a necessary during the entire injection.

Figure 75:
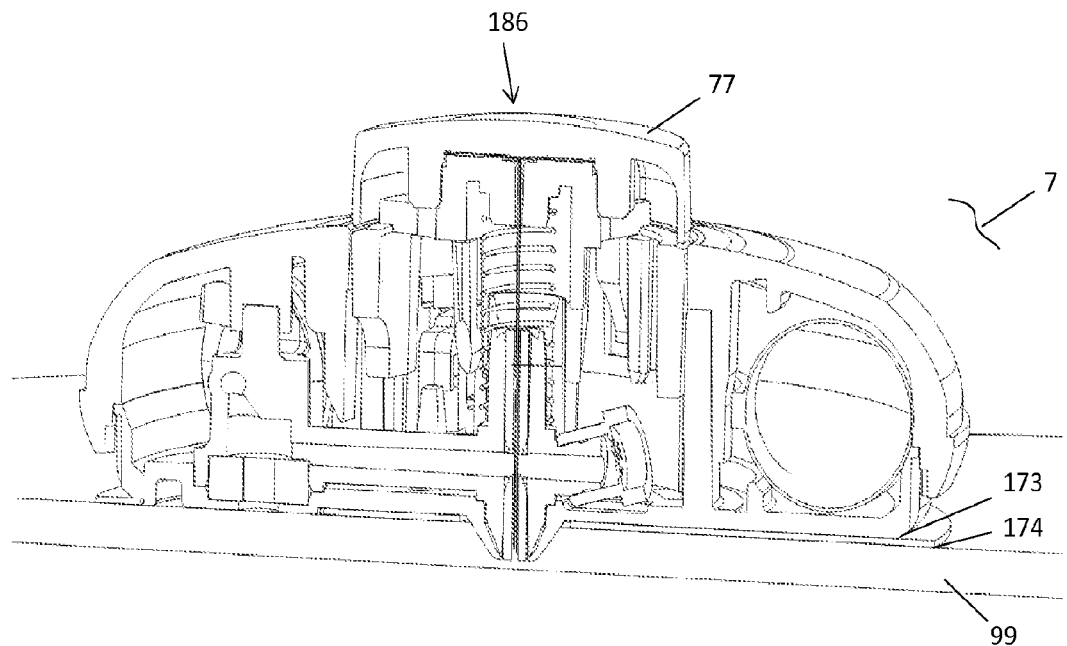
FIG. 75 is a cross-section of FIG. 55 showing an injection device with the needle retracted and the button in the up or pre-fire position.
Figure 76:
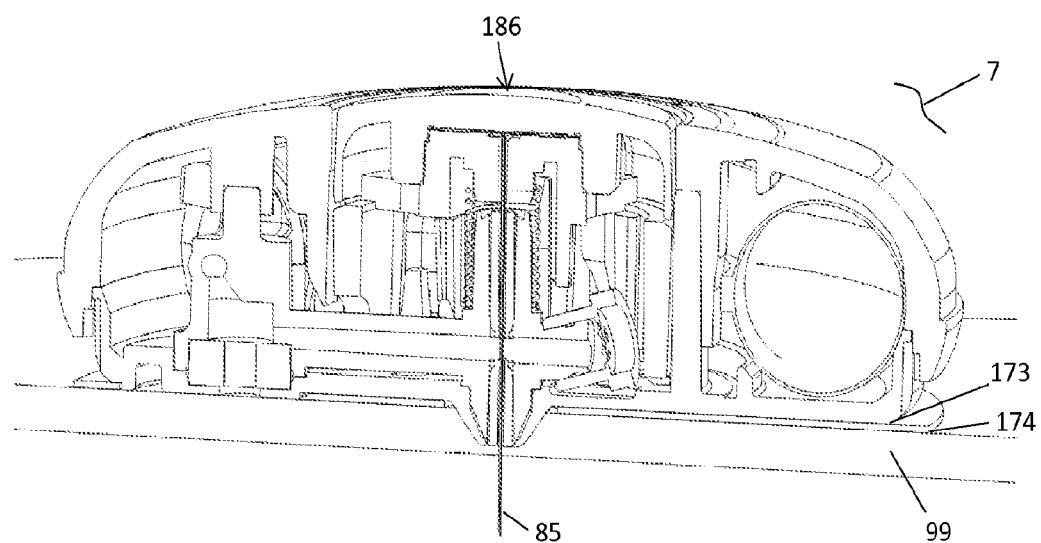
FIG. 76 is a cross-section of FIG. 55 showing an injection device with the button in a second position or dispense position.

Referring to FIGS. 75-76, the button 77 actuation force 186 is the transition load applied to the button 77 required to start displacement of the button 77 and needle 85 from a pre-fire position to a fired state or dispense position. Until this transition load is met, the force 186 applied to the button 77 is transferred directly to the injection device 7. Specifically, this load 186 may be transferred to adhesive skin interface 174 and/or the adhesive device interface 173 resulting in better securement of the injection device 7 to the skin surface 99 prior to actuation of the injection device 7.

Figure 77:
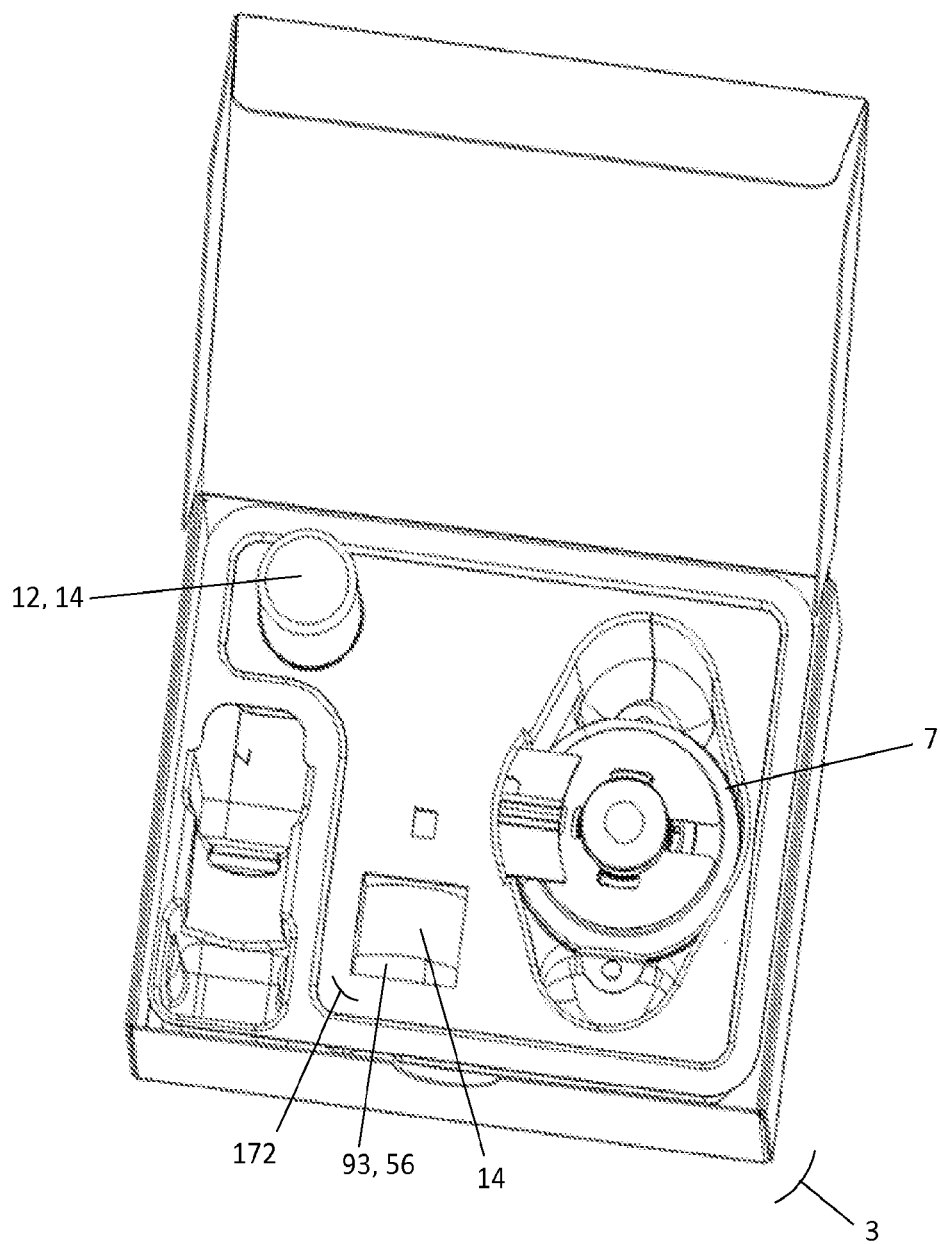
FIG. 77 is a perspective view of a single vial transfer apparatus.

Referring to FIG. 77, an indicator window 172 on the transfer apparatus 3 may be present to show that the transfer of fluid 14 and/or mixing is progressing. This indicator window 172 could be configured in the base of the transfer apparatus 3 and track the movement of the plunger 93 of the pressure chamber 56 within the transfer device 3. The indicator window 172 could be configured with a scale or other means to track the movement of the plunger 93. Alternatively, the plunger 93 could be configured with a different color to make it easy to track its movement in the indicator window 172. The combination of the indicator window 172 and plunger 93 could provide the progress of withdrawing fluid 14 from the vial 12 and filling of the chamber 56. The combination of the indicator window 172 and plunger 93 could also provide the progress of the transfer of fluid 14 from the chamber 56 to the injection device 7.

Figure 78:
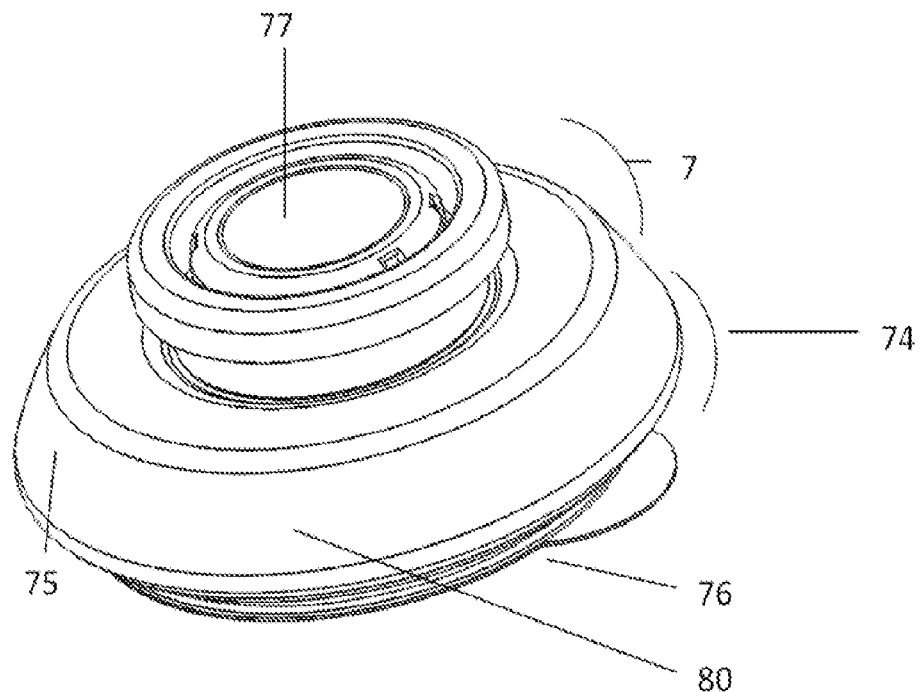
FIG. 78 is a perspective view of an injection device.
Figure 79:
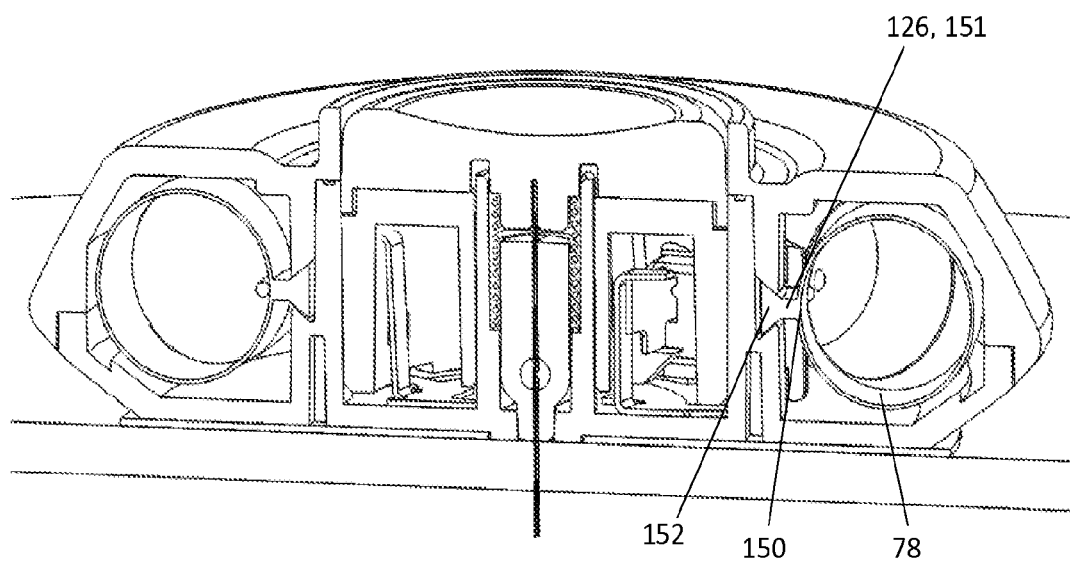
FIG. 79 is a cross-section of FIG. 78 showing an injection device with the button in a second position or dispense position.

Referring to FIG. 78-79, the arcuate expandable member 78 is positioned and/or will preferably expand in length in an arc shape. In the illustrated embodiment, the arc shape is induced by providing a less resilient area for example a thicker or relatively heavy wall thickness zone 126 which will result in less deflection of the expandable member in that zone and result in formation of an expanded arc shape. This heavy wall thickness zone 126 may be configured in any shape that will allow for the arc shape in the expandable member 78 during expansion. A preferred configuration for the heavy wall thickness zone 126 is to minimize its thickness or attachment 150 in the circumferential direction on the expandable member 78 wall and maximize the radial thickness or projection 151 away from the expandable member 78. This serves to urge the expandable member 78 to expand in an arc shape but also maximizes the amount of material along the circumference that is unaffected by the heavy wall thickness zone 126 for expansion. Additional features including but not limited to a T-shape may be configured to the end of the radial projection 152 to help urge the expandable member 78 into an arc shape.

Figure 80:
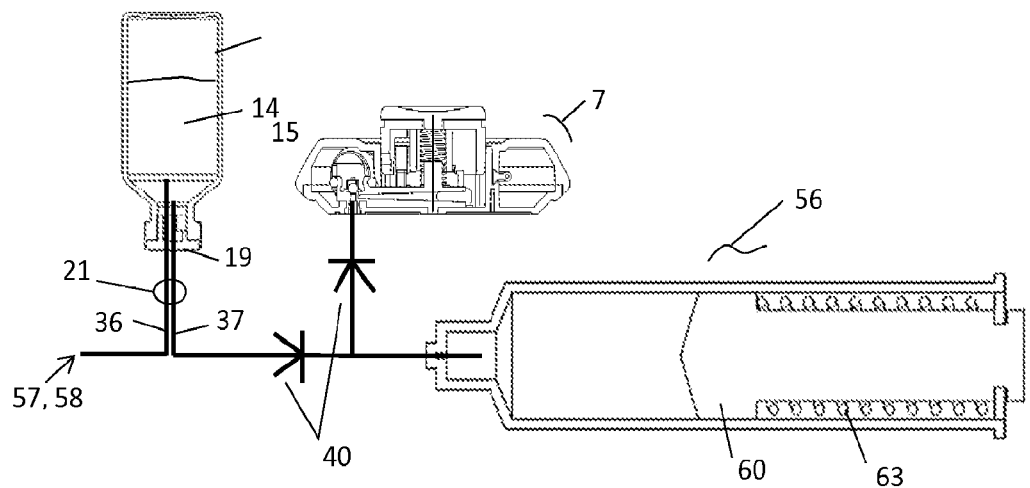
FIG. 80 is a schematic of an alternative embodiment of the single vial transfer system in FIG. 64 with a drug vial, a transfer apparatus with a first variable pressure chamber, an injection device including the fluid pathways with check valves and flow restrictors.

Referring to FIG. 80, the volume of the pressure chamber 56 could be set to be larger than the total fluid volume 14 in the vial 15 so that additional air 58 is drawn into chamber 56 from the vial 15. This additional air 58 could be helpful in insuring that all of the liquid 14 is removed from the vial 15 and removal or clearing of residual liquid 14 in the fluid pathways 35 between the vial 15 and the chamber 56. Additionally, during transfer of the liquid 14 from the chamber 56 to the injection device 7, the additional air may be useful in the removal or clearing of residual liquid 14 in the fluid pathways 35 between the chamber 56 and the injection device 7.

Figure 81:
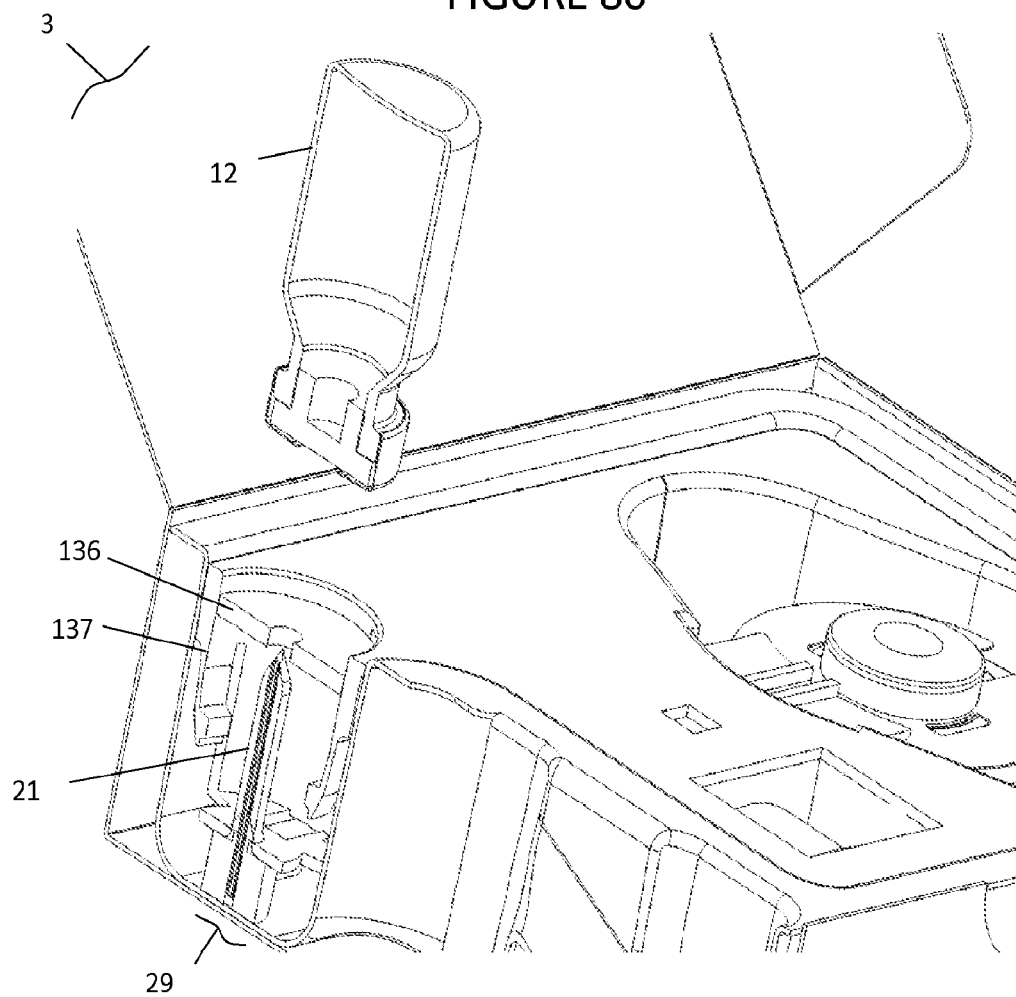
FIG. 81 is a cross-section of FIG. 77 depicting an aspect of the vial receiving area.

Referring to FIG. 81, the transfer apparatus 3 comprises a vial holder docking area 29 that may include an elongated vial access member or piercing member 21. This vial holder docking area 29 may include a vial access protector 136. The vial access protector 136 is locked and held in a first position above the vial access member 21 by locking fingers 137 within the vial holder docking area 29 prior to insertion of the vial 12 or vial holder to cover the vial access member 21 and prevent inadvertent vial access member stick by the user. When the vial 12 or vial holder is inserted into the vial holder docking area 29, the vial 12 or vial holder displaces the locking fingers 137 and unlocks the vial access protector 136. Once unlocked, the vial access protector 136 is movably slidable within the vial holder docking area 29 with the vial 12 or vial holder.

Figure 82:
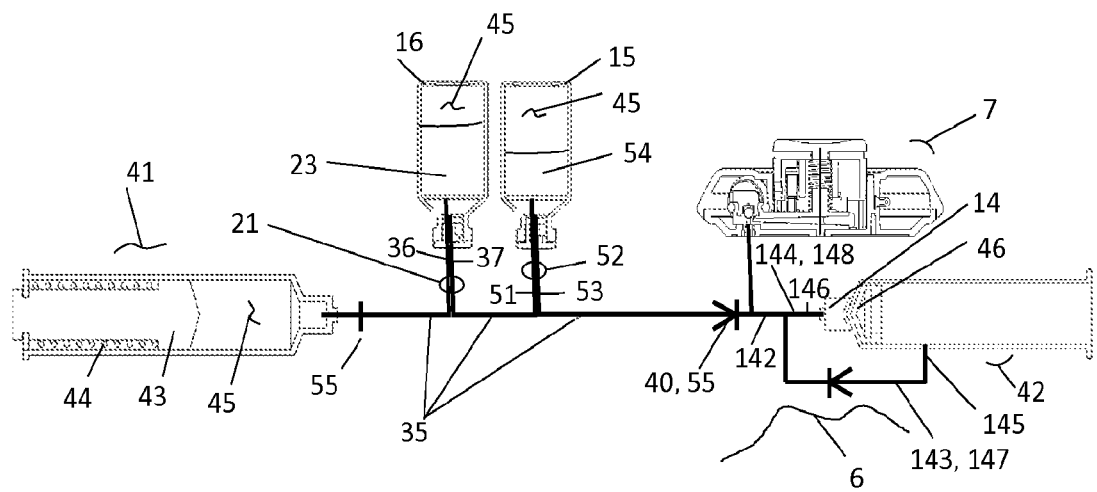
FIG. 82 is a schematic of a dual vial transfer system with a first vial, a second vial, a transfer apparatus with a first and second variable pressure chambers and injection device including the fluid pathways.

Referring to FIG. 82, flow restrictors 55 may be used in the fluid pathway 35 to control and/or delay the transfer time and/or increase the mixing time. Small lumen tubing could be used at any point in the flow path 35 to restrict flow and increase the time of mixing/transfer for times up to an hour or more. One method to control and/or delay the transfer time and/or increase mixing time between the second pressure chamber 42 and the injection device 7 is by the use of multi-lumen fluid pathways 142 between the second pressure chamber 42 and injection device 7. Each lumen 143, 144 of the fluid pathway 142 is attached to a specific location 145, 146 on the second pressure chamber 42, preferably spaced apart along the travel of the piston and has an internal diameter 147, 148 sized to provide for a specific flow rate through that lumen 143, 144 based on the pressure within the second pressure chamber 42. Initially as the second pressure chamber piston 46 starts its advance in the chamber 42, the fluid mixture 14 is dispensed through all of the lumens 143, 144 in the fluid pathway 142 to the injection device 7. Once the piston passes over an attachment point 145 between a lumen 143 and the pressure chamber 42, the flow of fluid through that lumen 143 stops and fluid 14 is forced through the remaining lumen 144. Multiple lumens and attachment points could be positioned along the pressure chamber. The final lumen 144 available from flow of fluid 14 could be sized with an internal diameter 148 that is very small. Accordingly, the flow rate would be very low, increasing the time to transfer the fluid 14 from the chamber 42 to the injection device 7. This delay of transfer allows for increase mixing time.

Figure 83:
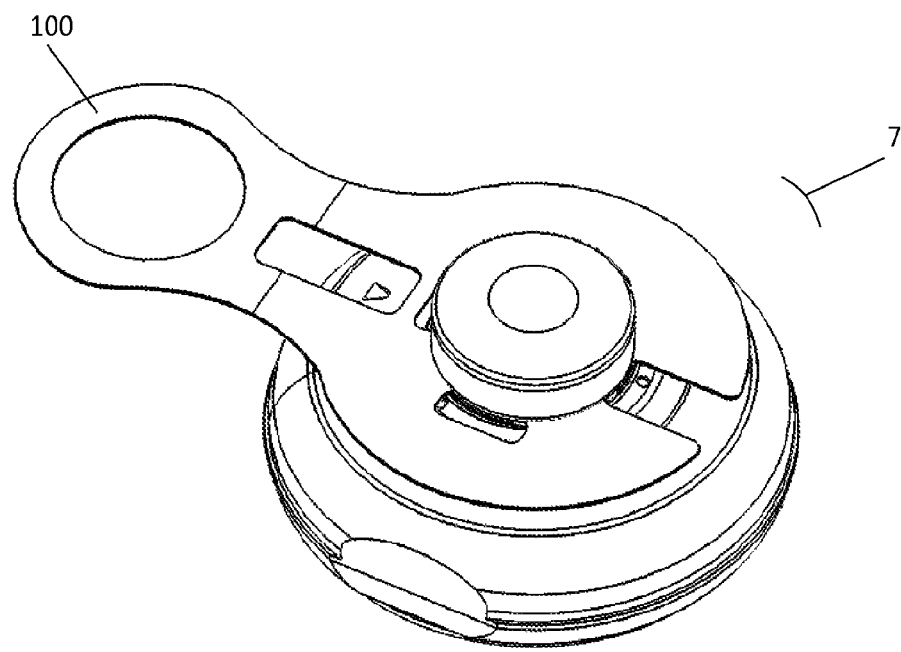
FIG. 83 is a perspective view of an injection device with the attached safety sleeve.

Referring to FIG. 83, a safety, such as a safety pin or safety sleeve 100 may be configured to allow for removal from the injection device 7 in any direction to release the injection device 7 to be ready to fire (inject).

Figure 84:
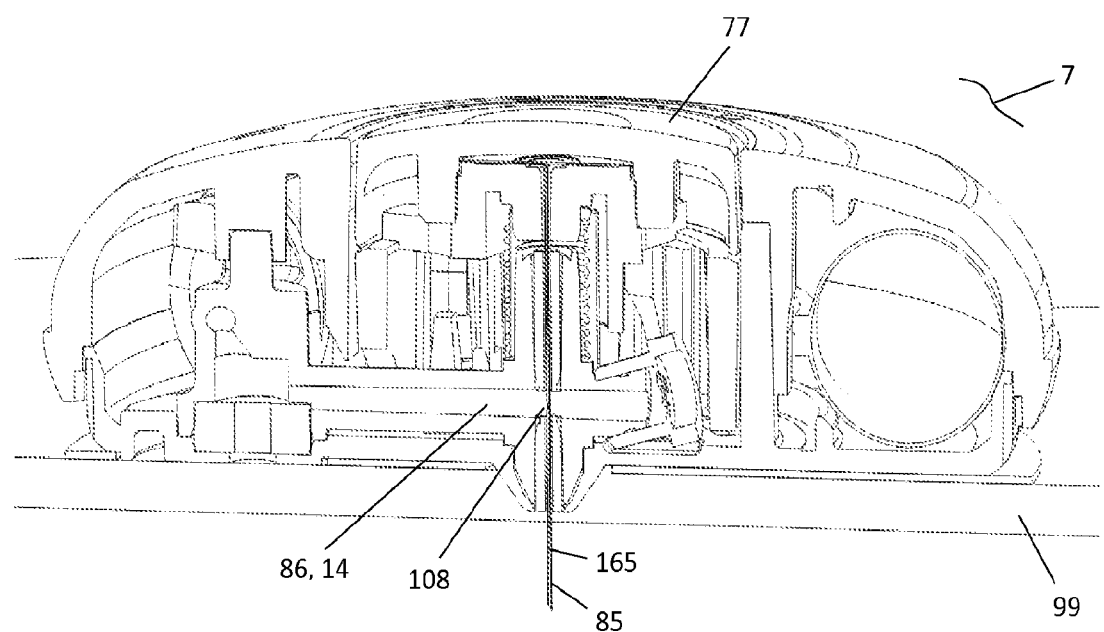
FIG. 84 is a cross-section of FIG. 55 showing an injection device with the button in second position or dispense position.

Referring to FIG. 84, the injection device 7 includes a needle 85 with a side-hole 108 that allows for fluid communication between the fluid pathway 86 and the skin 99 once the button 77 is fully depressed in the injection device 7. This starts dispense of the injectable 14. The inner diameter 165 of the needle 85 is significant in controlling the rate of dispense from the injection device 7. Referencing the Hagen-Poiseuille equation for fluid flowing in a pipe, the flow rate through a pipe is directly proportional to the radius of the pipe the fourth power. Thus, small variations in the inner diameter 165 of the needle 85 result in large variations in flow through the needle 85, especially as the inner diameter 165 gets smaller. The needle 85 in the injection device 7 may range from 21G to 34G (Stubs Iron Wire Gauge System) in various wall thickness configurations. This range corresponds to an inner diameter 165 range of 0.021" to 0.003", recognizing that there is manufacturing variation or tolerance with the needle inner diameter 165 in any given needle size. This is based on needle size and can have an inner diameter variation as much as ±0.00075". To limit the range of the inner diameter 165 within any given needle size and resulting variation in flow, the needle 85 may be modified prior to assembly into the injection device 7. This modification could include crimping, flattening or rolling the needle to a new, prescribed effective inner diameter 165 over a portion of the length of the needle 85 from a circular shape to a non-circular shape. This has the advantage of allowing for specific delivery rate control from the injection device 7.

Figure 85:
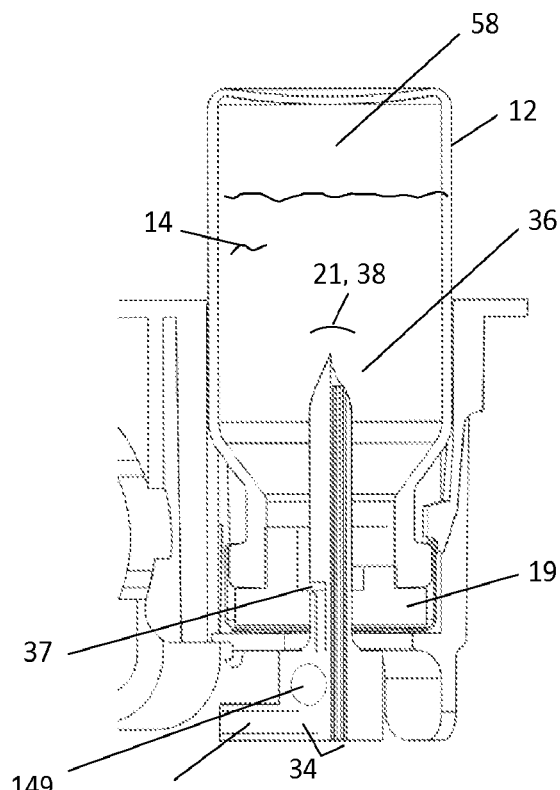
FIG. 85 is a cross-section of FIG. 59 depicting an aspect of the vial holder area showing the drug vial, vial access member and angle sensor in the open position.
Figure 86:
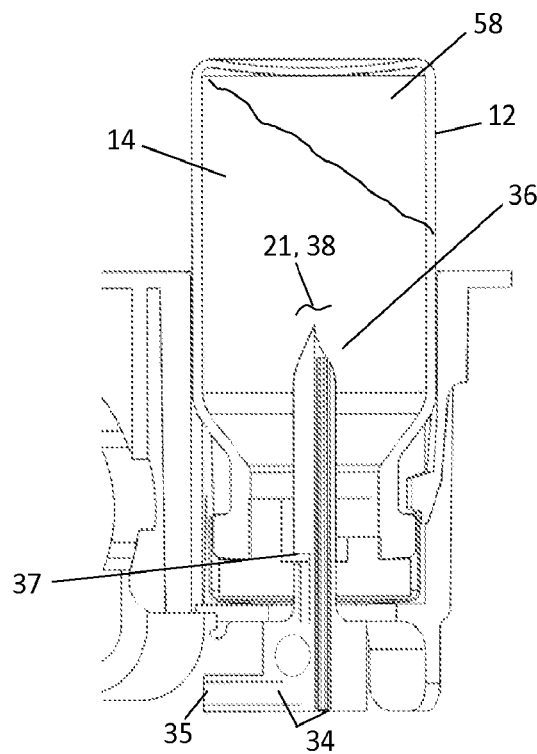
FIG. 86 is a cross-section of FIG. 59 depicting an aspect of the vial holder area showing the drug vial, vial access member and angle sensor in the closed position.

Referring to FIGS. 85-86, the lumen openings 38 in the vial access member 21 can be oriented to allow for introduction of pressurized air or liquid through the upper inlet tube 36 and output of the vial contents 14 through the lower output tube 37. Further, the outlet opening 37 may be positioned near the bottom of the inverted vial 12, adjacent to the septum 19 to encourage the entire contents 14 of the vial 12 to enter the outlet port 37 and be removed from the vial 12. The preferred sequence for removal of the contents 14 from the vial 12 is first all of the fluid 14 in the vial 12 and then the air 58 from the vial 12. This is achieved with the current embodiment when the orientation of the transfer apparatus 3 is oriented as shown in FIGS. 85-86. Based on the geometry of the vial access member 21 within the vial 12, this sequence of all fluid 23 then air 58 removal is achieved up to transfer apparatus 3 angles of +/−45 degrees from horizontal. Beyond this angle, there is the possibility that air 58 is introduced before or during fluid 14 removal from the vial 12. An angle sensor 149 may be positioned in or around the vial access member 21 to sense the angle of the transfer apparatus 3. It may have direct communication with either or both of the lumen openings 38 and/or each or both of the inlet tube 37 and output tube 36. In the current embodiment as shown in FIG. 85, when the transfer apparatus 3 is at an angle less than 45 degrees, the sensor 149 allows fluid communication between the outlet port 37 and the fluid pathways 35. As shown in FIG. 86, if the transfer apparatus 3 were tilted to an angle greater than 45 degrees, the sensor 149 may rotate or translate to a new position to shut off the fluid communication between the outlet port 37 and the fluid pathways 35.

Figure 87:
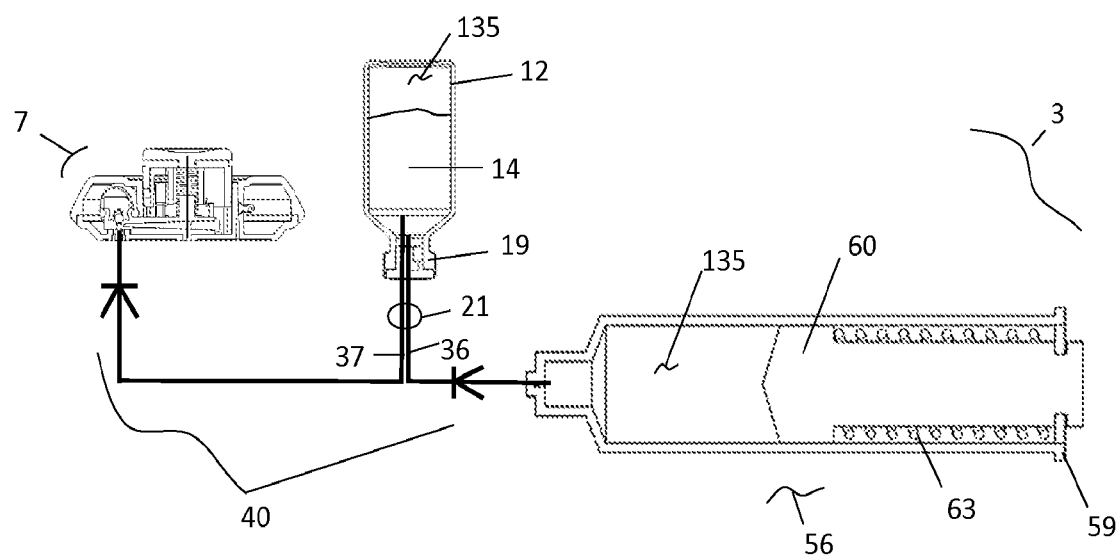
FIG. 87 is a schematic of an alternative embodiment of the single vial transfer system with a drug vial, a transfer apparatus with a first variable pressure chamber and an injection device including the fluid pathways with check valves.

Referring to FIG. 87, an alternative transfer apparatus 3 within a single vial system that does not perform mixing but only transfers fluid 14 from a single vial 12 to the injection device 7 is provided. This alternative transfer apparatus 3 includes a vial 12, a variable volume pressure chamber 56 and fluid pathways 35 to direct the contents 14 from the vial 12 into the injection device 7. The inlet tube 36 of the vial access member 21 is connected to the variable volume pressure chamber 56 with fluid pathways 35. The outlet tube 37 of the vial access member 21 is connected to the injection device 7 through fluid pathways pressure chamber 56.

Referring to FIG. 87, the full insertion of the vial 12 into the transfer apparatus 3 by the user causes the introduction of the vial access member 21 through the septum 19 of the vial 12 to access the contents 14 of the vial 12. This also triggers the release of the pressure chamber trigger 59. The plunger 60 is in a retracted position and the pressure chamber 56 is full of air 135. The pressure release trigger 59 releases the plunger 60 within the pressure chamber 56 connected to a dispense spring 63. The dispense spring 63 advances the plunger 60 and displaces air 135 from the pressure chamber 56 into the single vial 12 though the inlet tube 36. Air 135 entering the vial 12 displaces the fluid 14 out of the vial 12 through the outlet tube 37 into the injection device 7. This continues until all of the fluid 14 is displaced out vial 12 into the injection device 7. Check valves 40 could be employed to prevent fluid 14 from going back into the vial 12 or fluid 14 from going back into the pressure chamber 56.

The present subject matter has been described in terms of specific embodiments for purposes of illustration only, and not limitation. It is to be understood that the scope of the subject matter is not limited to only the illustrated embodiments or equivalents thereof but has broader application in embodiments of varying configuration and use some of which may be readily apparent upon reading this description and others only after some study and/or development.

The invention claimed is:

1. An injection device comprising:
   a housing;
   an arcuately expandable bladder made of elastomeric material and positioned within the housing, the bladder including a proximal end, a distal end and a wall extending between the proximal end and the distal end;
   an injection cannula moveable within a central portion of the housing between a pre-dispense position and a dispense position, the injection cannula not being in fluid flow communication with the bladder in the pre-dispense position and being in fluid flow communication with the bladder in the dispense position;
   a manifold within the housing attached to the proximal end of the bladder, the manifold having a fluid inlet port and a fluid pathway communicating between the fluid inlet port and the bladder for introduction of liquid under pressure into the bladder;
   the distal end of the bladder being moveable within the housing, wherein the bladder elongates between the proximal end and the distal end and the distal end of the bladder moves along an arcuate path away from the proximal end of the bladder and at least partially around the central portion of the housing as liquid is introduced under pressure to expand the bladder; and
   wherein an elastic force in the bladder wall when the bladder is arcuately expanded provides the pressure to expel liquid from the bladder and through the injection cannula, whereby the distal end of the bladder moves along the arcuate path and toward the proximal end due to the elastic force in the bladder wall as liquid flows from the bladder through the injection cannula.

2. The injection device of claim 1 including adhesive configured to attach the injection device to a patient's skin.

3. The injection device of claim 1 further comprising a cannula actuator which is configured so that the injection cannula is moveable from the pre-dispense position to a first depth into a patient's skin and then to a second depth less than the first depth, where the injection cannula is retained at the second depth.

4. The injection device of claim 3 wherein the injection cannula includes a side hole configured so that when the injection cannula is in the pre-dispense position and the first depth position, the side hole is not in fluid flow communication with the bladder and when the injection cannula is in the second depth position, the side hole is in fluid flow communication with the bladder.

5. The injection device of claim 4 further comprising a septum positioned within the housing and configured to seal around a periphery of the side hole of the injection cannula when the injection cannula is in the pre-dispense position and the first depth position.

6. The injection device of claim 1 further comprising a cannula actuator that includes a viewing window and a cavity in fluid communication with a proximal end of the injection cannula so that blood accumulates in the cavity and is visible through the viewing window after the injection cannula is inserted into a blood vessel of a patient.

7. The injection device of claim 1 in which the injection cannula is selectively moveable from the dispense position to another position in which the injection cannula is not in communication with the bladder to pause the flow of a drug to the patient.

8. The injection device of claim 1 wherein the housing is circular and includes a spiral recess within which the distal end of the bladder is positioned and moves along as liquid is introduced into and expelled from the bladder.

9. The injection device of claim 1 wherein the distal end of the bladder is provided with an indicator.

10. The injection device of claim 1 further comprising a mandrel connected to the distal end of the bladder and configured so that the bladder is prestressed to an expanded condition even after all liquid has been expelled from the bladder.

11. The injection device of claim 1 wherein the bladder wall includes an area of increased thickness along a side of the bladder wall, where the area of increased thickness deflects less than a remaining portion of the bladder wall so that the distal end moves along the arcuate path when a volume of liquid under pressure is introduced into the bladder.

12. The injection device of claim 1 wherein the bladder is C-shaped.

13. The injection device of claim 1 wherein the bladder is arranged in a planar helical configuration.

14. The injection device of claim 1 wherein the bladder is arranged in a spiral configuration.

15. The injection device of claim 1 wherein the bladder expands along a planar partial circular path.

16. The injection device of claim 1 wherein the bladder expands along a circular path.

17. The injection device of claim 1 wherein the bladder expands along a spiral path.

18. The injection device of claim 17 further comprising a mandrel connected to the distal end of the bladder and configured so that the bladder is prestressed to an expanded condition even after all liquid has been expelled from the bladder.

19. An injection device comprising:
   a housing;
   an arcuately expandable bladder made of elastomeric material and positioned within the housing, the bladder including a proximal end, a distal end and a wall extending between the proximal end and the distal end;
   an injection cannula moveable within a central portion of the housing between a pre-dispense position and a dispense position, the injection cannula not being in fluid flow communication with the bladder in the pre-dispense position and being in fluid flow communication with the bladder in the dispense position;
   a manifold within the housing attached to the proximal end of the bladder, the manifold having a fluid inlet port and a fluid pathway communicating between the fluid inlet port and the bladder for the introduction of liquid under pressure into the bladder;

the distal end of the bladder being moveable within the housing; wherein the bladder elongates between the proximal end and the distal end and the distal end of the bladder moves along an arcuate path away from the proximal end of the bladder and at least partially around the central portion of the housing as liquid is introduced under pressure to expand the bladder;

the bladder wall including a radially inner wall portion and a radially outer wall portion relative to the central portion of the housing; the radially inner wall portion being thicker than the radially outer wall portion along a length of the elongated wall substantially parallel to the arcuate path between the proximal end and the distal end of the bladder to induce the bladder to extend in the arcuate path at least partially around the central portion of the housing as it expands; and wherein an elastic force in the bladder wall when the bladder is arcuately expanded provides pressure to expel liquid from the bladder and through the injection cannula, whereby the distal end of the bladder moves along the arcuate path and toward the proximal end due to the elastic force in the bladder wall as liquid flows from the bladder through the injection cannula.

20. The injection device of claim 19 wherein the thicker radially inner wall portion is molded into the bladder wall.

21. The injection device of claim 19 wherein the thicker radially inner wall portion includes a strip of material bonded to the radially inner wall portion.

22. An injection device comprising:

a housing;

an arcuately expandable bladder made of elastomeric material and positioned within the housing, the bladder including a proximal end, a distal end and a wall extending between the proximal end and the distal end;

an injection cannula moveable within a central portion of the housing between a pre-dispense position and a dispense position, the injection cannula not being in fluid flow communication with the bladder in the pre-dispense position and being in fluid flow communication with the bladder in the dispense position;

a manifold within the housing attached to the proximal end of the bladder; the manifold having a fluid inlet port and a fluid pathway communicating between the fluid inlet port and the bladder for the introduction of liquid under pressure into the bladder;

the distal end of the bladder being moveable within the housing, wherein the bladder elongates between the proximal end and the distal end and the distal end of the bladder moves along an arcuate path away from the proximal end of the bladder and at least partially around the central portion of the housing as liquid is introduced under pressure to expand the bladder;

the bladder wall including a radially inner wall portion and a radially outer wall portion relative to the central portion of the housing, the radially inner wall portion being thicker than the radially outer wall portion along a length of the elongated wall substantially parallel to the arcuate path between the proximal end and the distal end of the bladder to induce the bladder to extend in the arcuate path at least partially around the central portion of the housing as it expands;

a guide extending at least partially around the central portion of the housing and slidably constraining the thicker radially inner wall portion to move along the arcuate path during bladder contraction and expansion; and wherein an elastic force in the bladder wall when the bladder is arcuately expanded provides pressure to expel liquid from the bladder and through the injection cannula, whereby the distal end of the bladder moves along the arcuate path and toward the proximal end due to the elastic force in the bladder wall as liquid flows from the bladder through the injection cannula.

23. The injection device of claim 22 wherein the central portion of the housing includes a cylindrical wall and the guide includes a groove extending at least partially around the cylindrical wall and wherein a portion of the thicker radially inner wall portion of the bladder is slidably received in the groove.

* * * * *